US011186586B2

(12) United States Patent
Tang et al.

(10) Patent No.: US 11,186,586 B2
(45) Date of Patent: Nov. 30, 2021

(54) LUMINOGENS FOR BIOLOGICAL APPLICATIONS

(71) Applicant: THE HONG KONG UNIVERSITY OF SCIENCE AND TECHNOLOGY, Hong Kong (CN)

(72) Inventors: Benzhong Tang, Hong Kong (CN); Ji Qi, Hong Kong (CN); Ming Chen, Hong Kong (CN); Wei Qin, Hong Kong (CN); Pengfei Zhang, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 0 days.

(21) Appl. No.: 16/469,037

(22) PCT Filed: Dec. 12, 2017

(86) PCT No.: PCT/CN2017/115629
§ 371 (c)(1),
(2) Date: Jun. 12, 2019

(87) PCT Pub. No.: WO2018/108070
PCT Pub. Date: Jun. 21, 2018

(65) Prior Publication Data
US 2020/0079787 A1 Mar. 12, 2020

Related U.S. Application Data

(60) Provisional application No. 62/498,093, filed on Dec. 15, 2016, provisional application No. 62/602,531, filed on Apr. 27, 2017, provisional application No. 62/605,977, filed on Sep. 6, 2017.

(51) Int. Cl.
| | | |
|---|---|---|
| C07D 495/04 | (2006.01) | |
| A61K 49/00 | (2006.01) | |
| C07D 241/24 | (2006.01) | |
| C07D 285/14 | (2006.01) | |
| C07D 417/14 | (2006.01) | |
| C07D 487/02 | (2006.01) | |
| C07D 513/02 | (2006.01) | |
| C07D 517/02 | (2006.01) | |

(52) U.S. Cl.
CPC ........ *C07D 495/04* (2013.01); *A61K 49/0023* (2013.01); *C07D 241/24* (2013.01); *C07D 285/14* (2013.01); *C07D 417/14* (2013.01); *C07D 487/02* (2013.01); *C07D 513/02* (2013.01); *C07D 517/02* (2013.01)

(58) Field of Classification Search
None
See application file for complete search history.

(56) References Cited

FOREIGN PATENT DOCUMENTS

CN 106831650 A2 6/2017

OTHER PUBLICATIONS

Li et al. Photoswitchable aggregation-induced emission of a dithienylethene-tetraphenylethene conjugate for optical memory and super-resolution imaging. 2013 RSC Adv. 3: 8967-8972. (Year: 2013).*
Ishi-I, T. et. "Light-emitting properties of donor-acceptor and donor-acceptor-donar dyes in solution, solid ,and aggregared states: structure-property relationship of emission behavior", RSC Advances, vol. 5, Oct. 14, 2015, p. 89171-89187.
McNamara, L.E. et al. "Donor-Acceptor-Donor Thienopyrazines via Pd-Catalyzed C-H Activation as NIR Fluorescent Materials", J.Org.Chem., vol. 81, Nov. 24, 2015, p. 31-42.
Lu, X. et al. "Controlling the Charge Transfer in D-A-D Chromophores Based on Pyrazine Derivatives", J.Org.Chem., vol. 79, Jun. 20, 2014, p. 6480-6489.
Kono, T. et al. "Synthesis and photo-electrochemical properties of novel thienopyrazine and quinoxaline derivatives, and their dye-sensitized solar cell performance", Organic Electronic, vol. 13, Oct. 4, 2012, p. 3097-3101.
Kato, S. et al. "Stongly red-fluorescent novel donor-p-bridge-acceptor-p-bridge-donor (D-p-A-p-D) type 2,1,3-benzothiadiazoles with enhanced two-photon absorption cross-sections", Chem. Commun., Sep. 7, 2004, p. 2342-2343.
Qian, G. et al. "Synthesis and Application of Thiadiazoloquinoxaline-Containing Chromophores as Dopants for Efficient Near-Infrared Organic Light-Emitting Diodes", J. Phys. Chem. C., vol. 113, Jan. 7, 2009, p. 1589-1595.
Qian, G. et al. "simple and Efficient Near-Infrared Organic Chromophores for Light-Emitting Diodes with Single Electroluminescent Emission above 1000nm", Adv. Mater., vol. 21, Dec. 31, 2009, p. 111-116.

* cited by examiner

*Primary Examiner* — Jennifer Lamberski
(74) *Attorney, Agent, or Firm* — Nath, Goldberg & Meyer; Joshua B. Goldberg

(57) ABSTRACT

A compound comprises a donor and an acceptor, wherein at least one donor ("D") and at least one acceptor ("A") may be arranged in an order of D-A; D-A-D; A-D-A; D-D-A-D-D; A-A-D-A-A; D-A-D-A-D; and A-D-A-D-A. The compound may be selected from the group consisting of: MTPE-TP, MTPE-TT, TPE-TPA-TT, PTZ-BT-TPA, NPB-TQ, TPE-TQ-A, MTPE-BTSe, DCDPP-2TPA, DCDPP-2TPA4M, DCDP-2TPA, DCDP-2TPA4M, TTS, ROpen-DTE-TPECM, and RClosed-DTE-TPECM. The compound may be used as a probe and may be functionalized with special targeted groups to image biological species. As non-limiting examples, the compound may be used in cellular cytoplasms or tissue imaging, blood vessel imaging, in vivo fluorescence imaging, brain vascular imaging, sentinel lymph node mapping, and tumor imaging, and the compound may be used as a photoacoustic agent.

4 Claims, 46 Drawing Sheets

Chemical shift (ppm)

ns, and high two-photon absorption cross section.

LUMINOGENS FOR BIOLOGICAL APPLICATIONS

CROSS-REFERENCE TO RELATED APPLICATIONS

The present patent application claims priority to provisional U.S. Patent Application No. 62/498,093 filed on Dec. 15, 2016; provisional U.S. Patent Application No. 62/602,531 filed on Apr. 27, 2017; and provisional U.S. Patent Application No. 62/605,977 filed on Sep. 6, 2017, all of which were filed by the inventors hereof and are incorporated by reference herein in their entirety.

TECHNICAL FIELD

The present subject matter relates generally to organic chemistry, photophysics, and biology. In particular, the present subject matter relates to a design strategy and application in developing luminogens and aggregation induced emission (AIE) luminogens (AIEgens) for biological applications. In particular, the present subject matter relates to red fluorescent AIE luminogen with high brightness, large Stokes shift, good biocompatibility, satisfactory photostablility, and high two-photon absorption cross section.

BACKGROUND

Far red/near-infrared (FR/NIR) fluorescence-based technologies have attracted considerable interest in recent years. FR/NIR imaging for in vivo applications shows many advantages over imaging in the visible region, such as deep-tissue penetration due to diminished light scattering, less photo-damage to the body due to low excitation energy, and high signal-to-noise ratio due to minimum interference from the background auto-fluorescence by biological substances in living systems. As a result, much effort has been devoted to developing FR/NIR fluorescent materials for biological applications.

A wide variety of nanostructured materials has been prepared and applied for biological imaging and therapy during the past decade, for example, carbonaceous nanomaterials and inorganic quantum dots (QDs). Although these nanomaterials enjoy the advantage of strong light emission, they suffer from some drawbacks, such as high toxicity and poor processibility, which limit their further applications in the biological field. Conventional organic dyes, on the other hand, possess good biocompatibility and processibility, and several FR/NIR dyes have been synthesized based on the unit of cyanine, BODIPY, rhodamine, and squaraine. However, though all of these conventional FR/NIR dyes show bright emission in solution, their emission is partially or completely quenched when aggregated in an aqueous medium or inside living cells. Thus, it is desirable to develop organic FR/NIR dyes with high fluorescent efficiency in the aggregate state for in vivo applications.

Unlike conventional organic dyes, aggregation-induced emission luminogens (AIEgens) show stronger light emission in the aggregate state. However, few FR/NIR AIEgens have been prepared because of the following difficulties in synthesizing. To endow a luminogen with AIE properties, one may introduce twisting units into the molecular structure to hamper the π-π stacking. However, this will disrupt the π-conjugation, leading to blue-shift, instead of red-shift in the emission. Therefore, a need exists for developing new AIEgens with long luminescence wavelengths to the FR/NIR spectral region and high brightness for in vivobiological and diagnostic applications.

Further, red and near-infrared fluorescent biological imaging has exhibited huge advantages in preclinical research and clinical practice for noninvasive real-time tumor diagnosis and image-guided cancer therapy. Having light emission with a long wavelength plays an indispensable role in biological imaging because of several benefits including deep tissue penetration, negligible biological auto-fluorescence in comparison to blue or green emission, low photo-damage caused by low excitation energy, high signal-to-noise ratio, etc. However, there are always difficulties associated with the design of red/near-infrared emissive dyes, especially with synthetic procedures and less practicability for post-functionalization.

Recently, the fluorescent nanoparticles have caused tremendous interest for biological imaging due to their high photo-stability, large specific surface for post-modification, and intrinsic enhanced permeability and retention (EPR) effect for tumor tissue. However, the traditional organic fluorogens always possess a large planar conjugated structure. They can give strong emission in the solution state, but once fabricated into nanoparticles, the fluorescence is almost quenched. That is, they suffer from the notorious aggregation-caused quenching (ACQ) effect, which is probably due to the formation of excimers upon aggregation and thus hampers their biological applications.

Carbon dots (CDs) are intrinsically emissive nanoparticles, but their emission efficiency is rather low because of their unique emissive species. As such, it is difficult to design CDs with desired properties due to their ambiguous luminescent mechanism. In contrast, for quantum dots (QDs), tunable emission with high luminescent efficiency is easy to achieve, but biological toxicity of inorganic QDs is unavoidable once they are employed for biological application. Further, the ACQ effect also occurs when the concentration of QDs is increased.

In 2001, an abnormal photo-physical phenomenon of aggregation-induced emission (AIE) was observed, which can thoroughly utilize aggregation to play a positive role instead of a negative role in enhancing luminescence. The restriction of intramolecular motion (RIM) has been proven theoretically and experimentally to be the cause of the AIE effect, and with the aid of the RIM mechanism, plenty of organic AIEgens with twisted conformation are tailored with colorful emissions as well as rich functionalities.

To design luminogens with red/near-infrared emissions, the strategies of increasing molecular conjugation or introduction of electron donor-acceptor (D-A) effect are always adopted. However, increasing the molecular conjugation may cause poor solubility of the luminogen and simultaneously make it unstable. Thus, more attention has been directed to design of the red/near-infrared emitter by the rational introduction of the D-A effect. Designed red/near-infrared AIE luminogens (AIEgens) often incorporate tetraphenylethene (TPE) as molecular rotators because TPE is crucial for participating in dissipating the excitation state energy non-radiatively in the solution state and thus determining the AIE effect. However, introduction of TPE in the structure may cause difficulties in the synthesis, as the double bond in TPE easily undergoes thermal-oxidation, photo-oxidation, or photo-isomerization under external stimuli, thus deteriorating the stability of the AIEgen. As such, a need exists for the preparation of red or near-infrared AIEgens with whole aromatic structures (without incorporating a TPE unit) which has simple synthetic steps as well as excellent stability for further applications.

Furthermore, the fluorescence imaging technique is a powerful visualization method which enables real-time following and monitoring of biological processes in vivo. Blood vessels are the primary components for the circulatory system. As such, the application of fluorescent probes for the visualization of blood vasculature in vivo is of great importance, as it will shed light on better understanding, medical diagnosis, and therapeutics for diseases relevant to vascular leakage and obstruction, such as cerebral hemorrhage and cerebral thrombosis.

Two-photon fluorescence microscopy (TPM) has been widely utilized as an important imaging tool for scientific research due to higher penetration depth with NIR excitation, higher spatial resolution with signal to noise ratio, and less photobleaching. However, most reports are limited for utilization of emitters with a small two-photon absorption (2PA) cross section ($\delta_{max}$<50 GM) or with a short wavelength emission. Because of this, some reports are restricted in cell imaging in vitro, without applications in vivo. Therefore, fluorescent materials with longer wavelength emission, high quantum efficiency and high two-photon absorption (2PA) cross section are in urgent demand.

To obtain a longer emission and/or a high two-photon absorption (2PA) cross section, traditional red molecule design has been based on the introduction of nearly planar macrocyclic molecules with extended in-conjugation or with strong electron-donating and electron-accepting units. However, these designed molecules are prone to suffer from aggregation-caused quenching (ACQ) effects in the aggregated state, which thus significantly weakens the performance of the traditional red emitters in relevant applications.

Since 2001, a phenomenon of aggregation-induced emission (AIE) has been observed in some organic luminophores free from the ACQ effect. Unlike conventional luminophores, these luminophores are nonemissive in dilute solutions but are induced to emit intensely when aggregated. Still now, a few red AIE emitters were reported. However, most of them show dual twisted intramolecular charge transfer (TICT) and AIE effects with obvious background emission in THF solution and comparable emission in the aggregated state. For example, the known compound TTB is emissive in THF solution with only slight emission enhancement in the aggregated state. This raised the question as to how the molecule design of TTB could be manipulated to suppress the background emission in solution state. Considering TICT and AIE effects are competitive effects, a simple and direct method is to enhance charge transfer (CT) property, which is an efficient nonradiative decay channel sensitive in solvent polarity in solution state. In this regard, a stronger D-A (donor-acceptor) system with two more arylamine units is introduced to TTB molecular structure for enhanced CT effect. Accordingly, more development has been desired in this area.

Fluorescence imaging is a powerful visualization method, which enables real-time following and monitoring of biological processes in vivo. Blood vessels are the primary components for the circulatory system. As such, there is a need for application of fluorescent probes for the visualization of blood vasculature in vivo. Such an application is of great importance, as it will shed light on better understanding, medical diagnosis, and therapeutics for the common diseases relevant to vascular leakage and obstruction, such as cerebral hemorrhage and cerebral thrombosis.

SUMMARY

In an embodiment, the present subject matter is directed to a compound comprising a donor and an acceptor, wherein each acceptor is independently selected from the group consisting of:

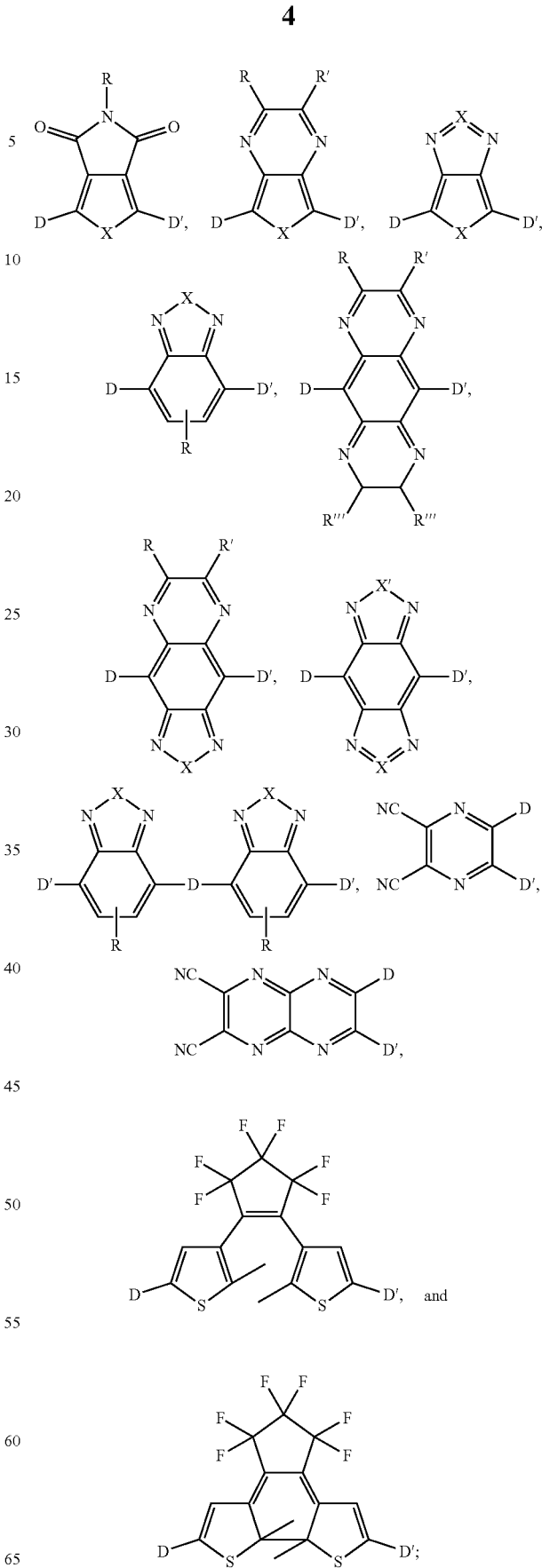

wherein each D and D' is the donor and is independently selected from the group consisting of:
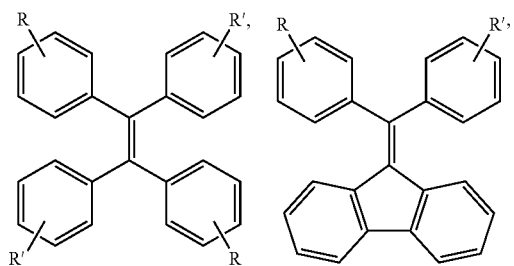
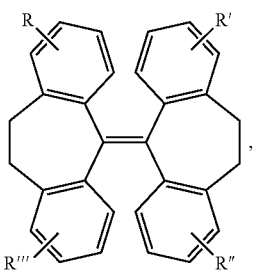
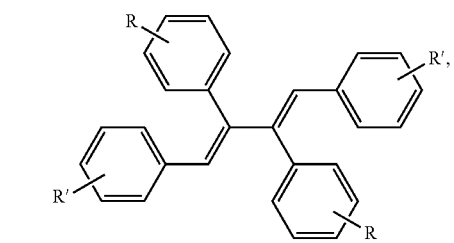
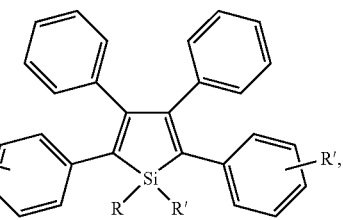
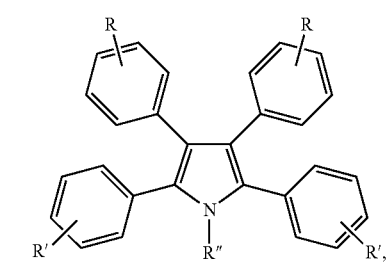
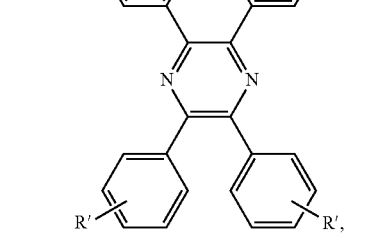
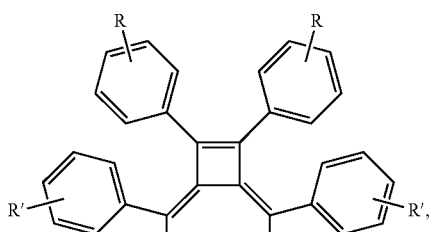
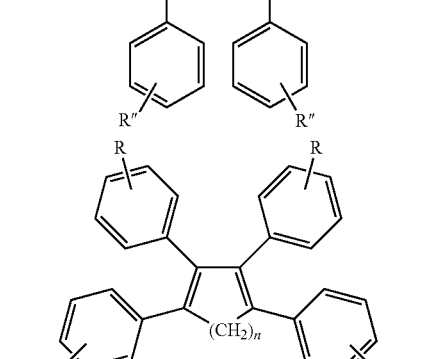
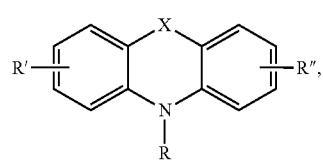
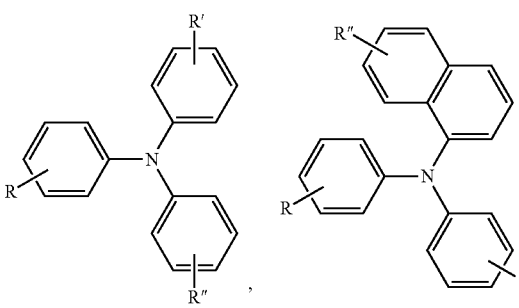
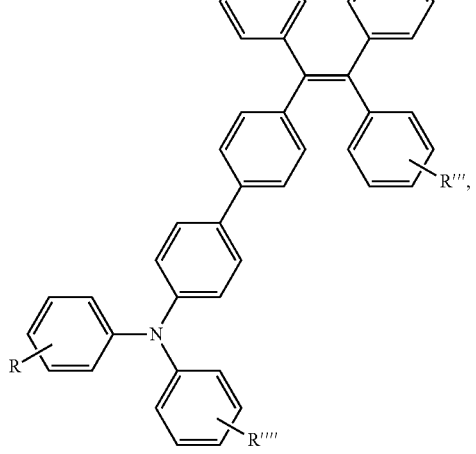

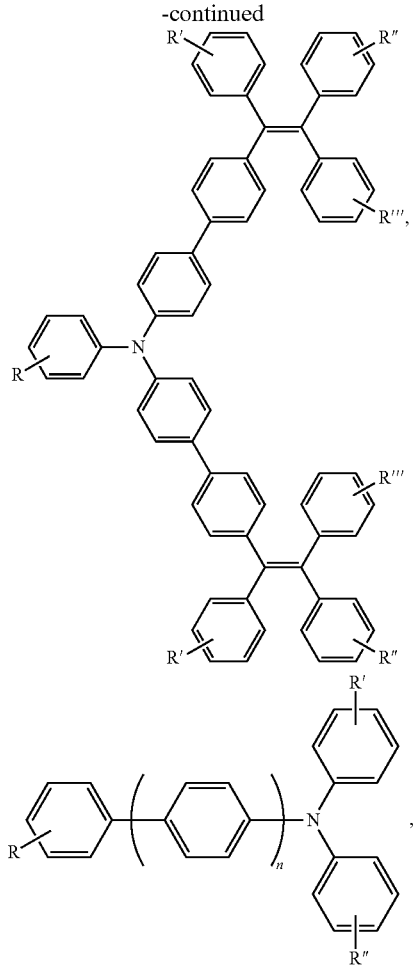
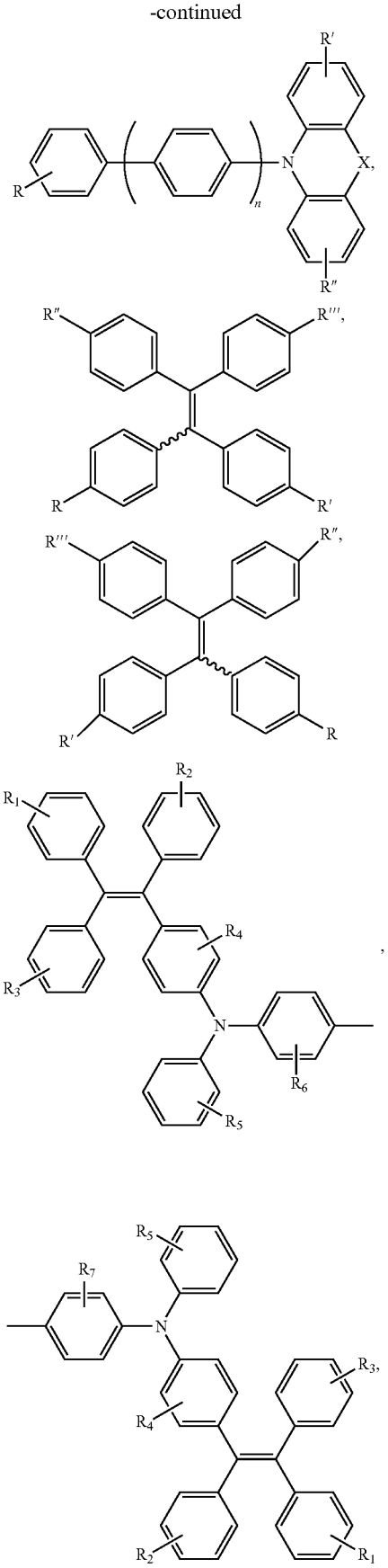

-continued

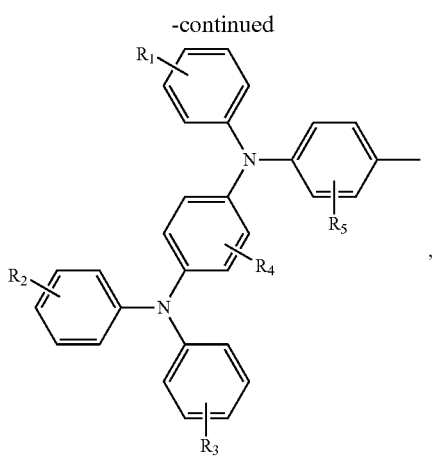

,

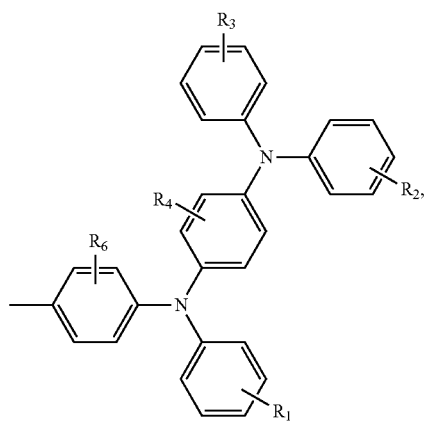

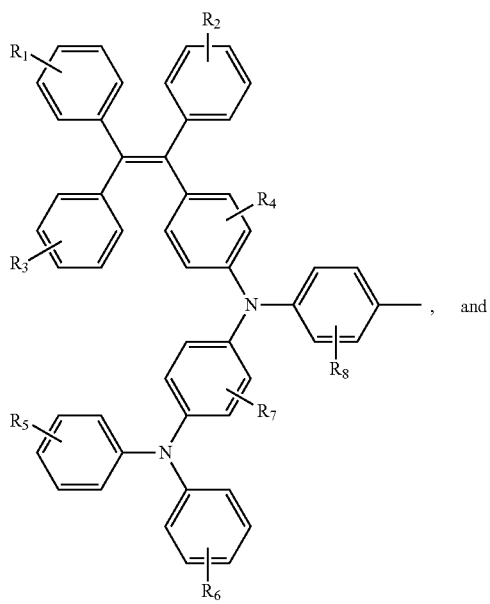

, and

-continued

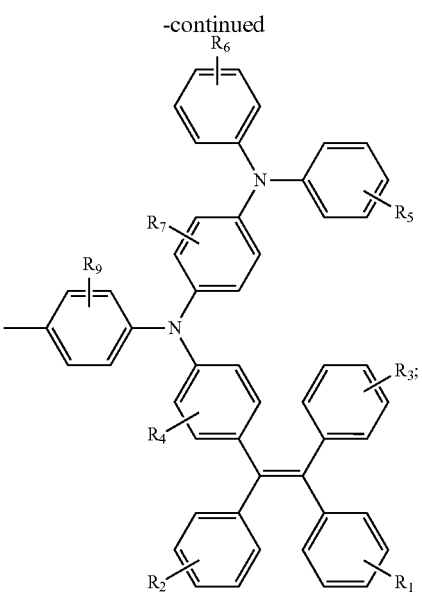

wherein each X and X' is independently selected from the group consisting of: O, S, Se, and Te;

wherein each R, R', R", R"', and R"" is independently selected from the group consisting of: F, H, alkyl, unsaturated alkyl, heteroalkyl, cycloalkyl, heterocycloalkyl, aryl, heteroaryl, carboxyl group, amino group, sulfonic group, alkylthio, alkoxy group, and

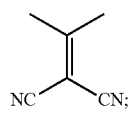

and wherein when any of R, R', R", R"', and R"" is a terminal functional group, then each terminal functional group R, R', R", R"', and R"" is independently selected from the group consisting of $N_3$, NCS, SH, $NH_2$, COOH, alkyne, N-Hydroxysuccinimide ester, maleimide, hydrazide, nitrone group, —CHO, —OH, halide, and charged ionic group;

wherein each $R_1$, $R_2$, $R_3$, $R_4$, $R_5$, $R_6$, $R_7$, $R_8$, and $R_9$ may be substituted or unsubstituted and each $R_1$, $R_2$, $R_3$, $R_4$, $R_5$, $R_6$, $R_7$, $R_8$ and $R_9$ is independently selected from the group consisting of H, alkyl, unsaturated alkyl, heteroalkyl, cycloalkyl, heterocycloalkyl, aryl, heteroaryl, $C_mH_{2m+1}$, $C_{10}H_7$, $C_{12}H_9$, $OC_6H_5$, $OC_{10}H_7$, $OC_{12}H_9$, $C_mH_{2m}COOH$, $C_mH_{2m}NCS$, $C_mH_{2m}N_3$, $C_mH_{2m}NH_2$, $C_mH_{2m}SO_3$, $C_mH_{2m}Cl$, $C_mH_{2m}Br$, $C_mH_{2m}I$,

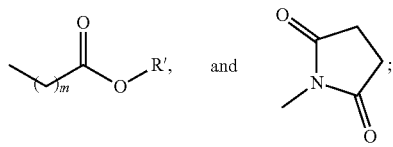

wherein n=0-2; and
wherein m=0 to 20.

In an embodiment, the compound exhibits aggregation-induced emission (AIE).

In an embodiment of the present subject matter, at least one donor and at least one acceptor are arranged in an order selected from the group consisting of:
Donor-Acceptor,
Donor-Acceptor-Donor,
Acceptor-Donor-Acceptor,
Donor-Donor-Acceptor-Donor-Donor,
Acceptor-Acceptor-Donor-Acceptor-Acceptor,
Donor-Acceptor-Donor-Acceptor-Donor, and
Acceptor-Donor-Acceptor-Donor-Acceptor.

In an embodiment, the present subject matter is directed to a probe comprising the present compound, wherein the probe is a red/near-infrared fluorescent probe.

In an embodiment, the present compound is functionalized with special targeted groups to image biological species.

In an embodiment, the present compound is fabricated in PEG/BSA and any amphiphilic molecule matrix, wherein the probe works in a form of nanoparticles. In an embodiment, the nanoparticles are incubated with cells or tissue and used for imaging cellular cytoplasms or tissue. In an embodiment, the nanoparticles are injected into a blood vessel and used for blood vessel imaging.

In an embodiment, the structure is ROpen-DTE-TPECM and the present compound exhibits AIE characteristics and is used for in vivo fluorescence imaging. In an embodiment, the structure is RClosed-DTE-TPECM and the present compound is used as a photoacoustic agent.

In an embodiment, the present subject matter is directed to a probe comprising the present compound, wherein the probe is used for brain vascular imaging, sentinel lymph node mapping, and tumor imaging.

DETAILED DESCRIPTION

Definitions

Figure 1:
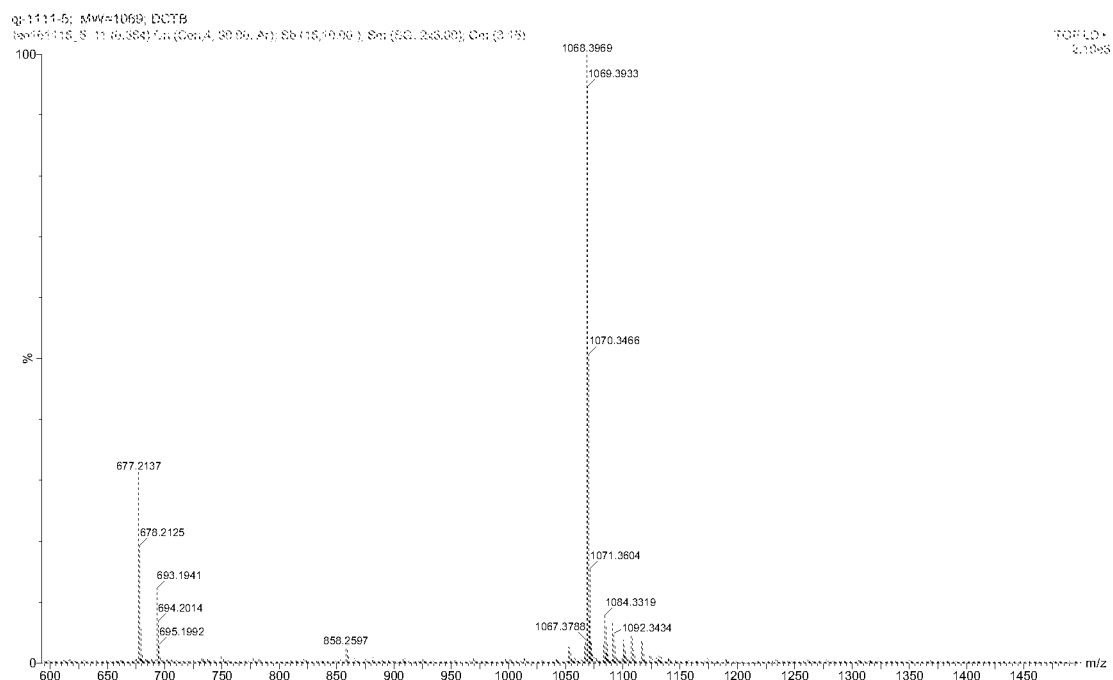
FIG. 1 shows mass spectrum of MTPE-TP.
Figure 2:
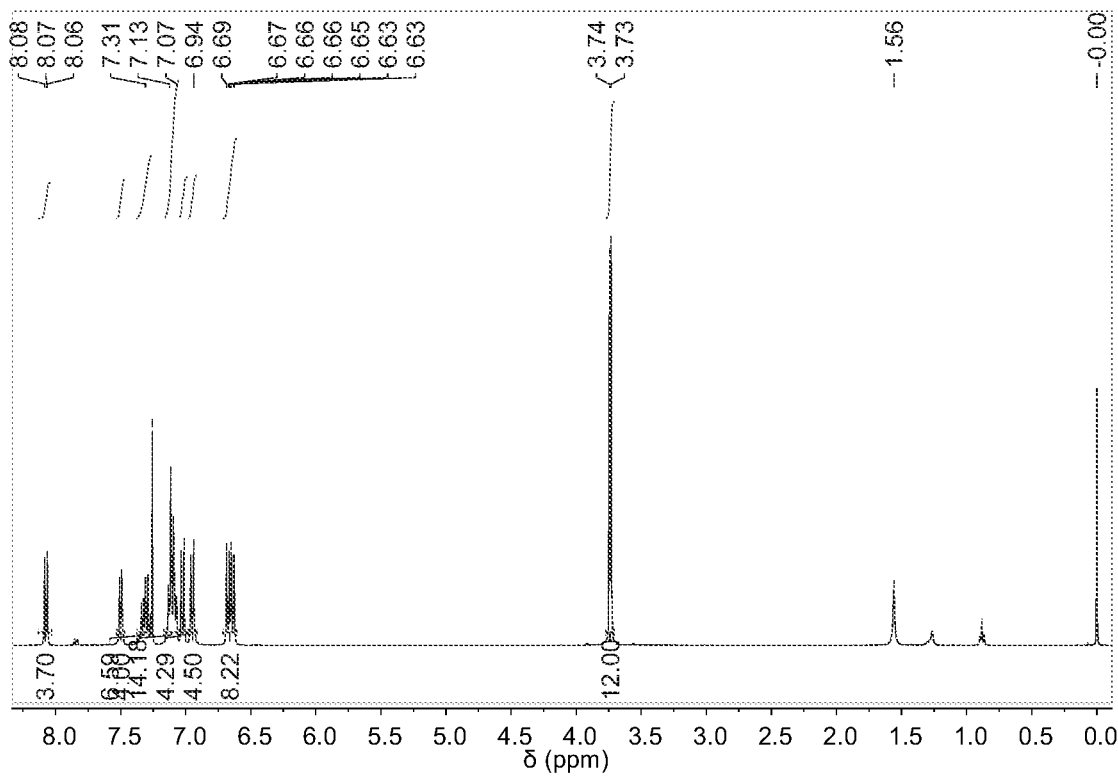
FIG. 2 shows $^1$H-NMR spectrum of MTPE-TP in $CDCl_3$.
Figure 3:
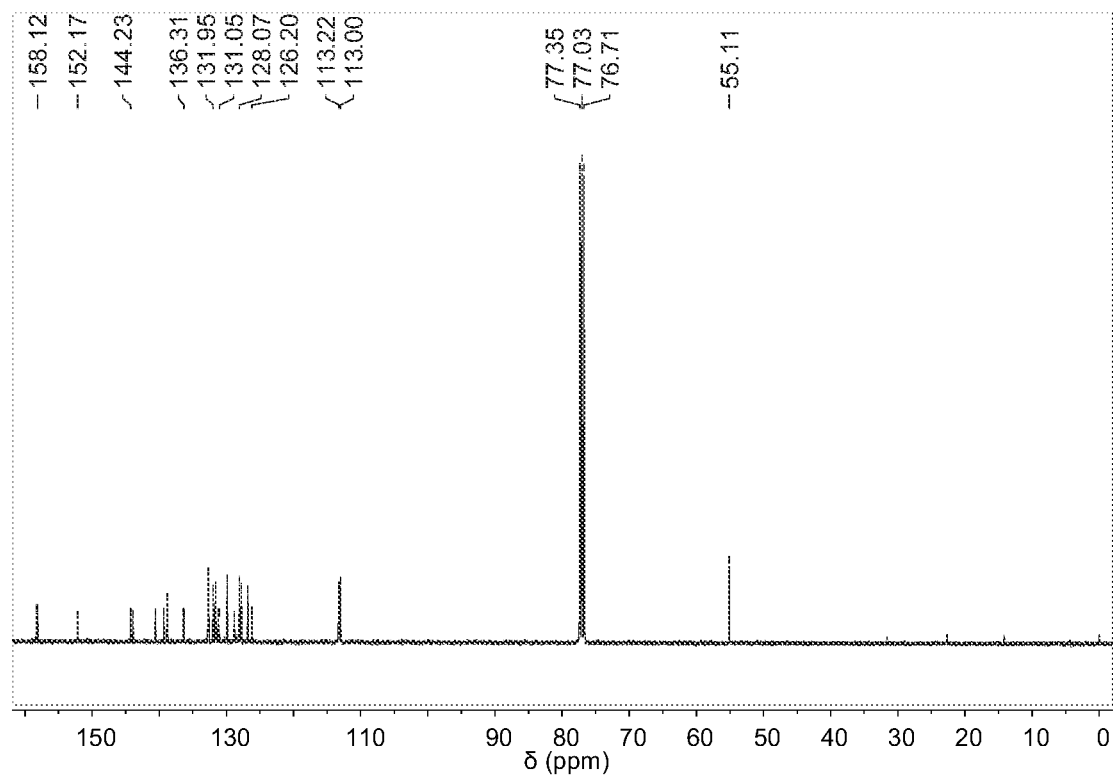
FIG. 3 shows $^{13}$C-NMR spectrum of MTPE-TP in $CDCl_3$.
Figure 4:
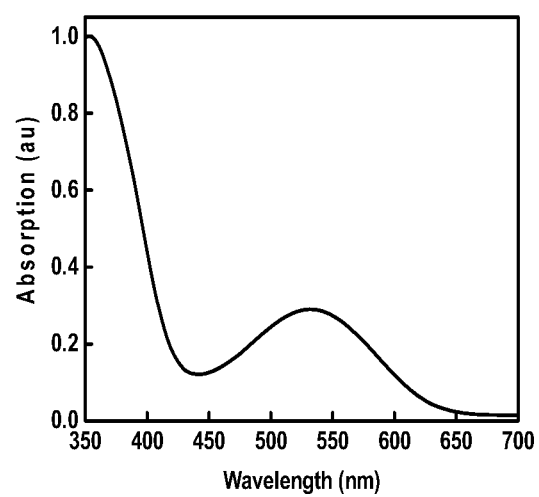
FIG. 4 shows absorption spectrum of MTPE-TP in DMSO.

The following definitions are provided for the purpose of understanding the present subject matter and for constructing the appended patent claims.

It is noted that, as used in this specification and the appended claims, the singular forms "a", "an", and "the" include plural references unless the context clearly dictates otherwise.

"Aggregation-induced emission", or AIE, means the fluorescence/phosphorescence is turned on upon aggregation formation or in the solid state. When molecularly dissolved, the material is non-emissive, but emission is turned on when intramolecular rotation is restricted.

"Emission intensity" refers to the magnitude of fluorescence/phosphorescence normally obtained from a fluorescence spectrometer or fluorescence microscopy measurement; "fluorophore" or "fluorogen" refers to a molecule which exhibits fluorescence; "luminogen" or "luminophore" refers to a molecule which exhibits luminescence; and "AIEgen" refers to a molecule exhibiting AIE characteristics.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Luminogens for Biological Applications

According to the present subject matter, certain compounds have been developed exhibiting a background emission successfully suppressed in line with the expectation of several hundred fold of enhancement in the aggregated state. Following this strategy, many red or NIR emitters with AIE features can be rationally designed in accordance with the following description.

In this regard, in an embodiment, the present subject matter is directed to a compound comprising a donor and an acceptor, wherein each acceptor is independently selected from the group consisting of:

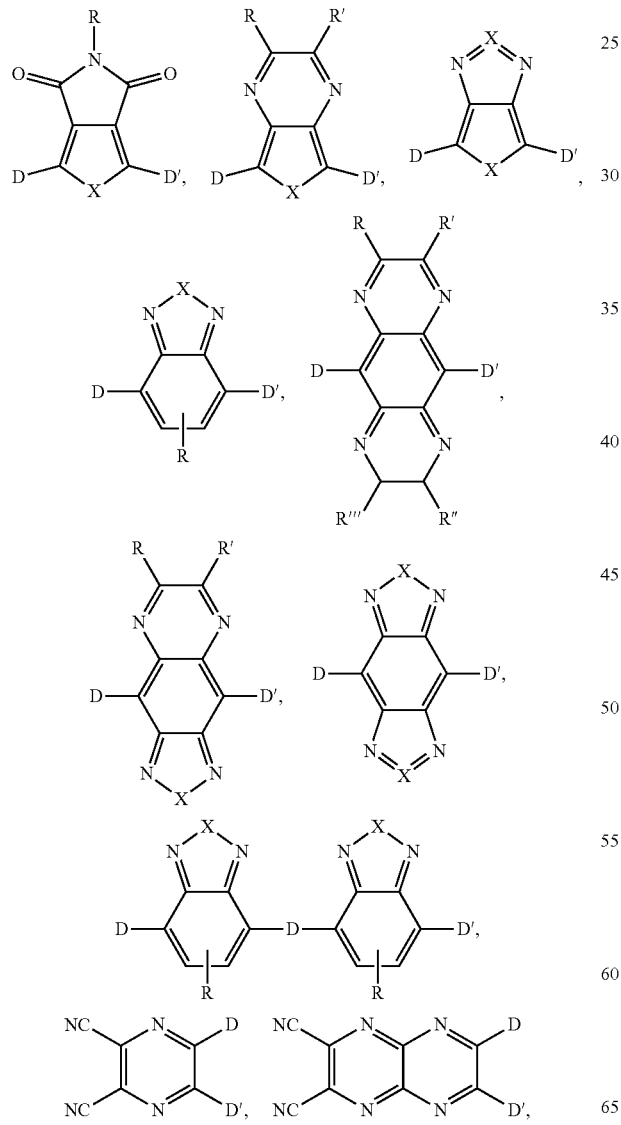

wherein each D and D' is the donor and is independently selected from the group consisting of:

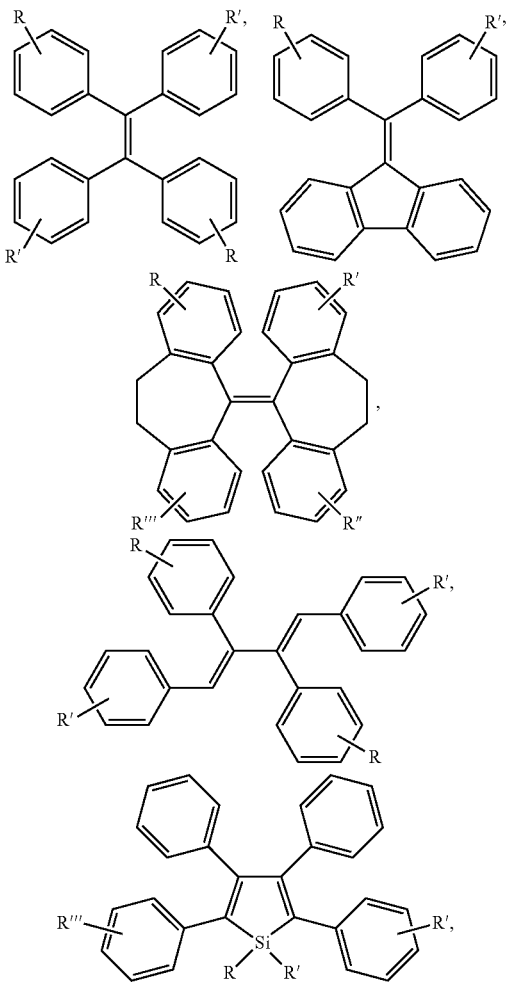

-continued
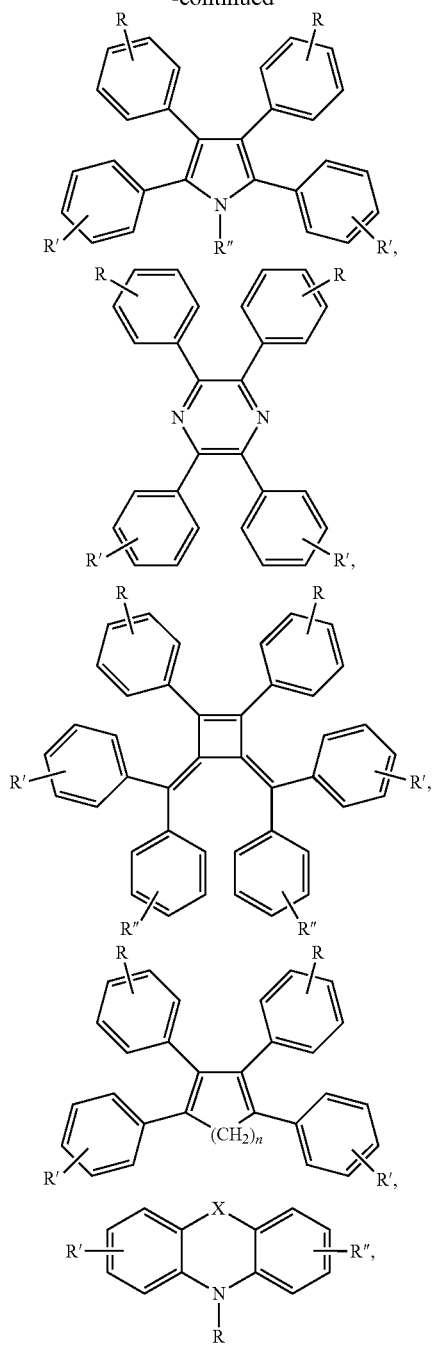
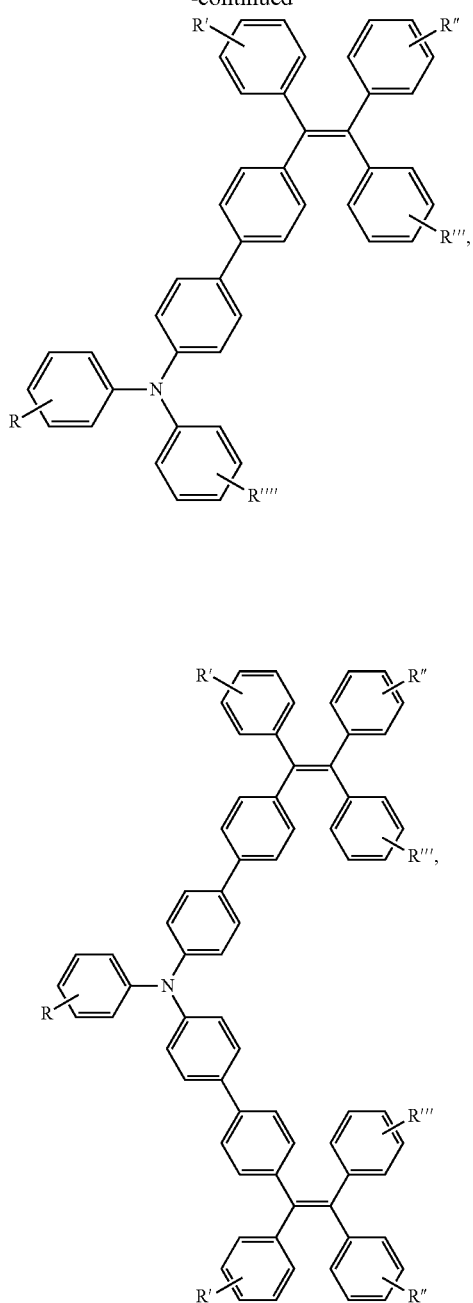
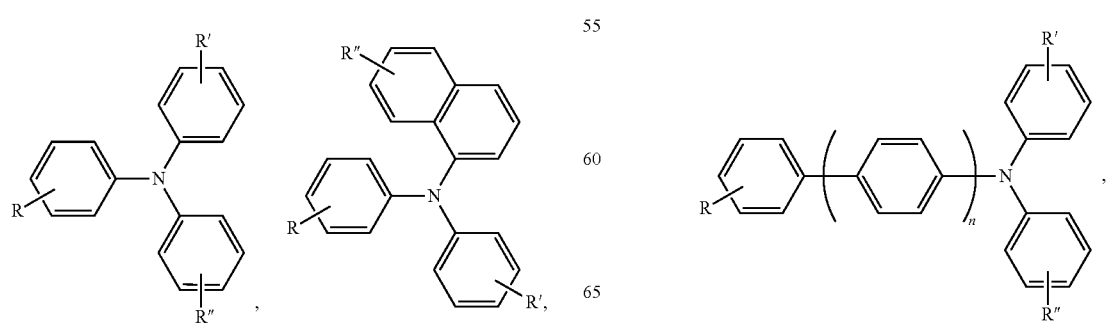

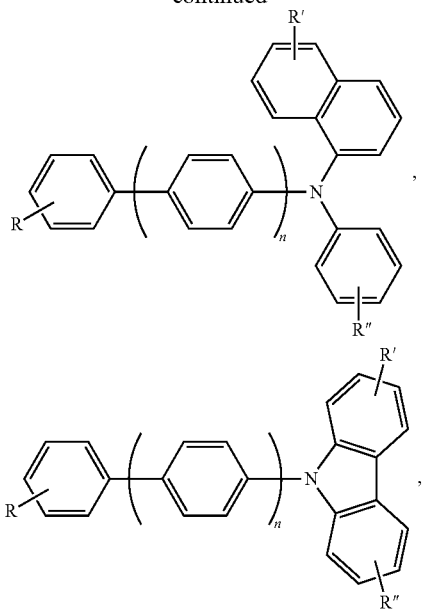
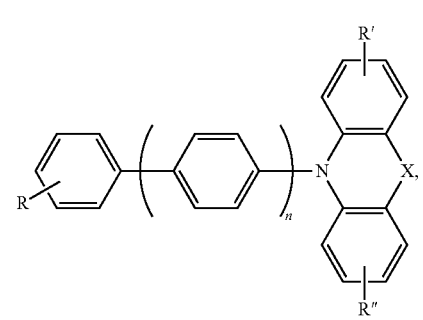
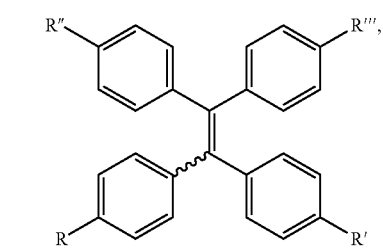
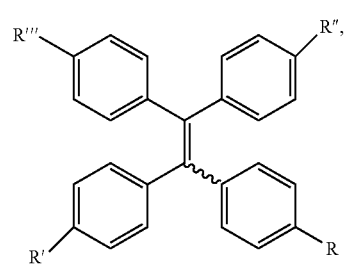
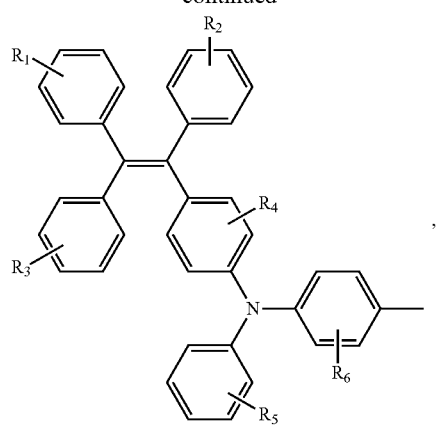
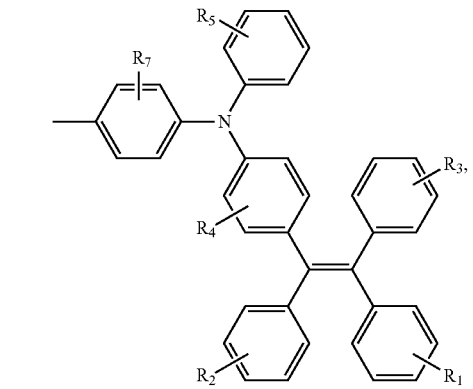
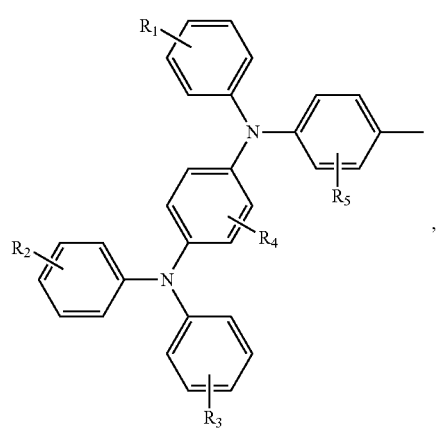

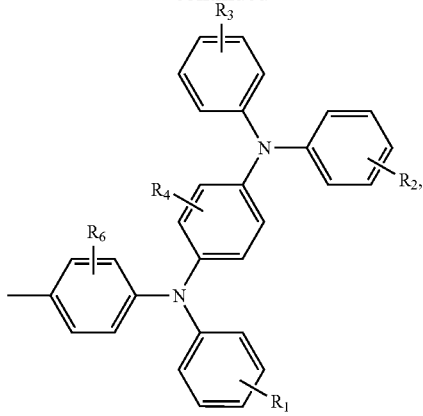

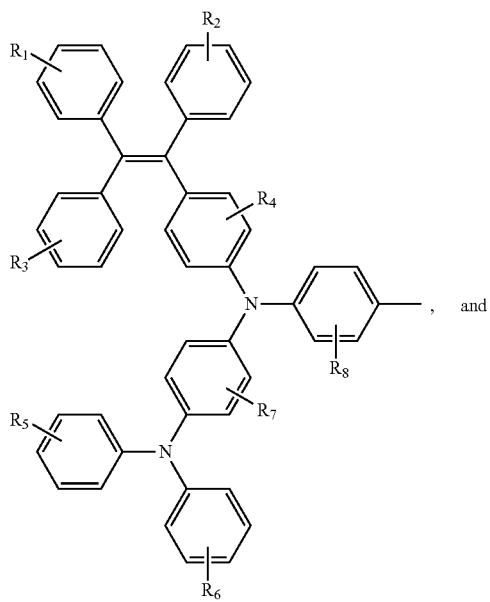, and

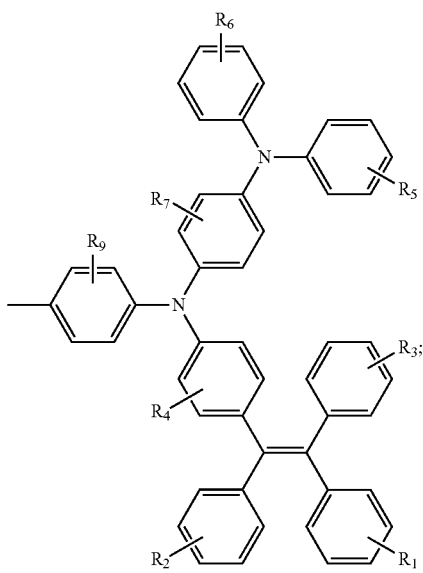

wherein each X and X' is independently selected from the group consisting of: O, S, Se, and Te;

wherein each R, R', R", R''', and R"" is independently selected from the group consisting of: F, H, alkyl, unsaturated alkyl, heteroalkyl, cycloalkyl, heterocycloalkyl, aryl, heteroaryl, carboxyl group, amino group, sulfonic group, alkylthio, alkoxy group, and

and wherein when any of R, R', R", R''', and R"" is a terminal functional group, then each terminal functional group R, R', R", R''', and R"" is independently selected from the group consisting of $N_3$, NCS, SH, $NH_2$, COOH, alkyne, N-Hydroxysuccinimide ester, maleimide, hydrazide, nitrone group, —CHO, —OH, halide, and charged ionic group;

wherein each $R_1$, $R_2$, $R_3$, $R_4$, $R_5$, $R_6$, $R_7$, $R_8$, and $R_9$ may be substituted or unsubstituted and each $R_1$, $R_2$, $R_3$, $R_4$, $R_5$, $R_6$, $R_7$, $R_8$ and $R_9$ is independently selected from the group consisting of H, alkyl, unsaturated alkyl, heteroalkyl, cycloalkyl, heterocycloalkyl, aryl, heteroaryl, $C_mH_{2m+1}$, $C_{10}H_7$, $C_{12}H_9$, $OC_6H_5$, $OC_{10}H_7$, $OC_{12}H_9$, $C_mH_{2m}COOH$, $C_mH_{2m}NCS$, $C_mH_{2m}N_3$, $C_mH_{2m}NH_2$, $C_mH_{2m}SO_3$, $C_mH_{2m}Cl$, $C_mH_{2m}Br$, $C_mH_{2m}I$,

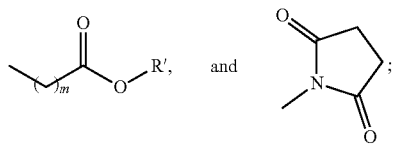

wherein n=0-2; and
wherein m=0 to 20.

For example, in an embodiment, the amino group could be used for further bioconjugation, such as for DNA, peptide, protein, etc.

In an embodiment of the present subject matter, at least one donor and at least one acceptor are arranged in an order selected from the group consisting of:

Donor-Acceptor,

Donor-Acceptor-Donor,

Acceptor-Donor-Acceptor,

Donor-Donor-Acceptor-Donor-Donor,

Acceptor-Acceptor-Donor-Acceptor-Acceptor,

Donor-Acceptor-Donor-Acceptor-Donor, and

Acceptor-Donor-Acceptor-Donor-Acceptor.

In an embodiment, the compound comprises a structure of:
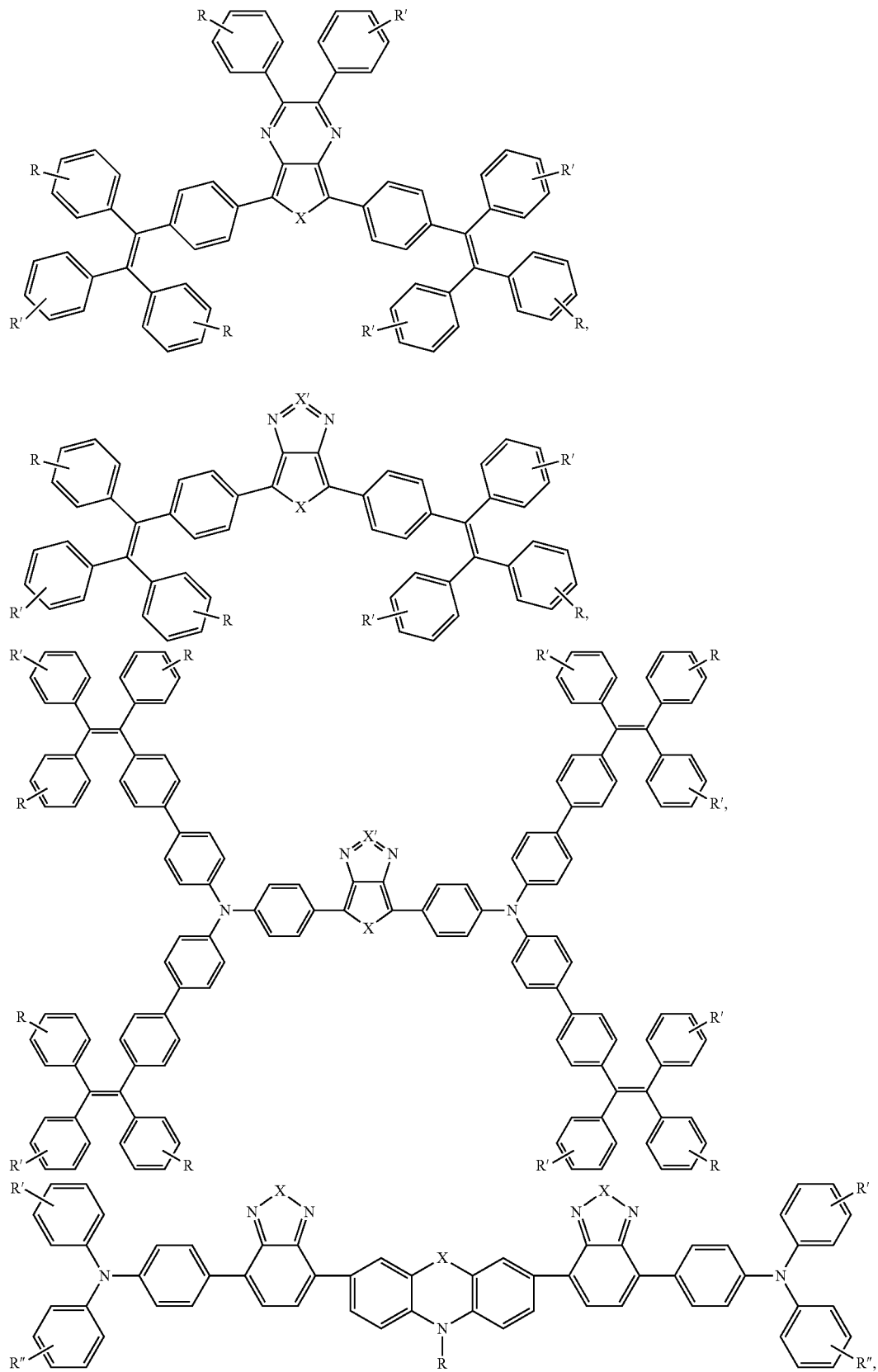

-continued

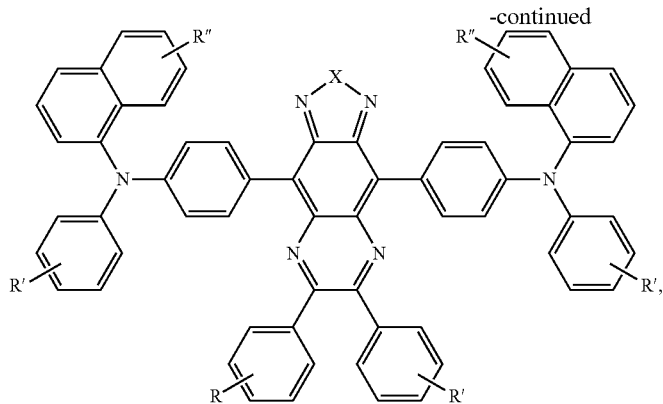

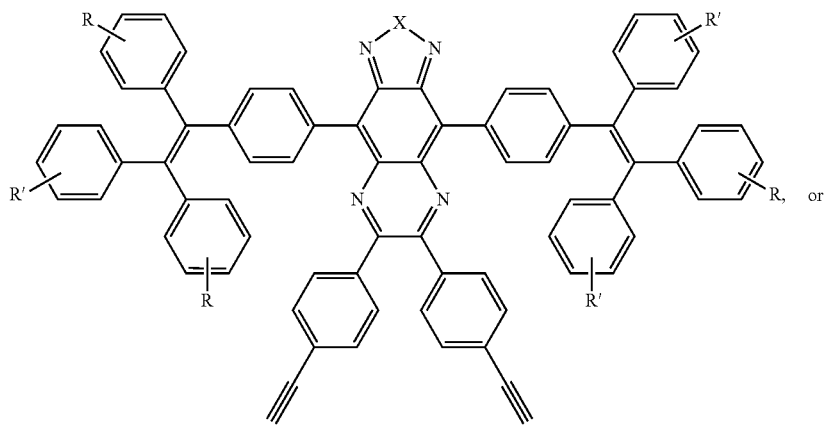

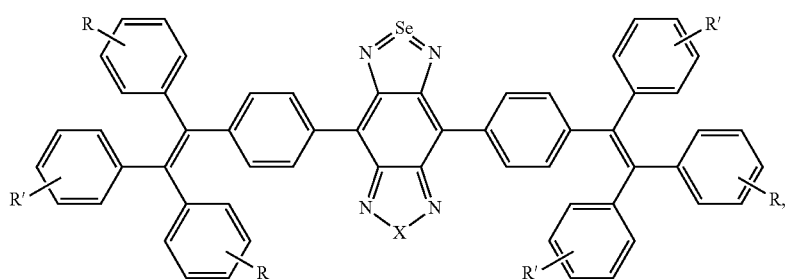

wherein each X' is independently selected from the group consisting of: S, Se, and Te;

wherein each R, R', and R" is independently selected from the group consisting of: F, H, alkyl, unsaturated alkyl, heteroalkyl, cycloalkyl, heterocycloalkyl, aryl, heteroaryl, carboxyl group, amino group, sulfonic group, alkylthio, and alkoxy group; and wherein when any of R, R', and R" is a terminal functional group, then each terminal functional group R, R', and R" is independently selected from the group consisting of $N_3$, NCS, SH, $NH_2$, COOH, alkyne, N-Hydroxysuccinimide ester, maleimide, hydrazide, nitrone group, —CHO, —OH, halide, and charged ionic group.

In an embodiment, the compound comprises a structure of:
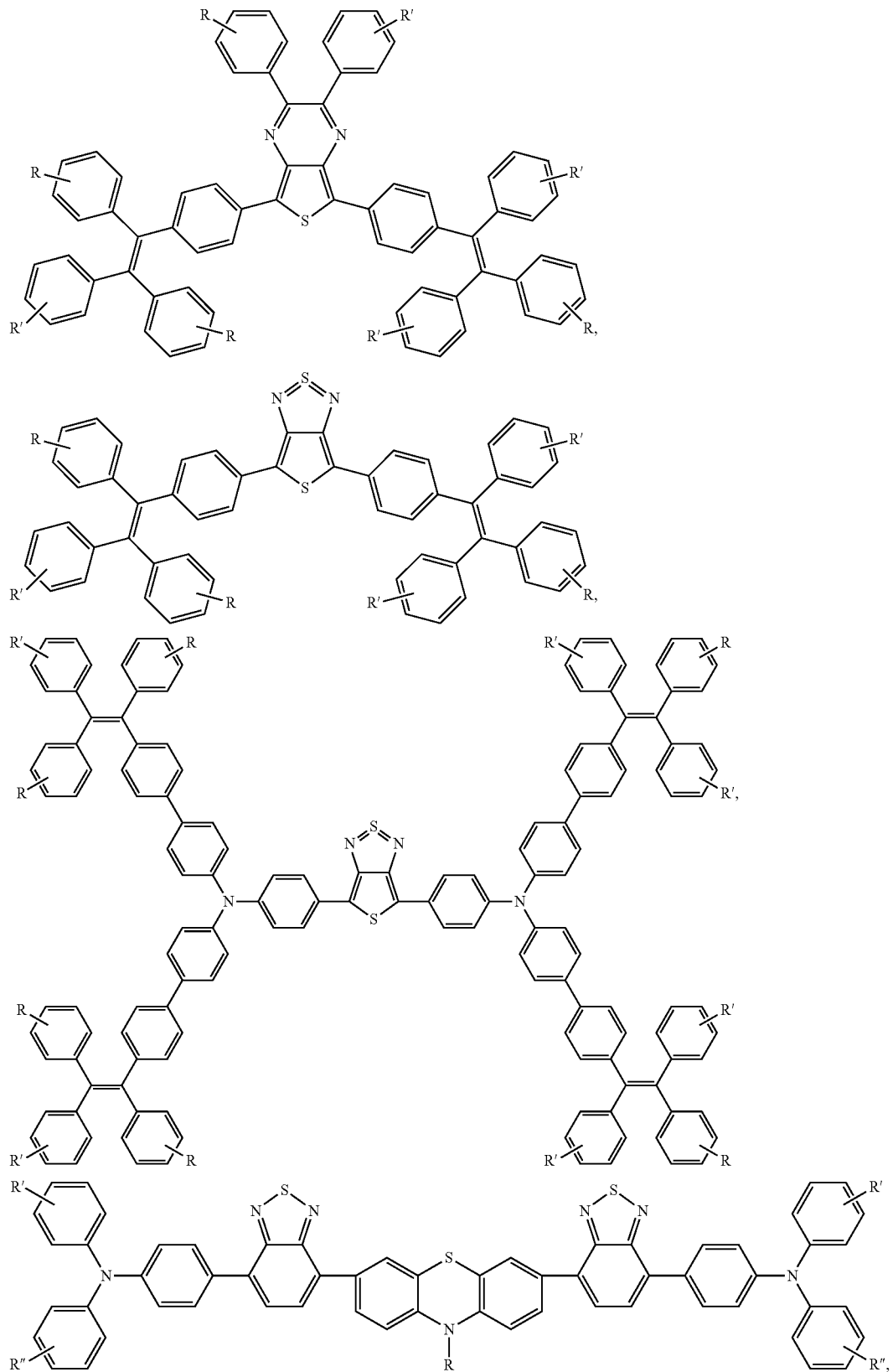

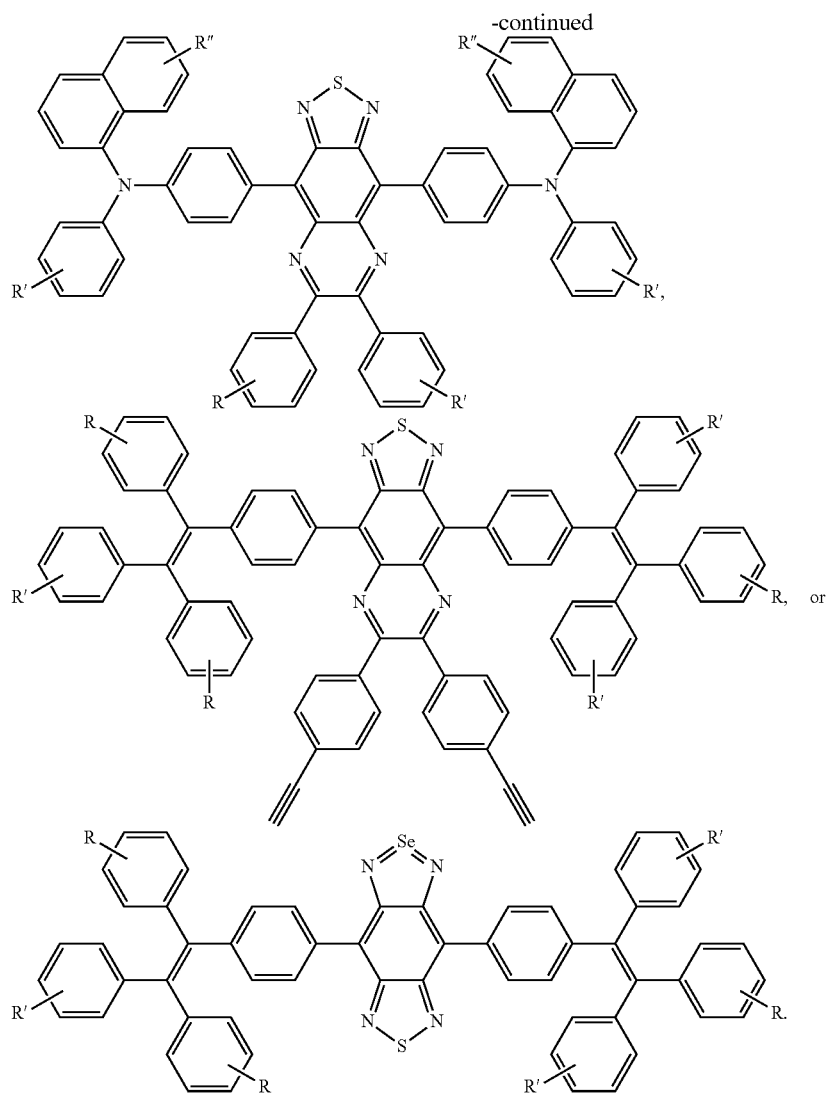
In an embodiment, the compound is selected from the group consisting of:
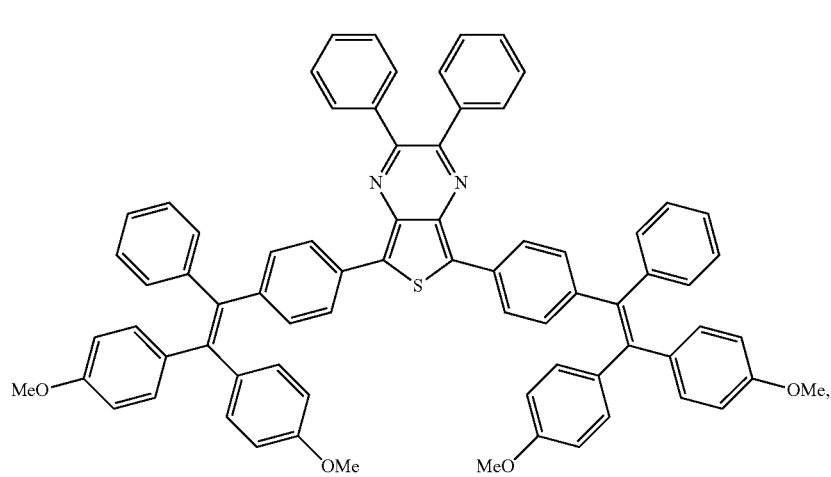

-continued
MTPE-TT
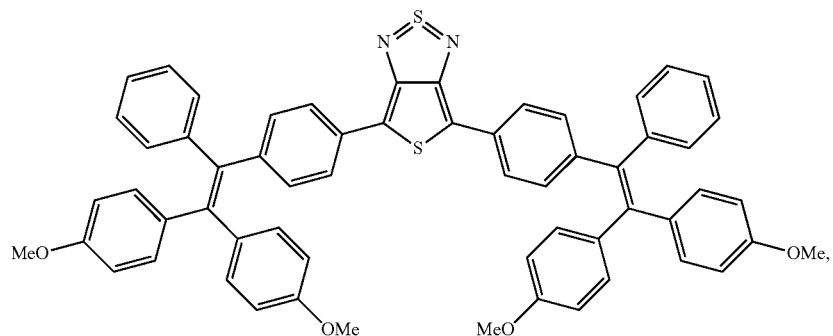
TPE-TPA-TT
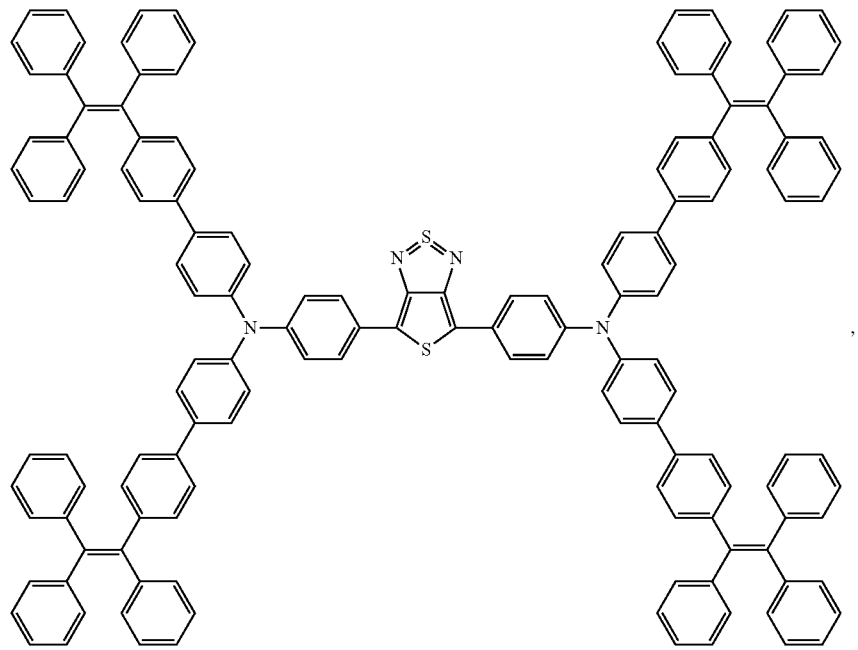
PTZ-BT-TPA
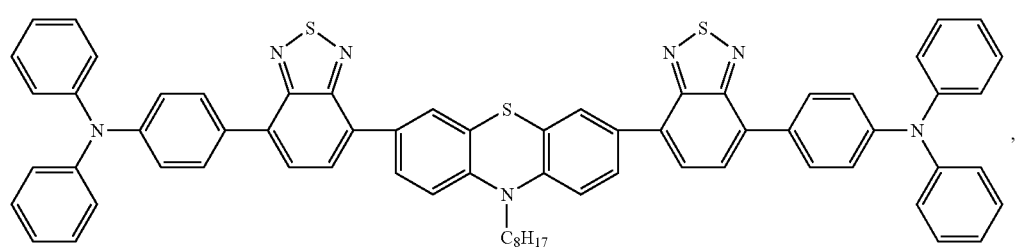
NPB-TQ
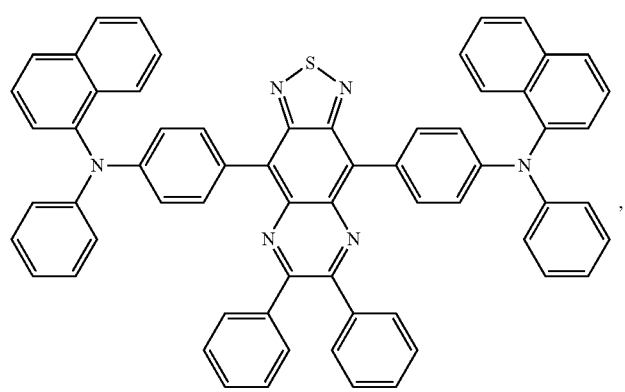

TPE-TQ-A

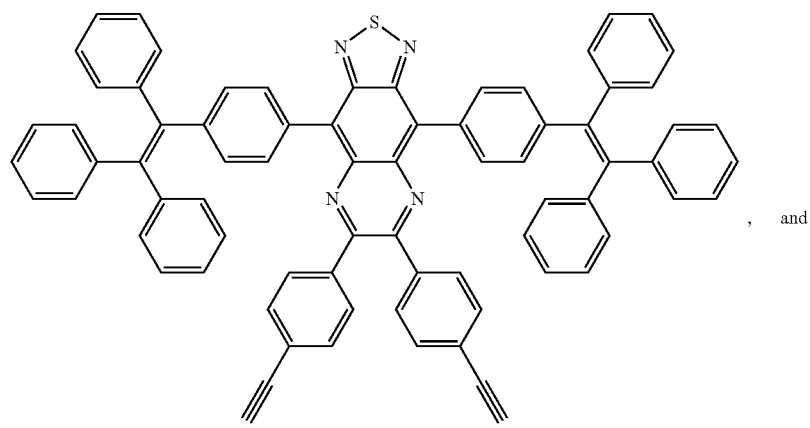

, and

MTPE-BTSe

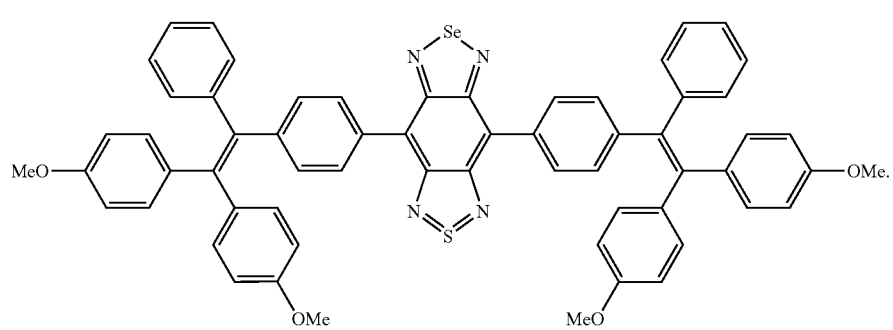

In an embodiment, the compound exhibits aggregation-induced emission (AIE).

In an embodiment, the present subject matter is directed to a probe comprising the present compound, wherein the probe is a far red/near-infrared (FR/NIR) fluorescent probe. In an embodiment, the compound is functionalized with special targeted groups to image biological species. In an embodiment, the compound is fabricated in a PEG matrix and works in a form of nanoparticles. In an embodiment, the nanoparticles can be incubated with cells and used to image cellular cytoplasms.

In an embodiment, the present compound is a pyrazine-based red/near-infrared AIEgen wherein each acceptor is independently selected from the group consisting of:

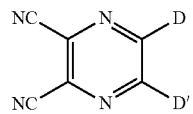 and 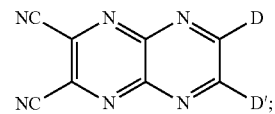

wherein each D and D' is the donor and is independently selected from the group consisting of:

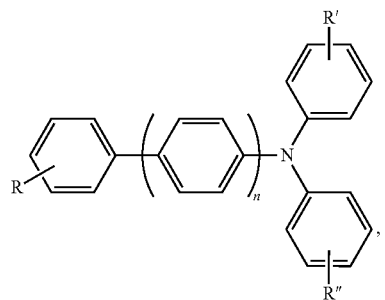

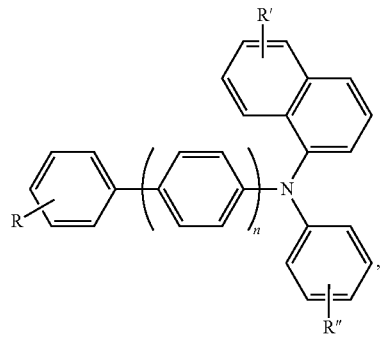

-continued

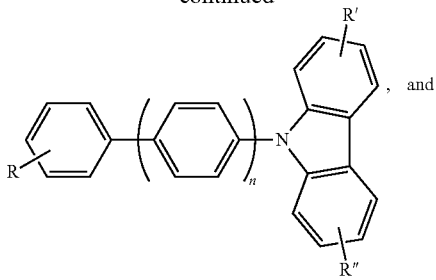, and

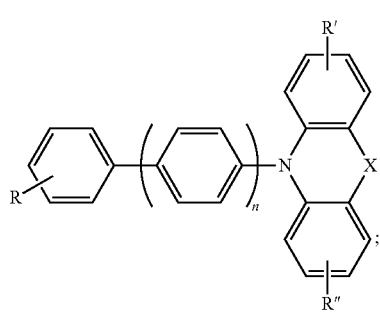;

wherein n=0-2;
wherein each X is independently O or S;
wherein each R, R', and R" is independently selected from the group consisting of: F, H, alkyl, unsaturated alkyl, heteroalkyl, heterocycloalkyl, aryl, heteroaryl, carboxyl group, amino group, alkylthio, sulfonic group, and alkoxy group; and wherein when any of R, R', and R" is a terminal functional group, then each terminal functional group R, R', and R" is independently selected from the group consisting of methoxyl, tertiary butyl, $N_3$, NCS, SH, $NH_2$, COOH, alkyne, N-Hydroxysuccinimide ester, maleimide, hydrazide, nitrone group, —CHO, —OH, halide, and charged ionic group.

In an embodiment, each D and D' is

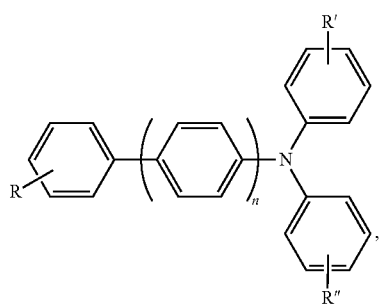, wherein n=0-2;
wherein each R, R', and R" is independently selected from the group consisting of: F, H, alkyl, unsaturated alkyl, heteroalkyl, heterocycloalkyl, aryl, heteroaryl, carboxyl group, amino group, alkylthio, sulfonic group, and alkoxy group; and wherein when any of each R, R', and R" is a terminal functional group, then each terminal functional group R, R', and R" is independently selected from the group consisting of methoxyl, tertiary butyl, $N_3$, NCS, SH, $NH_2$, COOH, alkyne, N-Hydroxysuccinimide ester, maleimide, hydrazide, nitrone group, —CHO, —OH, halide, and charged ionic group.

In an embodiment, the compound comprises a structure of:

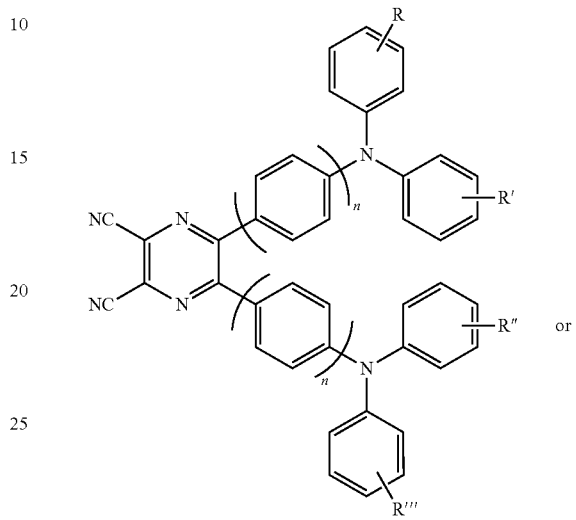 or

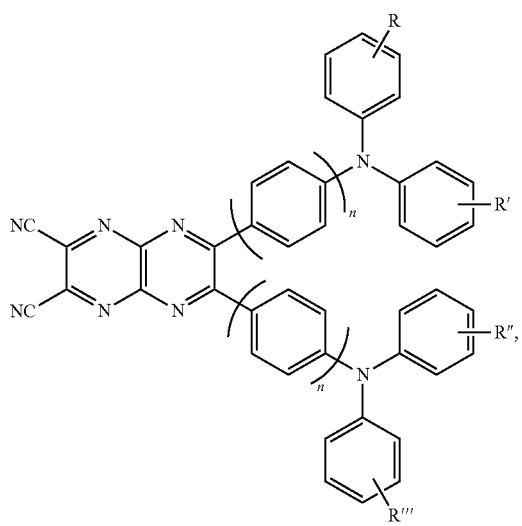, wherein n=1-3;
wherein each R, R', R", and R'" is independently selected from the group consisting of: F, H, alkyl, unsaturated alkyl, heteroalkyl, heterocycloalkyl, aryl, heteroaryl, carboxyl group, amino group, alkylthio, sulfonic group, and alkoxy group; and wherein when each R, R', and R" is a terminal functional group, then each R, R', and R" is independently selected from the group consisting of methoxyl, tertiary butyl, $N_3$, NCS, SH, $NH_2$, COOH, alkyne, N-Hydroxysuccinimide ester, maleimide, hydrazide, nitrone group, —CHO, —OH, halide, and charged ionic group.

In an embodiment, the compound is

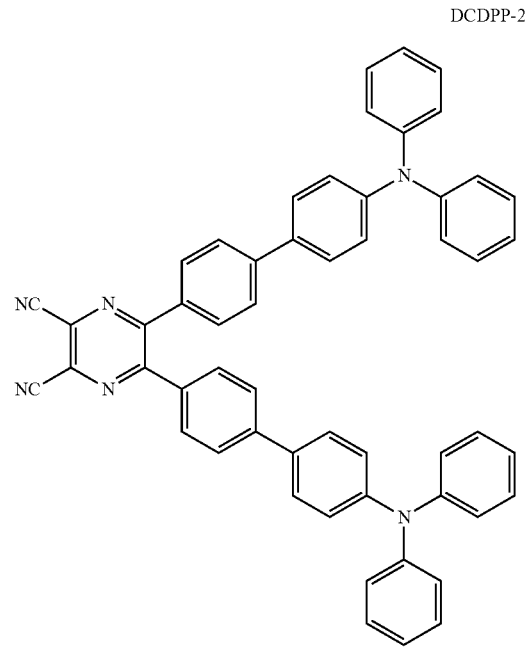

DCDPP-2TPA

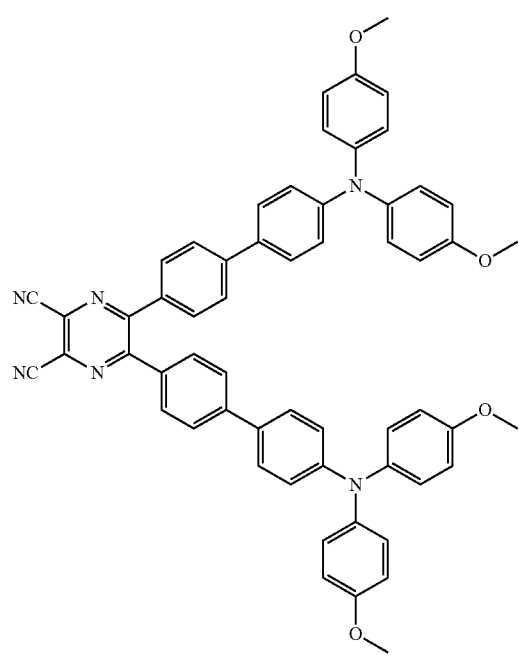

DCDPP-2TPA4M

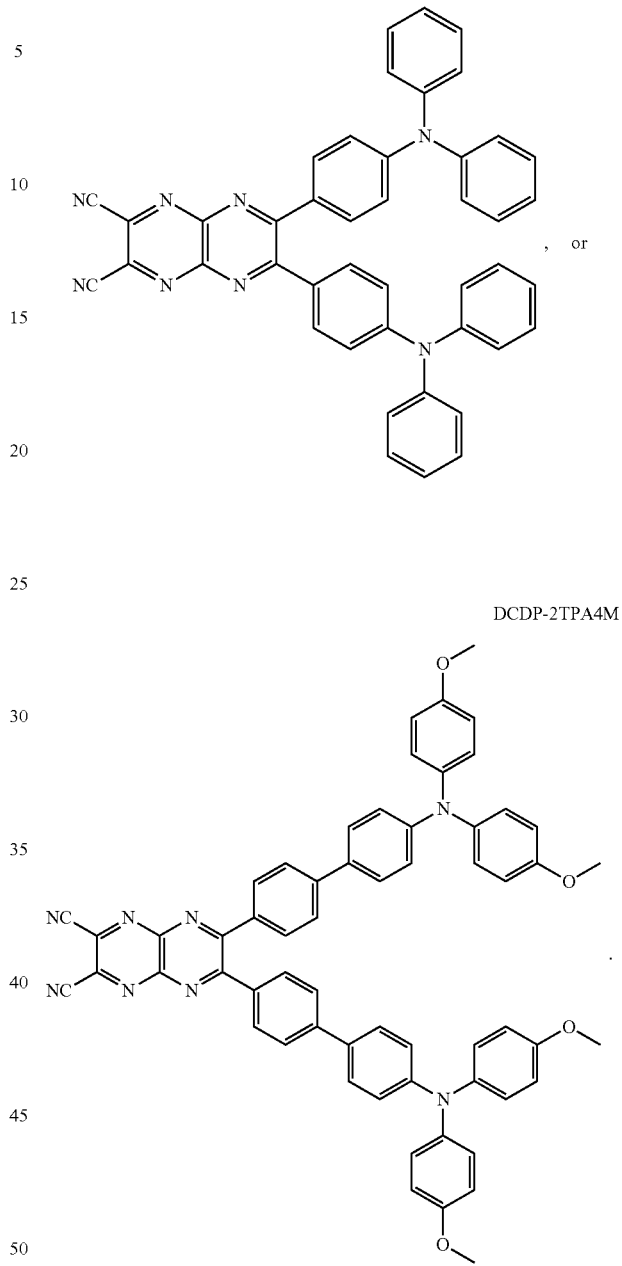

DCDP-2TPA

DCDP-2TPA4M

In an embodiment, the compound exhibits aggregation-induced emission (AIE).

In an embodiment, the present subject matter is directed to a probe comprising the present compound, wherein the probe is a red/near-infrared fluorescent probe. In an embodiment, the present compound is functionalized with special targeted groups to image biological species. In an embodiment, the present compound is fabricated in PEG/BSA and any amphiphilic molecule matrix, wherein the probe works in a form of nanoparticles. In an embodiment, the nanoparticles are incubated with cells or tissue and used for imaging cellular cytoplasms or tissue. In an embodiment, the nanoparticles are injected into a blood vessel and used for blood vessel imaging.

In an embodiment, the present compound is DTE-TPECM having a structure of

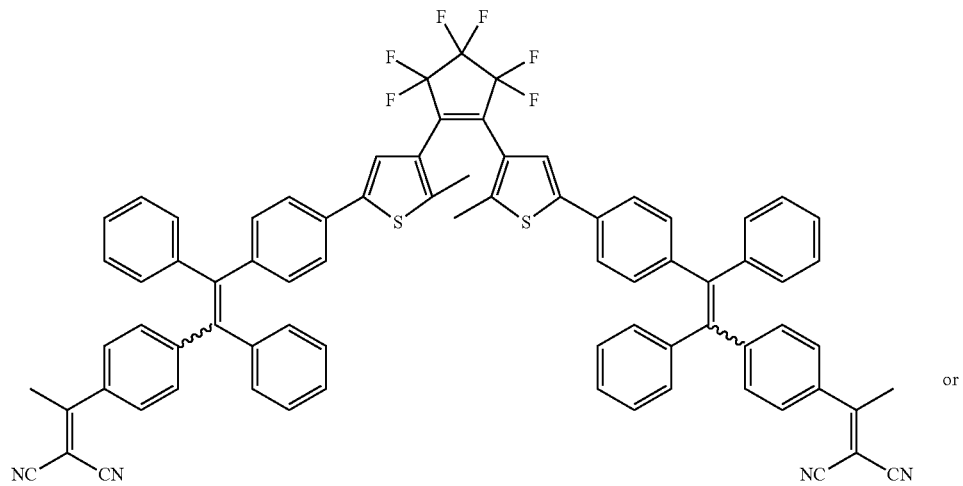

ROpen-DTE-TPECM

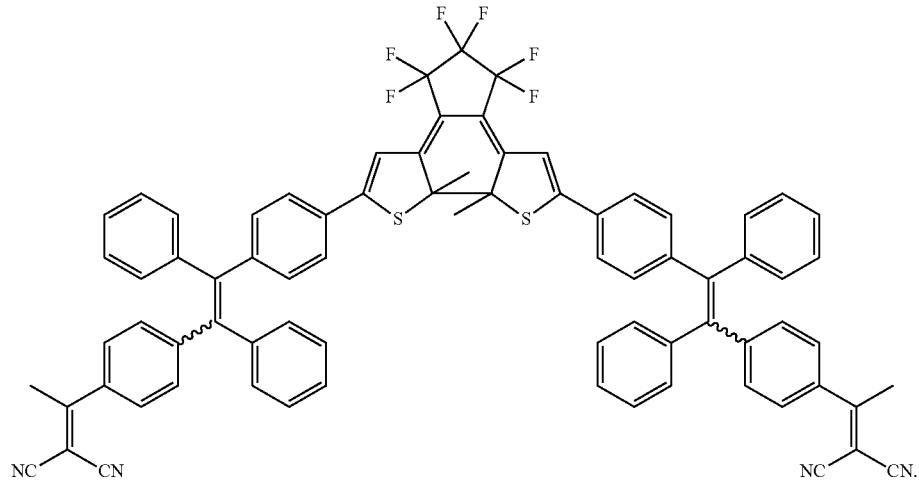

RClosed-DTE-TPECM

In an embodiment, the structure is ROpen-DTE-TPECM and the present compound exhibits AIE characteristics and is used for in vivo fluorescence imaging. In an embodiment, the structure is RClosed-DTE-TPECM and the present compound is used as a photoacoustic agent.

In an embodiment, the present subject matter is directed to a compound comprising a backbone structure selected from the group consisting of:

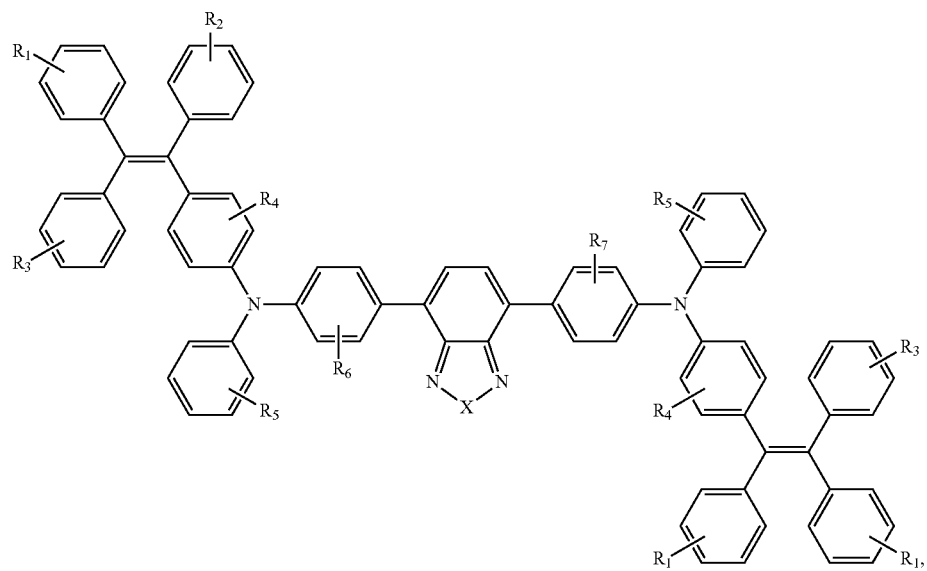
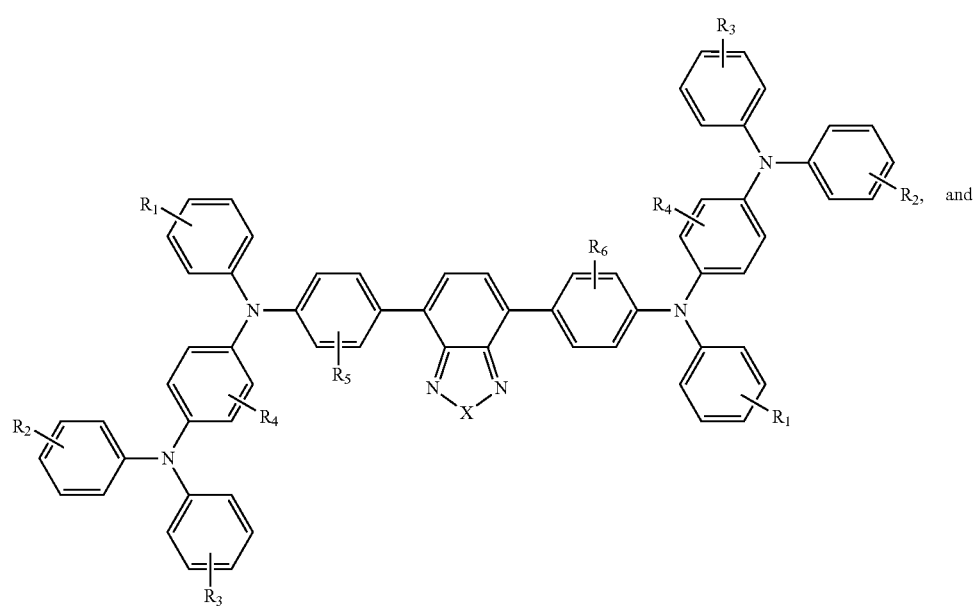

-continued

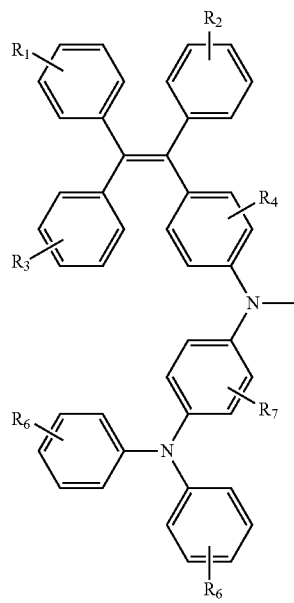 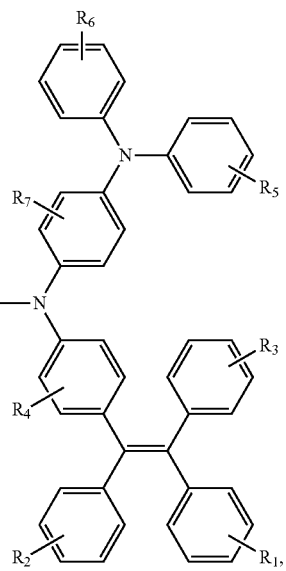

wherein each $R_1$, $R_2$, $R_3$, $R_4$, $R_5$, $R_6$, $R_7$, $R_8$, and $R_9$ may be substituted or unsubstituted and each $R_1$, $R_2$, $R_3$, $R_4$, $R_5$, $R_6$, $R_7$, $R_8$ and $R_9$ is independently selected from the group consisting of H, alkyl, unsaturated alkyl, heteroalkyl, cycloalkyl, heterocycloalkyl, aryl, heteroaryl, $C_mH_{2m+1}$, $C_{10}H_7$, $C_{12}H_9$, $OC_6H_5$, $OC_{10}H_7$, $OC_{12}H_9$, $C_mH_{2m}COOH$, $C_mH_{2m}NCS$, $C_mH_{2m}N_3$, $C_mH_{2m}NH_2$, $C_mH_{2m}SO_3$, $C_mH_{2m}Cl$, $C_mH_{2m}Br$, $C_mH_{2m}I$,

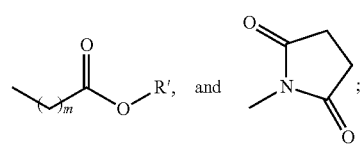

wherein m=0 to 20; and
wherein X is independently selected from S and Se.
In an embodiment, the present compound is TTS having a structure of:

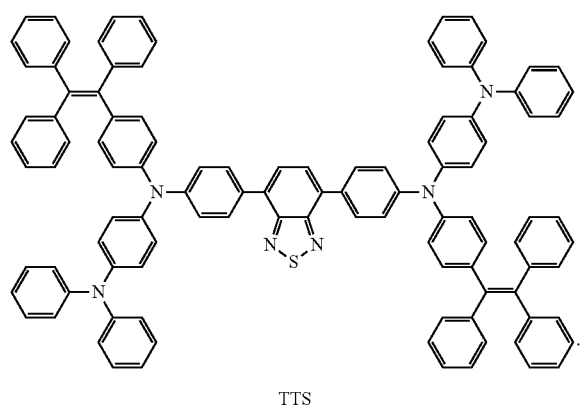 [SMILES: c1ccc(C(=C(c2ccccc2)c2ccc(N(c3ccc(-c4ccc(-c5ccc(N(c6ccc(C(=C(c7ccccc7)c7ccccc7)c7ccccc7)cc6)c6ccc(N(c7ccccc7)c7ccccc7)cc6)cc5)c5nsnc45)cc3)c3ccc(N(c4ccccc4)c4ccccc4)cc3)cc2)c2ccccc2)cc1 ; "TTS"]

TTS

In an embodiment, the present subject matter is directed to a probe comprising the present compound, wherein the probe is used for brain vascular imaging, sentinel lymph node mapping, and tumor imaging.

Far-Red/Near-Infrared AIE Luminogens for Biological Applications

In the present subject matter, far red/near-infrared donor-acceptor (D-A) type fluorescent probes with aggregation-induced emission (AIE) features have been developed and investigated. The photophysical properties (absorption and photoluminescence spectra) can be simply tuned by changing the electron donating or/and withdrawing property of the donor or/and acceptor units. These luminophores exhibit maximal luminescence peaks from the far red to the near-infrared (FR/NIR) spectral region (650-1000 nm), and high brightness in the solid state. In the solution state, these molecules are less emissive because the rotation of the aromatic rotors non-radiatively dissipates the exciton energy. While in the aggregate state, the emission of these AIEgens is induced or rejuvenated by the restriction of intramolecular motions (RIM) and the highly twisted molecular conformation that hampers the intermolecular π-π stacking interaction. These FR/NIR AIEgens are highly desirable for in-vivo biological applications due to the features of deep-tissue penetration, less photo-damage to the body, and high signal-to-noise ratio of FR/NIR light. Primary experiments indicate that these FR/NIR dyes are excellent candidates for biology-related applications.

Figure 8:
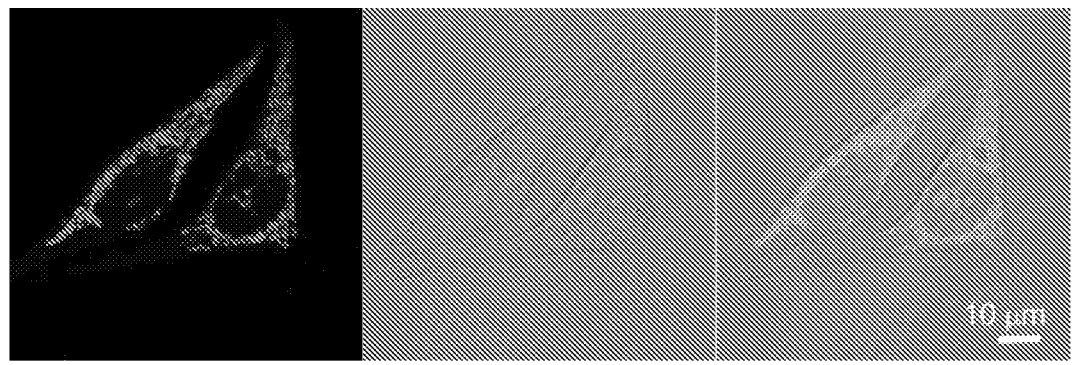
FIG. 8 shows bright-field, fluorescent, and merged image of living HeLa cells incubated with MTPE-TP dots for 12 h at 37° C. $\lambda_{ex}$: 514 nm.
Figure 9:
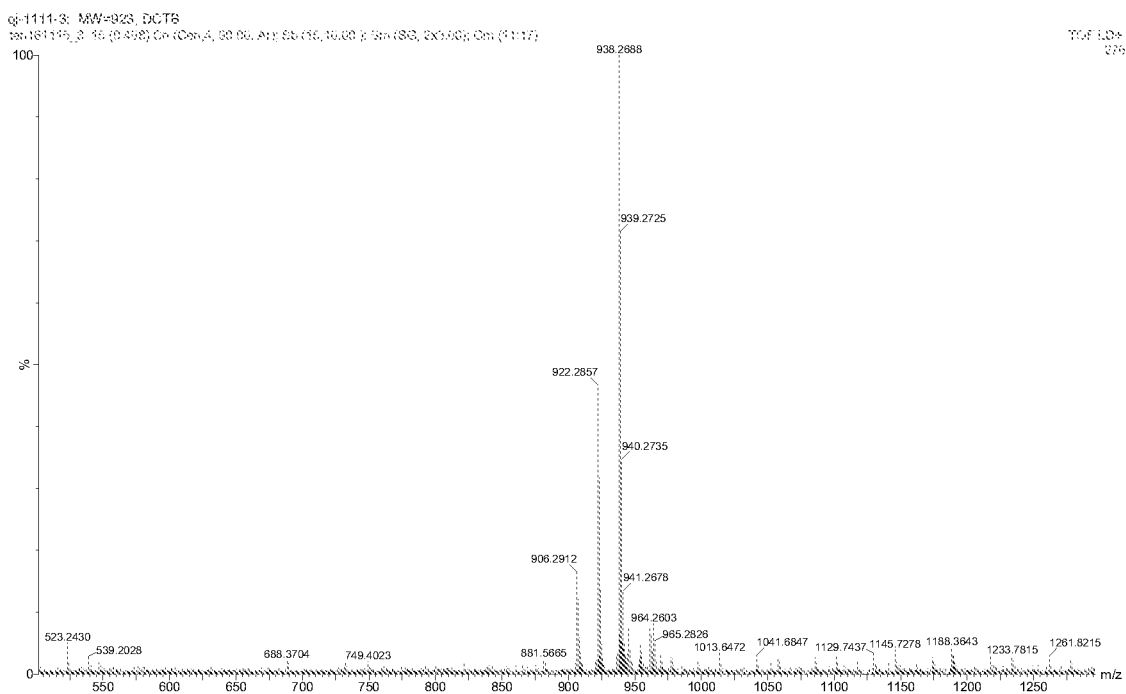
FIG. 9 shows mass spectrum of MTPE-TT.
Figure 10:
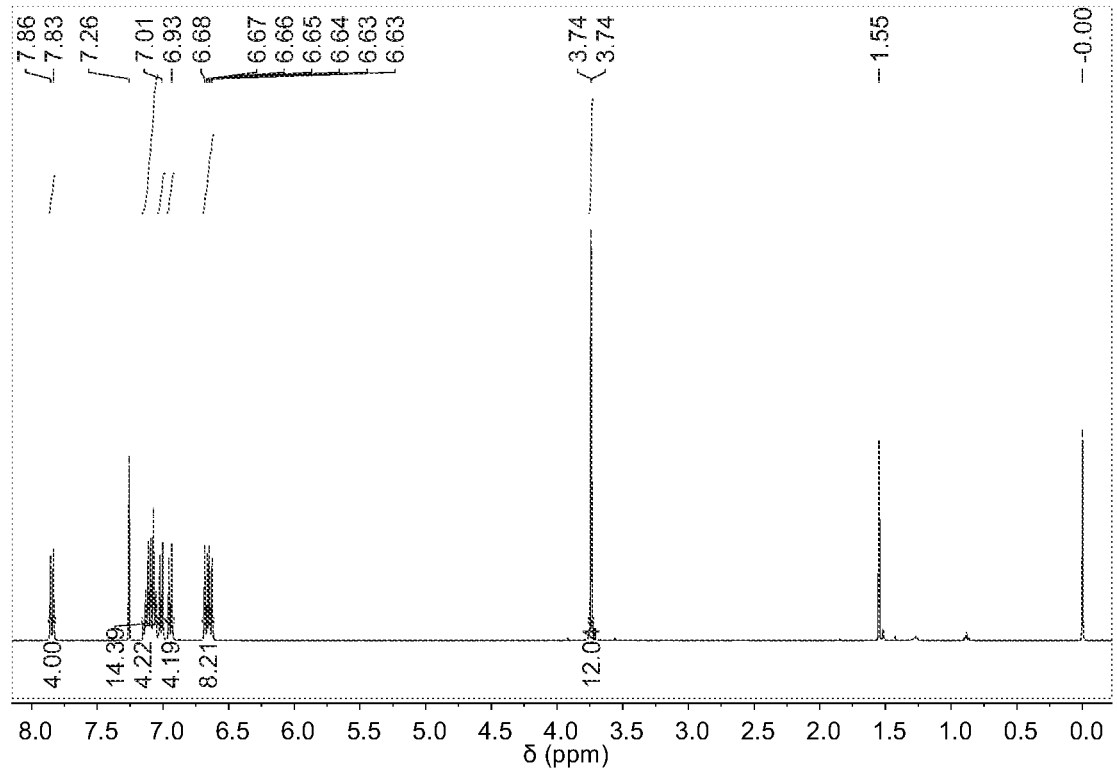
FIG. 10 shows $^1$H-NMR spectrum of MTPE-TT in $CDCl_3$.
Figure 11:
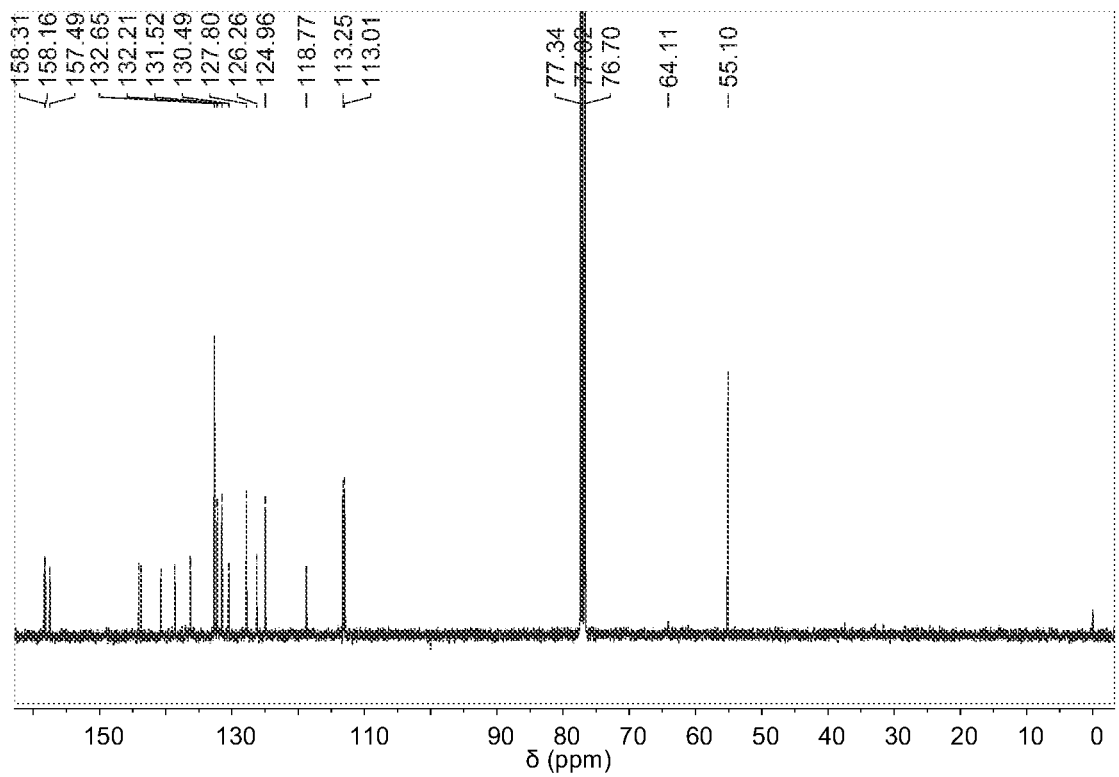
FIG. 11 shows $^{13}$C-NMR spectrum of MTPE-TT in $CDCl_3$.
Figure 12:
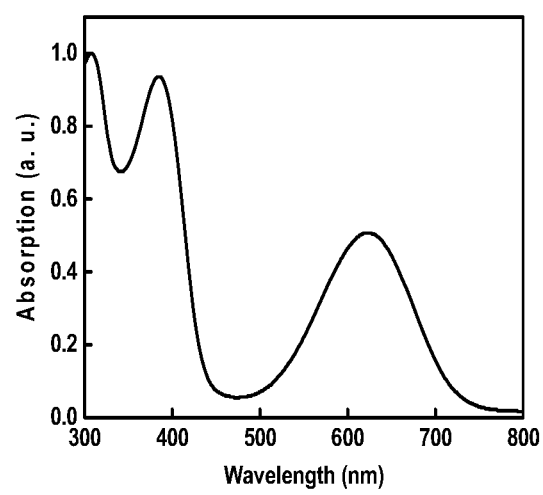
FIG. 12 shows absorption spectrum of MTPE-TT in DMSO.
Figure 28:
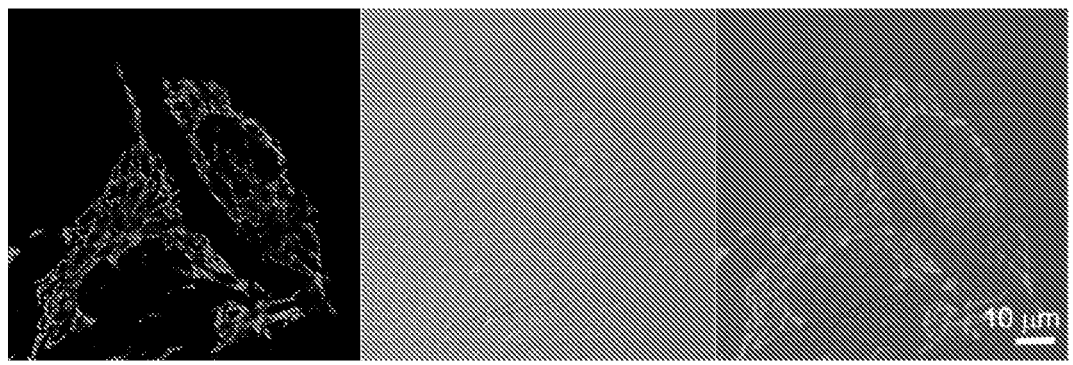
FIG. 28 shows bright-field, fluorescent, and merged image of living HeLa cells incubated with PTZ-BT-TPA dots for 12 h at 37° C. $\lambda_{ex}$: 489 nm.
Figure 29:
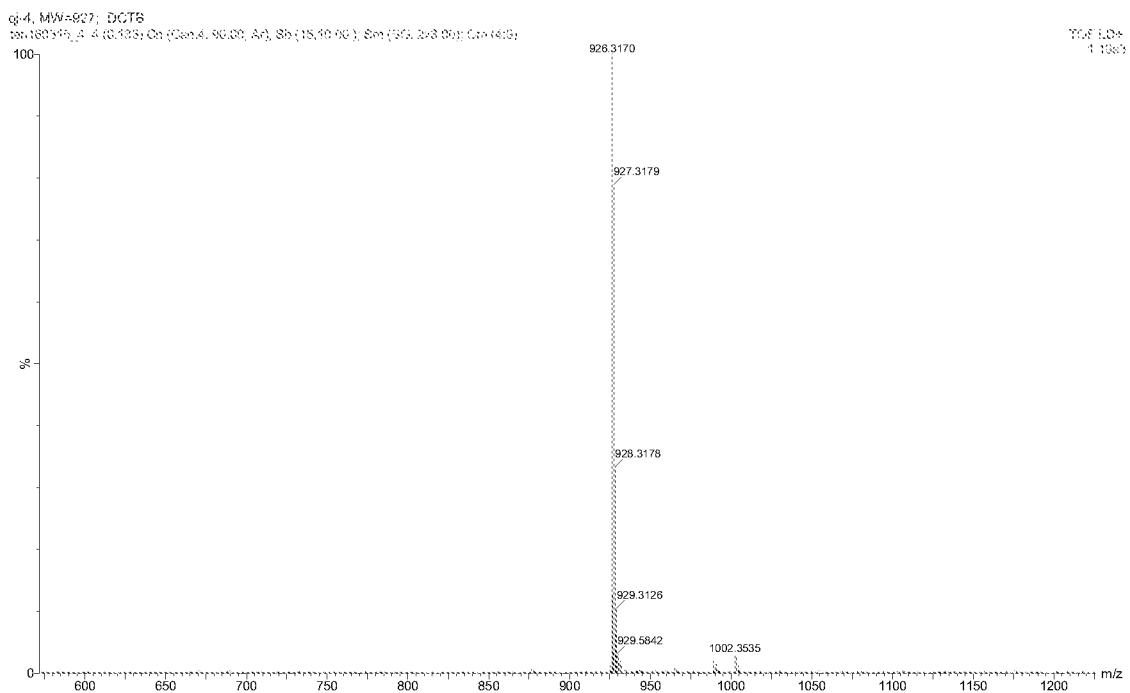
FIG. 29 shows mass spectrum of NPB-TQ.
Figure 30:
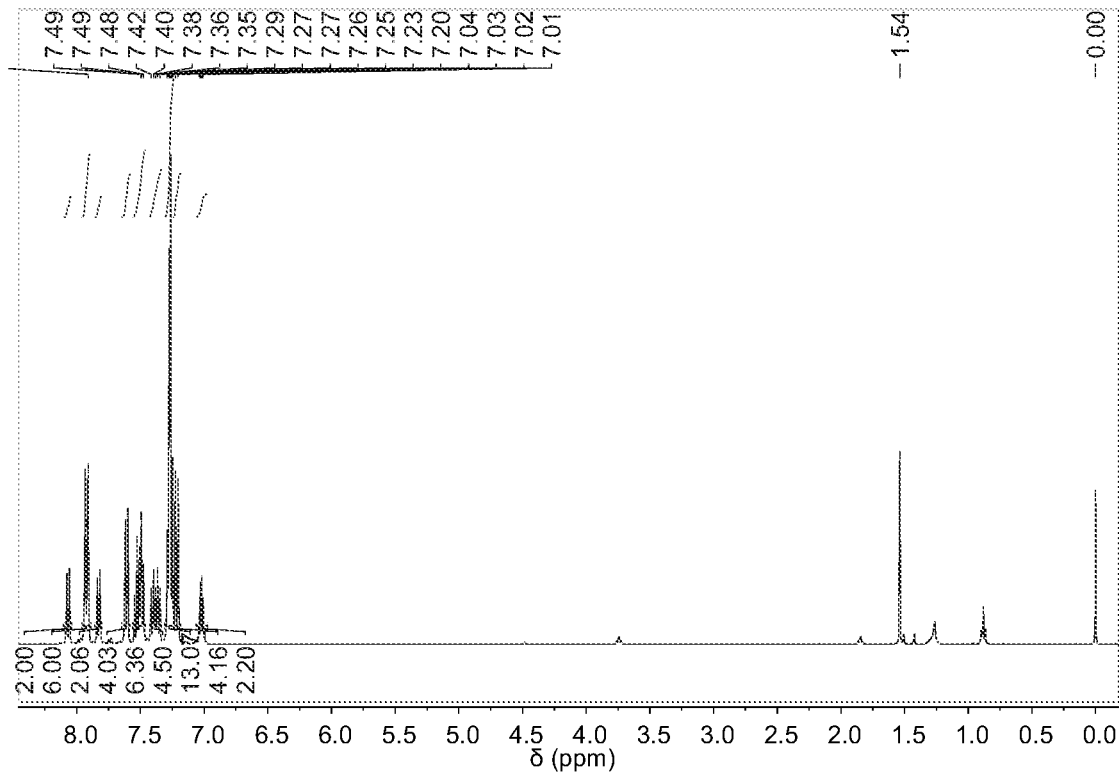
FIG. 30 shows $^1$H-NMR spectrum of NPB-TQ in $CDCl_3$.
Figure 31:
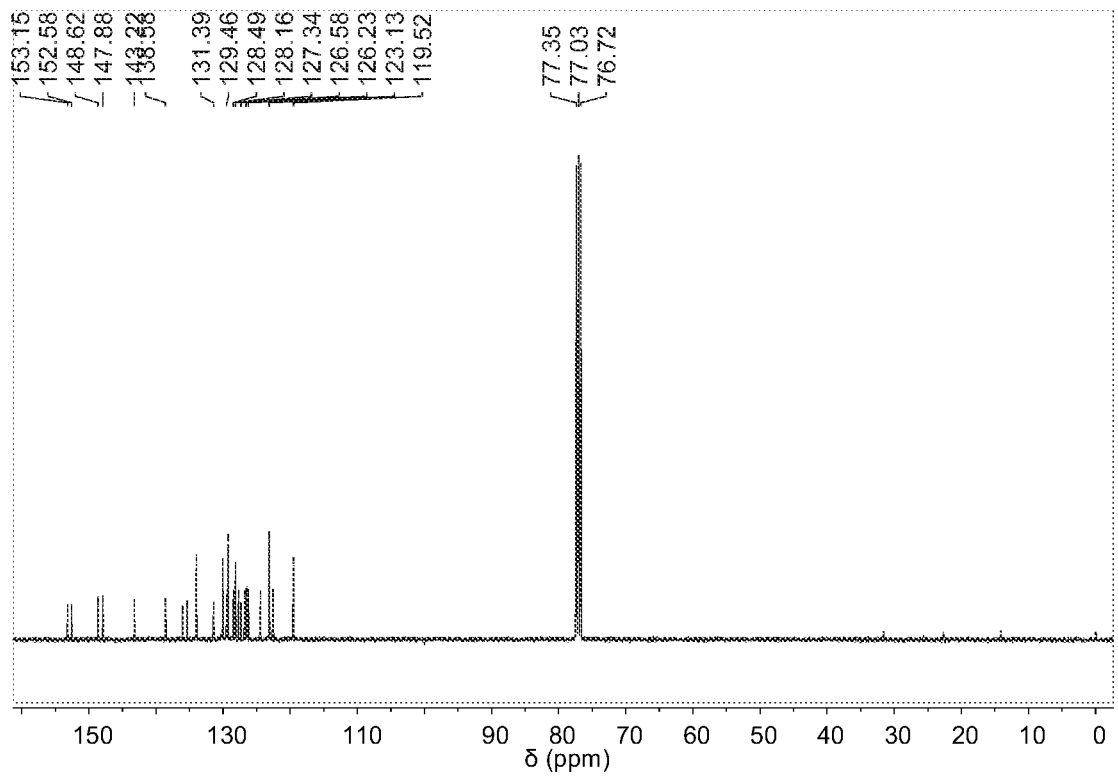
FIG. 31 shows $^{13}$C-NMR spectrum of NPB-TQ in $CDCl_3$.
Figure 32:
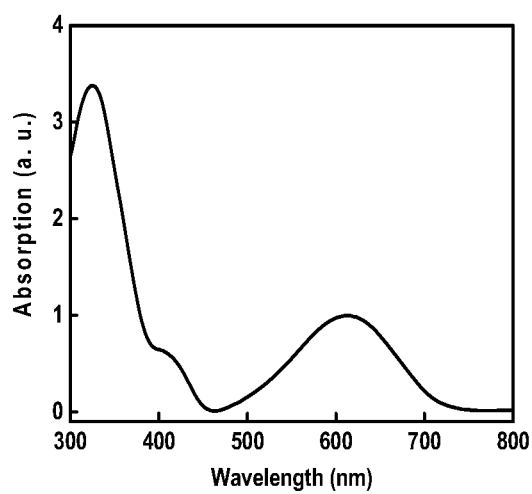
FIG. 32 shows absorption spectrum of NPB-TQ in THF.
Figure 33:
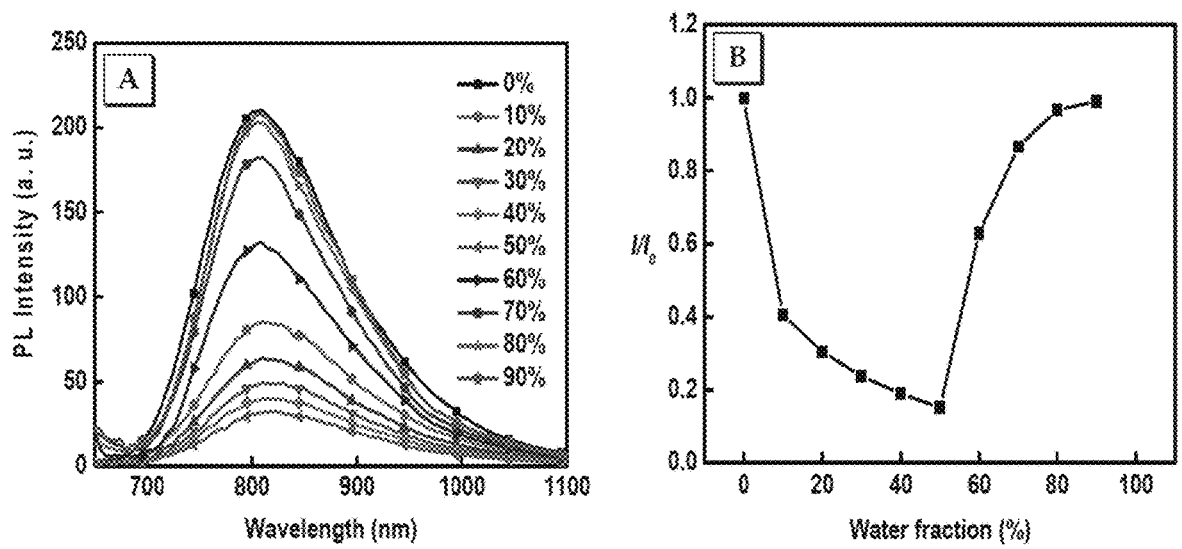
FIG. 33 shows (A) photoluminescence (PL) spectra of NPB-TQ in THF and THF/water mixtures with increasing water fractions (fw) from 10% to 90%. (B) Change in PL intensity of NPB-TQ versus water fraction in THF/water mixtures. Excitation at 610 nm.
Figure 34:
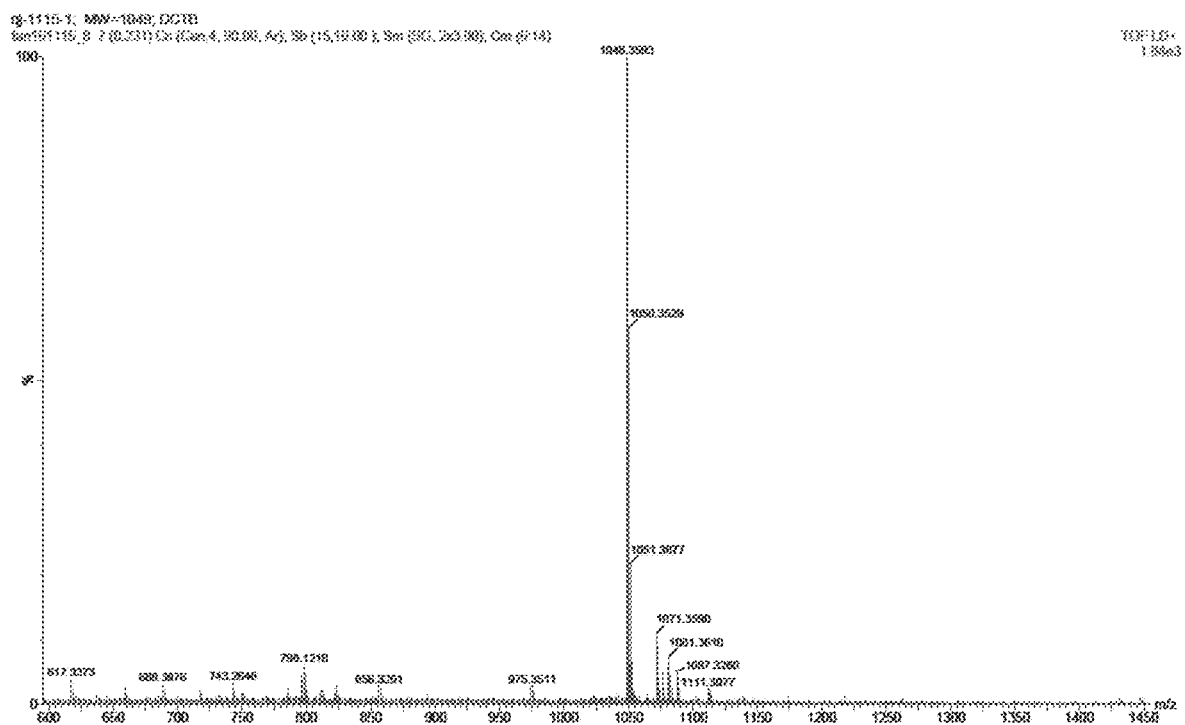
FIG. 34 shows mass spectrum of TPE-TQ-A.
Figure 35:
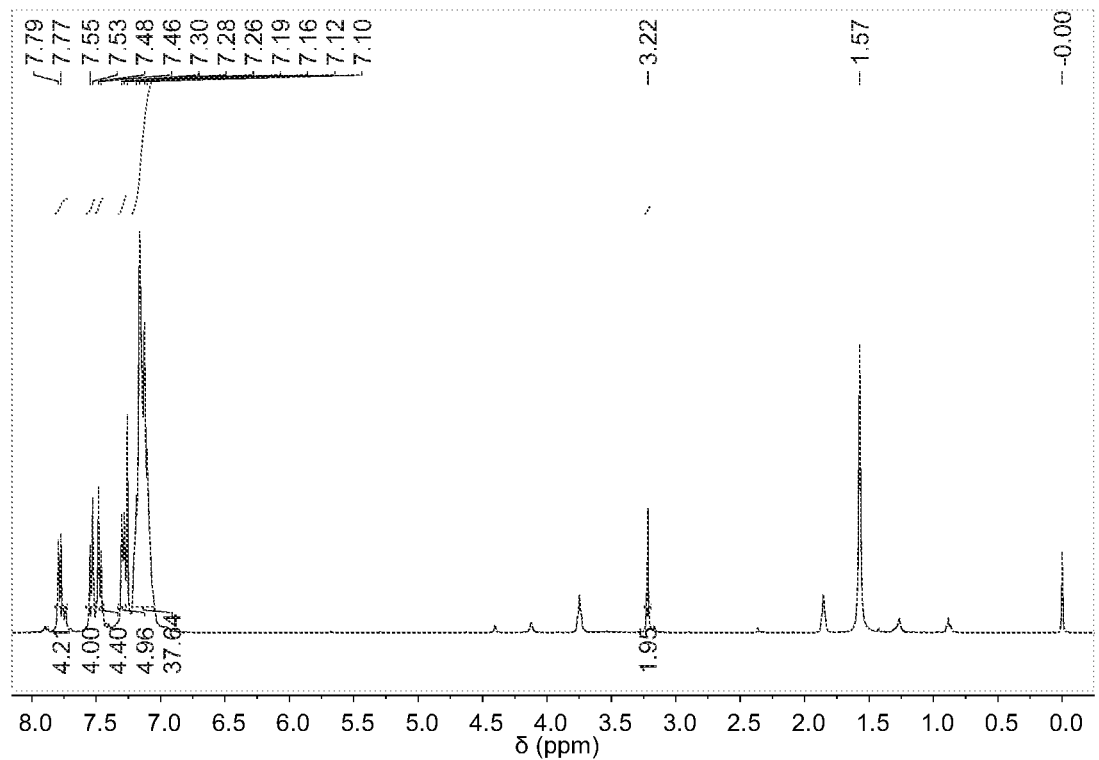
FIG. 35 shows $^1$H-NMR spectrum of TPE-TQ-A in $CDCl_3$.
Figure 36:
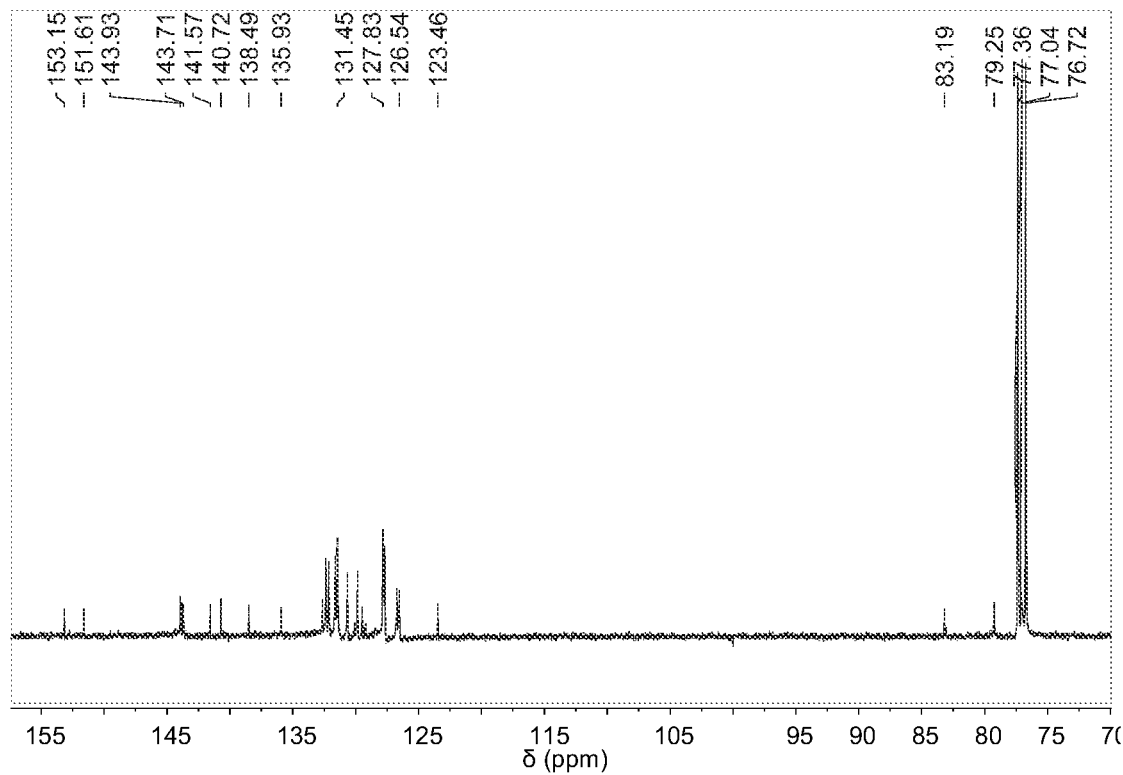
FIG. 36 shows $^{13}$C-NMR spectrum of TPE-TQ-A in $CDCl_3$.
Figure 37:
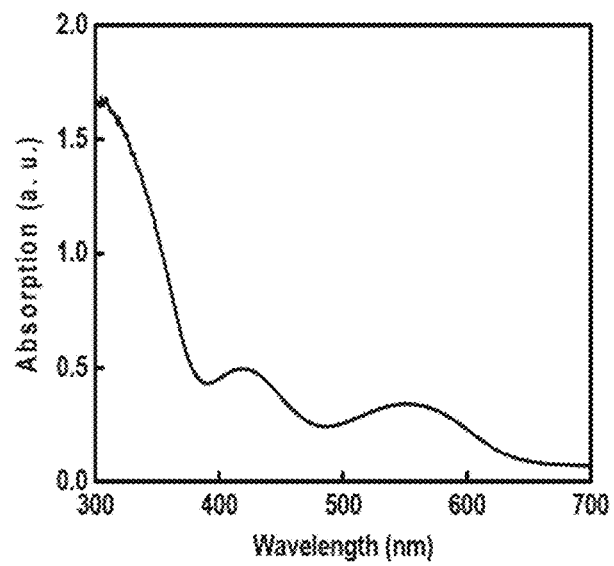
FIG. 37 shows absorption spectrum of TPE-TQ-A in THF.
Figure 38:
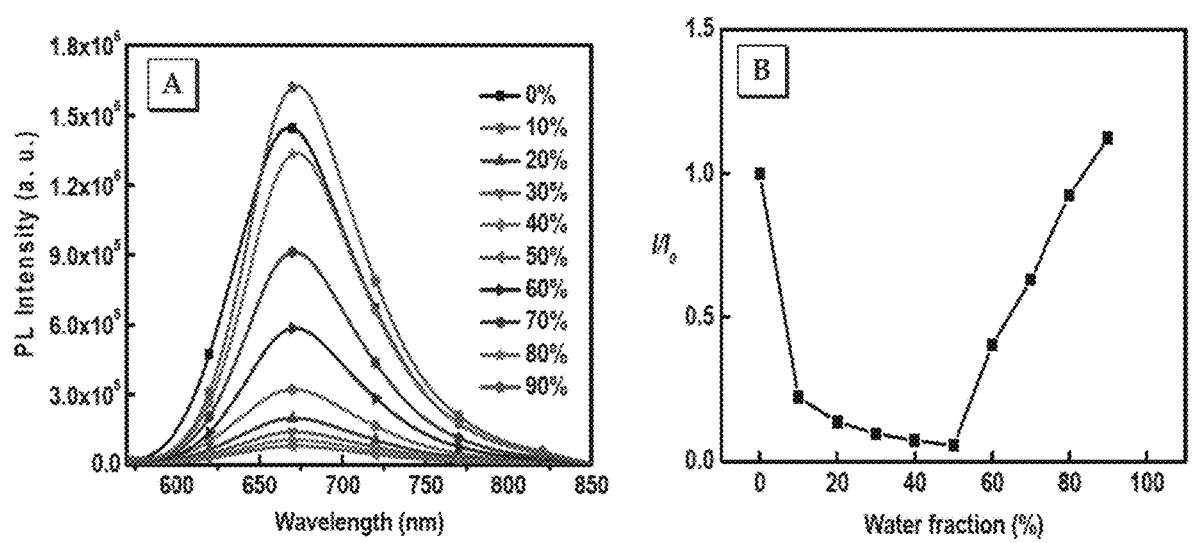
FIG. 38 shows (A) photoluminescence (PL) spectra of TPE-TQ-A in THF and THF/water mixtures with increasing water fractions (fw) from 10% to 90%. (B) Change in PL intensity of TPE-TQ-A versus water fraction in THF/water mixtures. Excitation at 530 nm.
Figure 39:
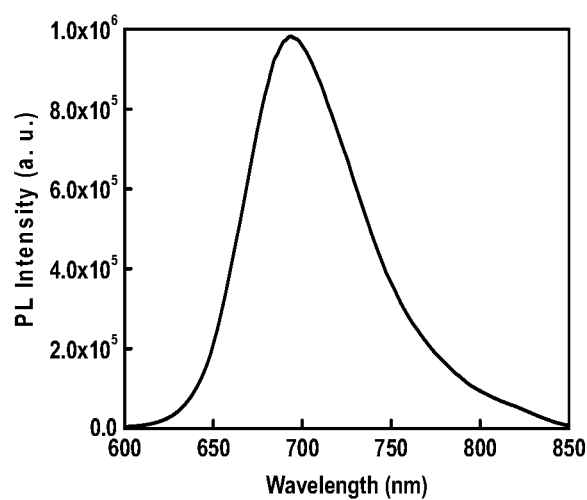
FIG. 39 shows photoluminescence (PL) spectrum of TPE-TQ-A in the solid state.
Figure 40:
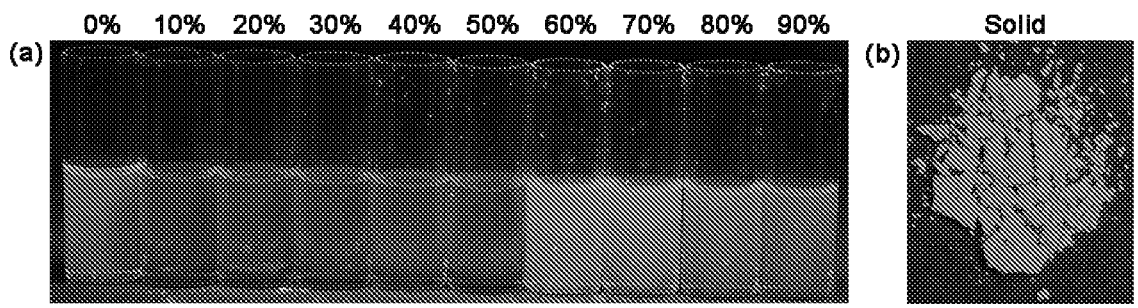
FIG. 40 shows photographs of (a) TPE-TQ-A in THF and THF/water mixtures with increasing water fractions (fw) from 10% to 90%, and (b) the solid sample taken under 365 nm UV-light illumination.
Figure 41:
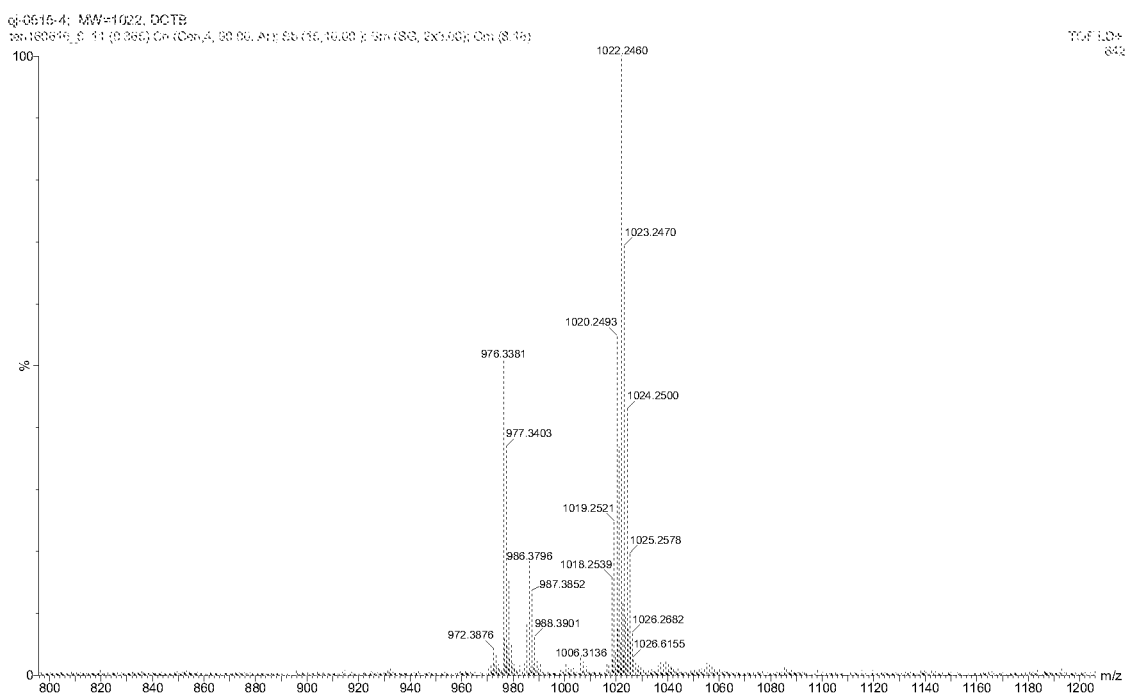
FIG. 41 shows mass spectrum of MTPE-BTSe.
Figure 42:
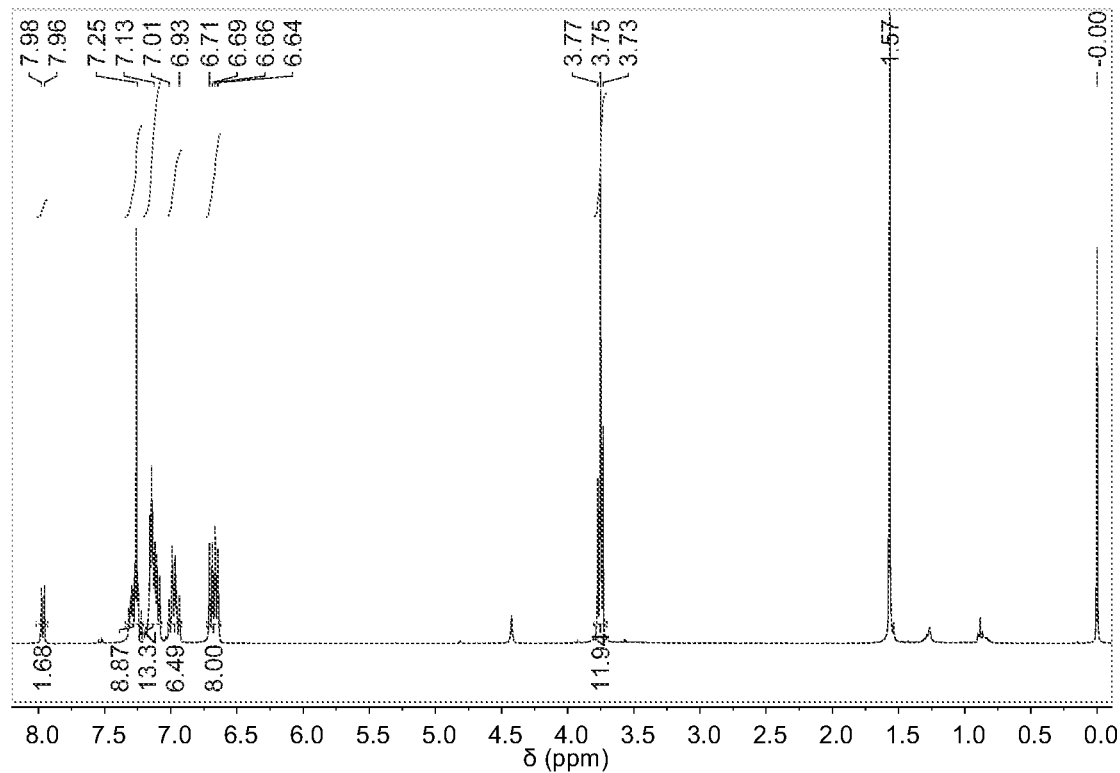
FIG. 42 shows $^1$H-NMR spectrum of MTPE-BTSe in $CDCl_3$.
Figure 43:
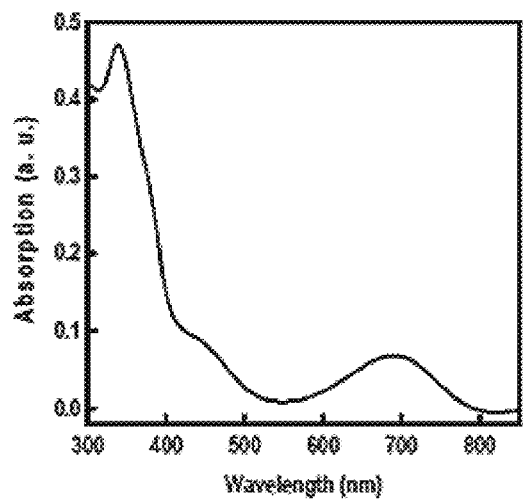
FIG. 43 shows absorption spectrum of MTPE-BTSe in THF.
Figure 44:
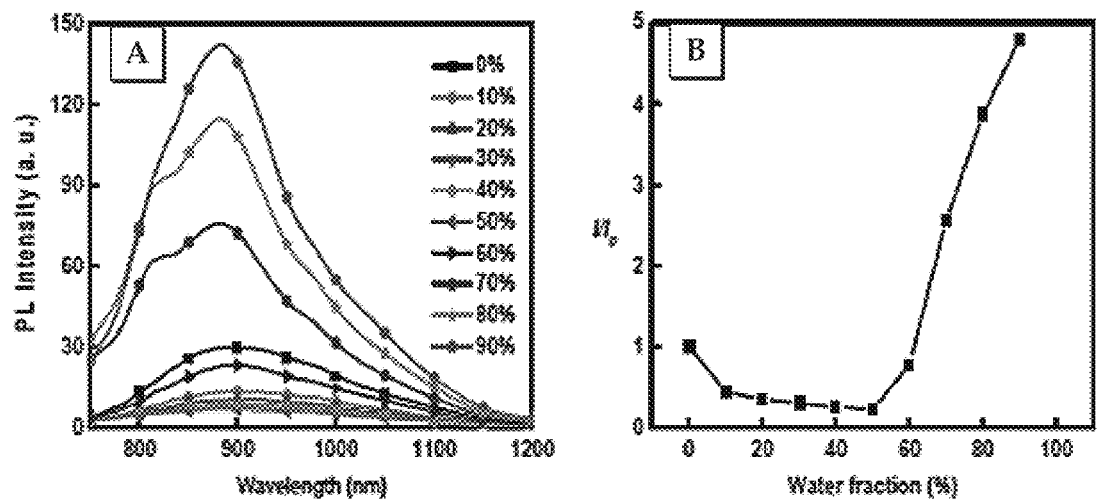
FIG. 44 shows (A) photoluminescence (PL) spectra of MTPE-BTSe in THF and THF/water mixtures with increasing water fractions (fw) from 10% to 90%. (B) Change in PL intensity of MTPE-BTSe versus water fraction in THF/water mixtures. Excitation at 690 nm.
Figure 45:
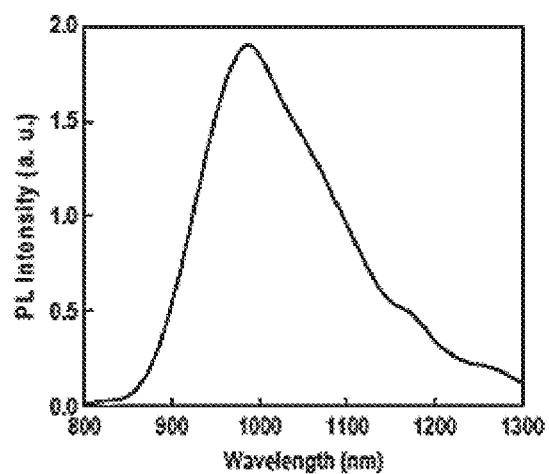
FIG. 45 shows photoluminescence (PL) spectrum of MTPE-BTSe in the solid state.
Figure 46:
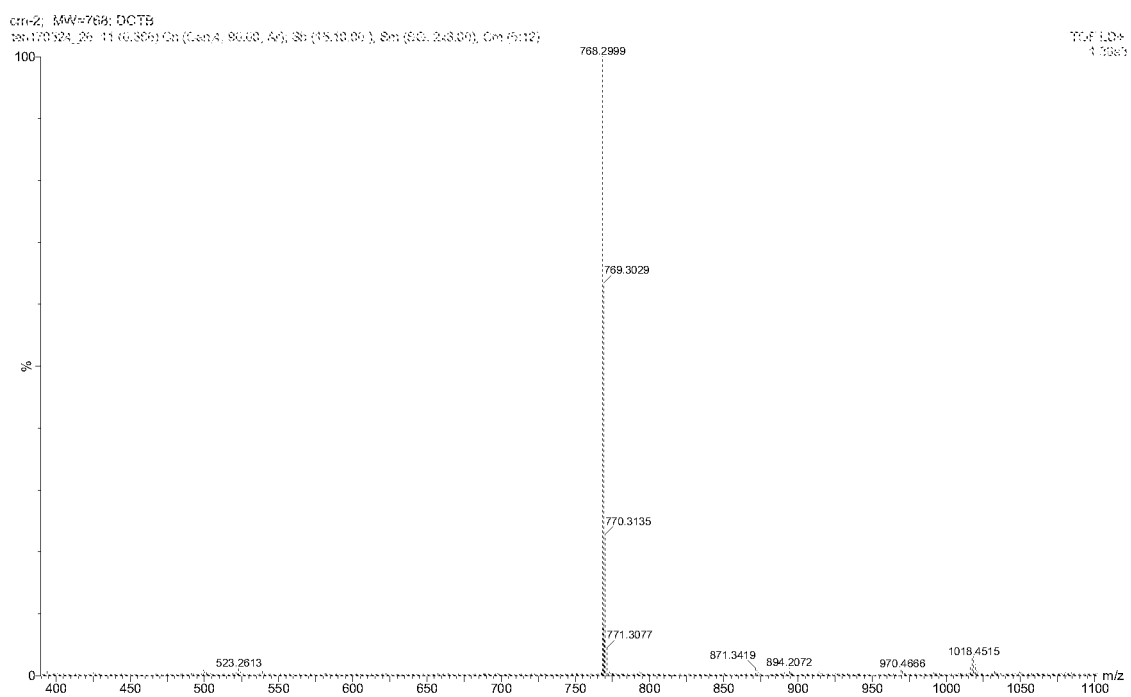
FIG. 46 shows HRMS of DCDPP-2TPA.
Figure 47:
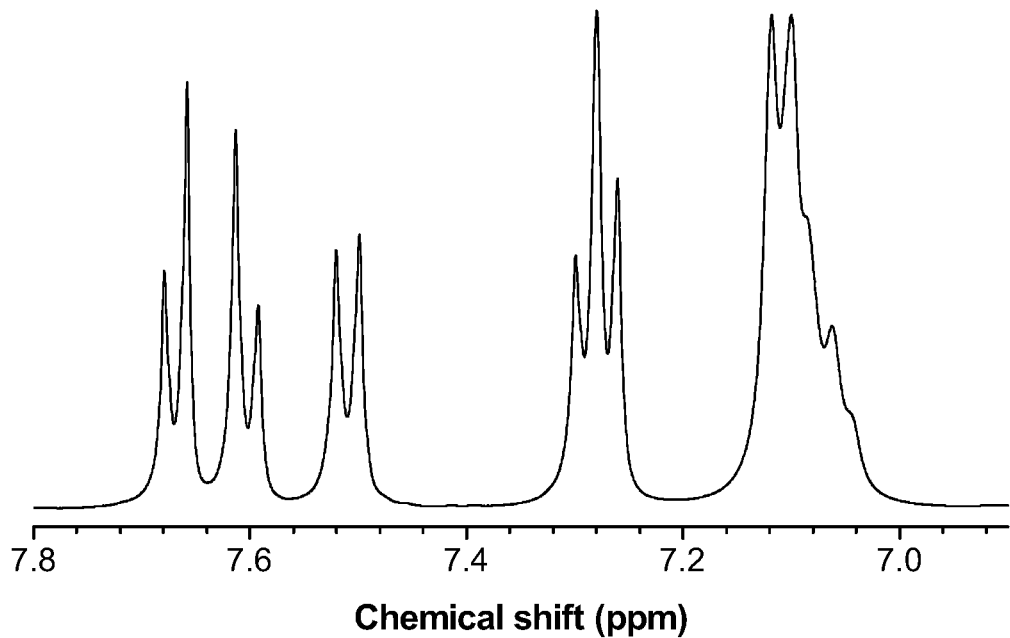
FIG. 47 shows $^1$H NMR spectrum of DCDPP-2TPA in $CD_2Cl_2$.
Figure 48:
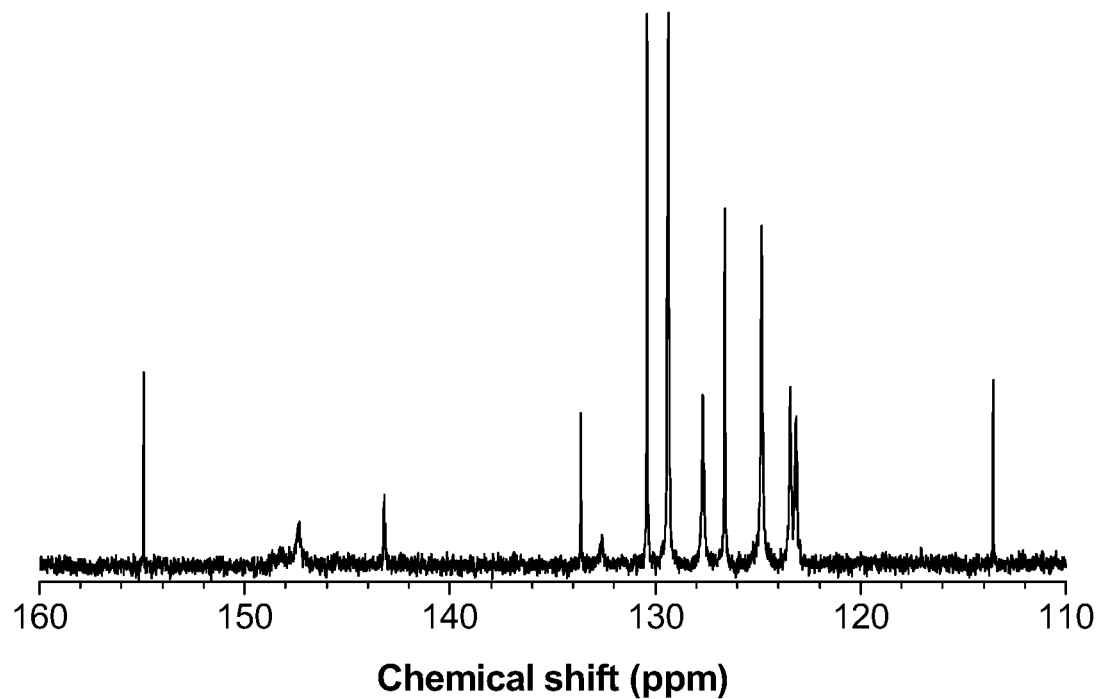
FIG. 48 shows $^{13}$C NMR spectrum of DCDPP-2TPA in $CD_2Cl_2$.
Figure 49:
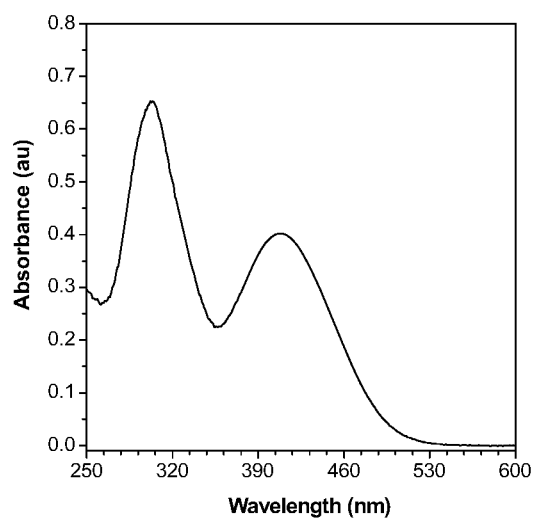
FIG. 49 shows UV-vis spectrum of DCDPP-2TPA in THF.
Figure 50:
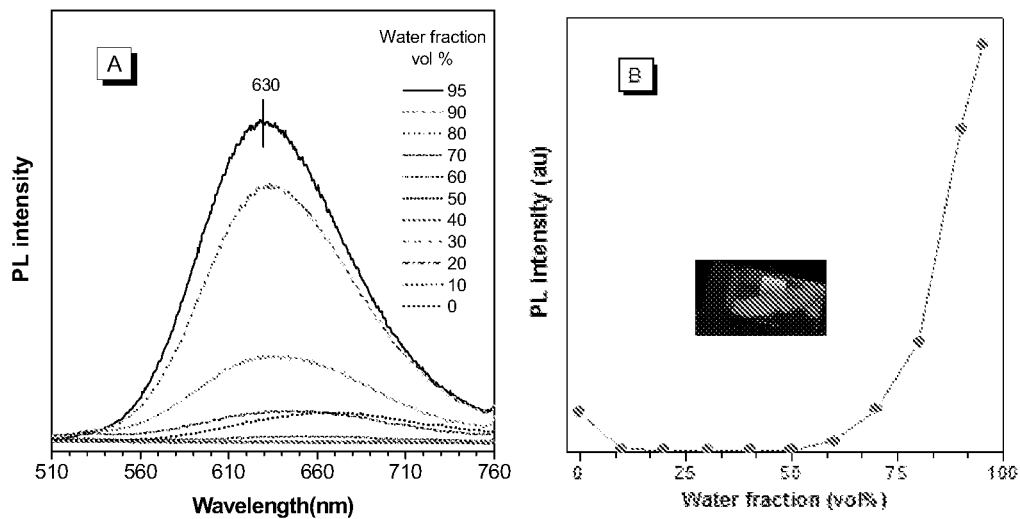
FIG. 50 shows (A) PL spectra of DCDPP-2TPA in THF/water mixtures with different water contents, concentration is $10^{-5}$ M, $\lambda_{ex}$=408 nm; (B) PL intensities of DCDPP-2TPA in THF/water mixtures with different water contents, insert: Photographs of the powder of DCP-2TPA taken under 365 nm UV light.
Figure 51:
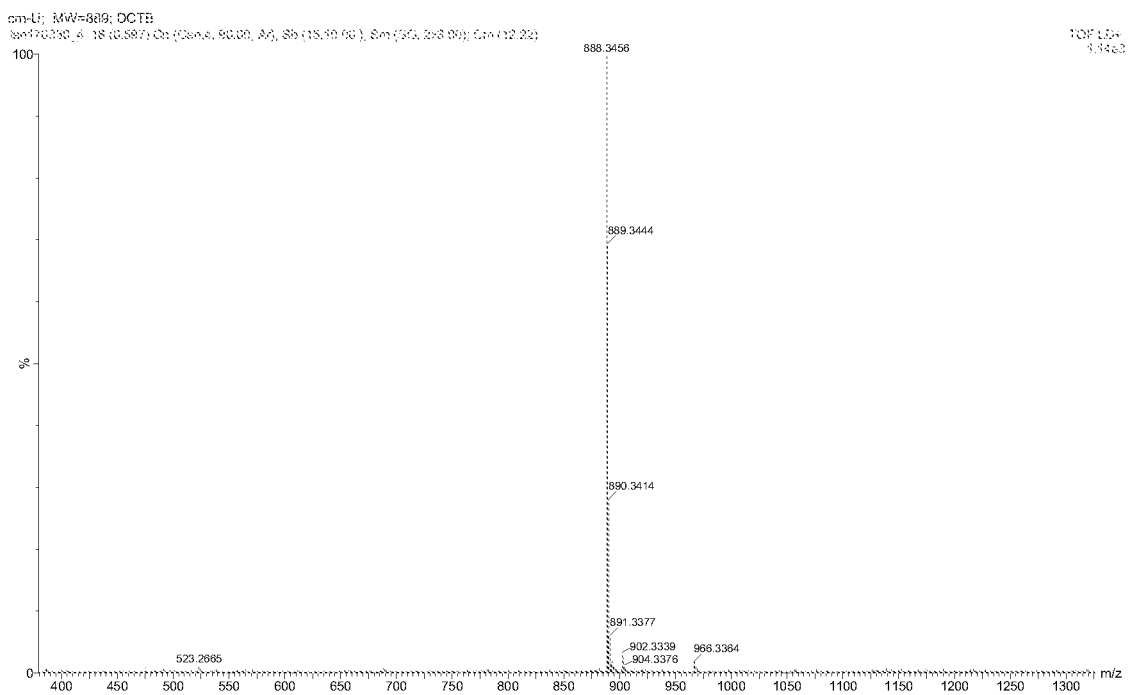
FIG. 51 shows HRMS of DCDPP-2TPA4M.
Figure 52:
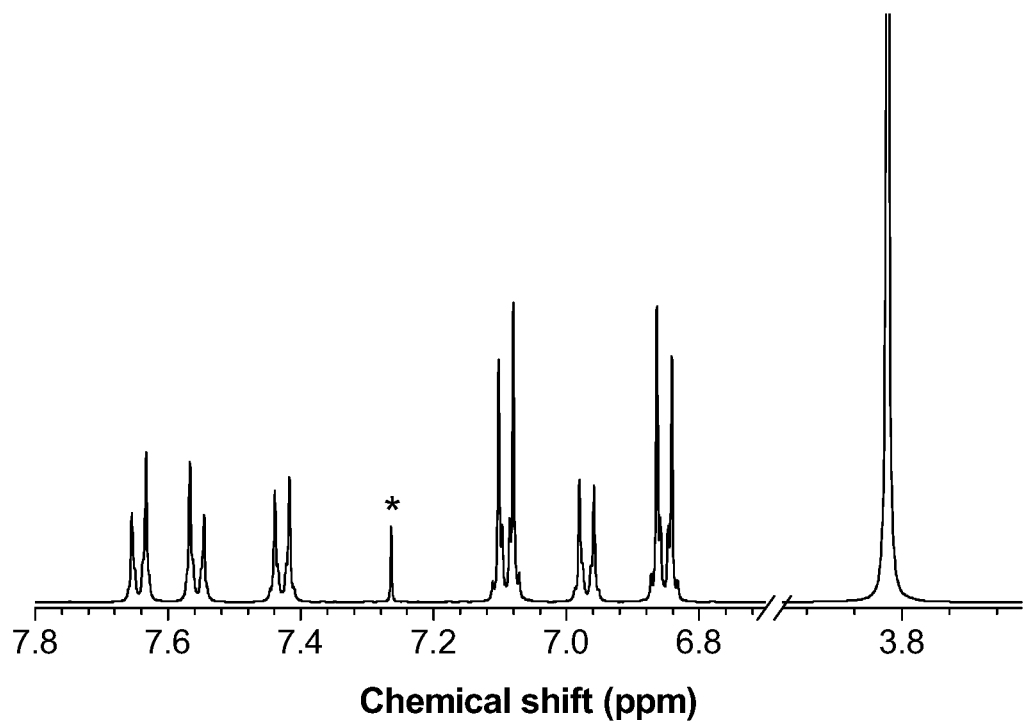
FIG. 52 shows $^1$H NMR spectrum of DCDPP-2TPA4M in $CDCl_3$.
Figure 53:
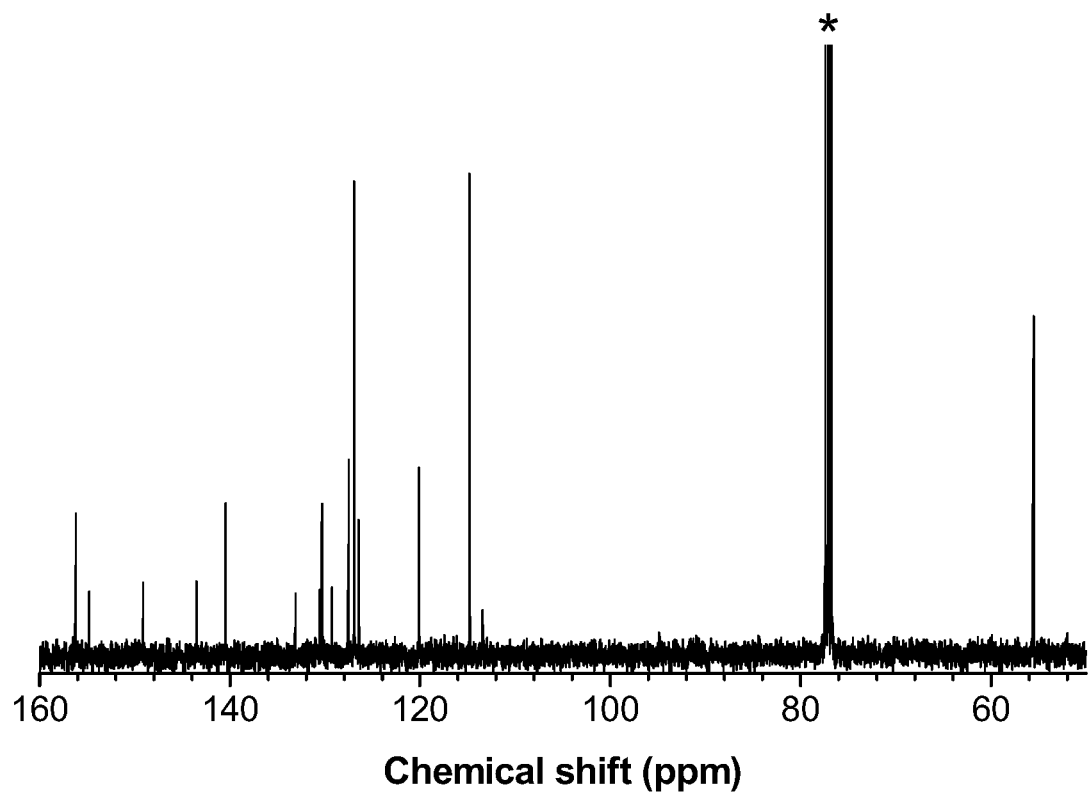
FIG. 53 shows $^{13}$C NMR spectrum of DCDPP-2TPA4M in $CDCl_3$.
Figure 54:
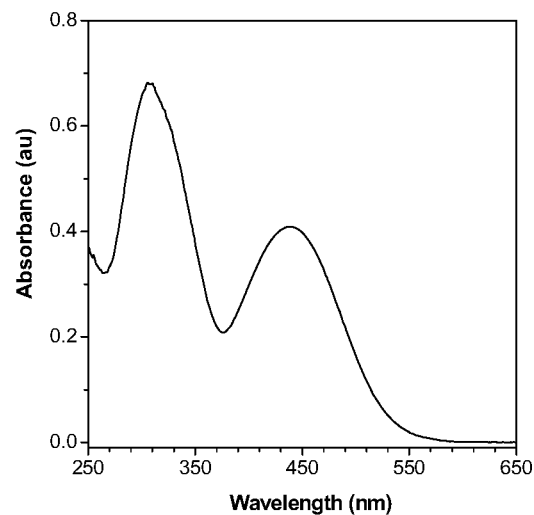
FIG. 54 shows UV-vis spectrum of DCDPP-2TPA4M in THF.

For example, dyes MTPE-TP and PTZ-BT-TPA have been tested in living HeLa cells in order to analyze their use as biosensors for bioimaging. The dye and an amphiphilic polymer were used to fabricate fluorescent dots, and the dots can accumulate preferentially in tumors through the enhanced permeability and retention (EPR) effect. As shown in FIGS. 8 and 28, an intense red fluorescence was observed in the cellular cytoplasms, demonstrating the great potential of AIE dots as an FR/NIR fluorescent probe for biological imaging. Some strong donor-acceptor systems (e.g., PTZ-BT-TPA, TPE-TPA-TT, and NPB-TQ) exhibit excellent two-photon absorption properties, which demonstrate their application for two-photon and multiphoton fluorescence imaging.

In addition, by the introduction of special functional and targeted groups in the AIEgens, the dyes can be used for specific targeting of biological species. For example, there are two alkyne groups in the AIE dye TPE-TQ-A, which is convenient for further introduction of functional or targeted groups through click reaction.

Characterization $^1$H and $^{13}$C NMR spectra were measured on a Bruker ARX 400 NMR spectrometer using chloroform as solvent and tetramethylsilane (TMS, δ=0) as internal reference. High-resolution mass spectra (HRMS) were recorded on a Finnigan MAT TSQ 7000 Mass Spectrometer System operated in a MALDI-TOF mode. Absorption spectra were recorded on a Shimadzu UV-3600 spectrophotometer. Steady-state fluorescence spectra were recorded on a Perkin Elmer LS 55 spectrometer or a HORIBA Spectrofluorometer. Laser confocal scanning microscope images were collected on Zeiss laser scanning confocal microscope (LSM7 DUO) and analyzed using ZEN 2009 software (Carl Zeiss).

Fabrication of AIE Dots

Generally, 1 mg of the AIEgen and 5 mg of DSPE-PEG-Biotin were dissolved in 1 mL of chloroform. Subsequently, 9 mL of Milli-Q water was added into the chloroform solution under sonication for 10 minutes at room temperature using a microtip probe sonicator with an 18 W output (XL2000, Misonix Incorp., USA). The mixture was stirred in the nitrogen flow overnight until the chloroform was completely evaporated. A clear solution was obtained, and the solution was filtered through a 0.45 μm microfilter to result in the formation of AIE dots.

Cell Culture and Staining

Cell Culture: HeLa cells were cultured in MEM containing 10% FBS and antibiotics (100 units/mL penicillin and 100 g/mL streptomycin) in a 5% $CO_2$ humidity incubator at 37° C. All culture media were supplemented with 10% heat-inactivated FBS, 100 units/mL penicillin, and 100 μg/mL streptomycin. Before the experiment, the cells were precultured until confluence was reached.

Cell Imaging: HeLa cells were grown overnight on a 35 mm petri dish with a cover slip at 37° C. After removal of the medium, the adherent cells were washed twice with 1× phosphate buffered saline (PBS) buffer. The AIE dots were then added to the chamber. After incubation for 12 hours, the cells were washed three times with 1×PBS buffer. The cells were imaged on a Zeiss laser scanning confocal microscope and analyzed using ZEN 2009 software.

AIE Study

Figure 5:
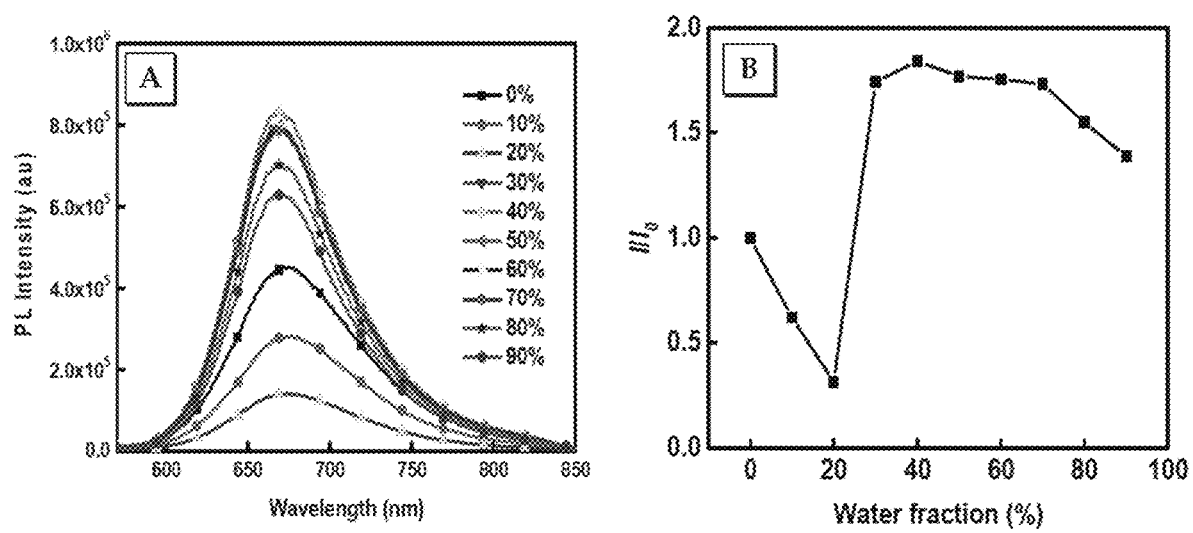
FIG. 5 shows (A) photoluminescence (PL) spectra of MTPE-TP in DMSO and DMSO/water mixtures with increasing water fractions (fw) from 10% to 90%. (B) Change in PL intensity of MTPE-TP versus water fraction in DMSO/water mixtures. Excitation at 530 nm.
Figure 6:
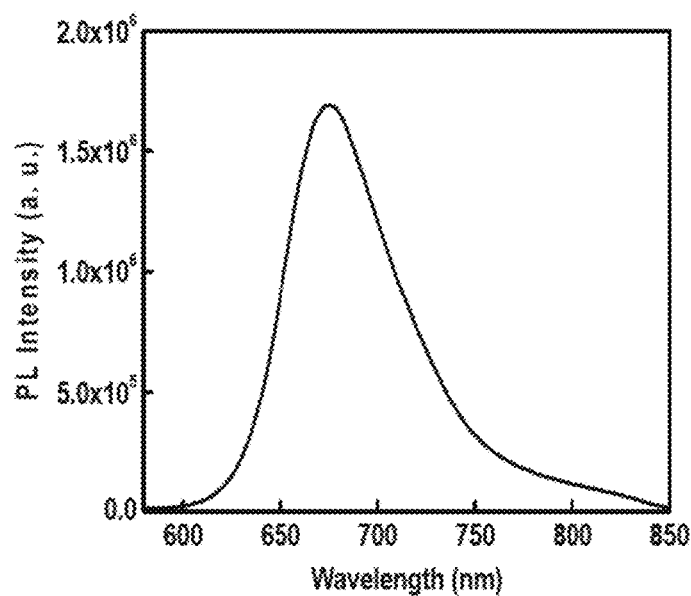
FIG. 6 shows photoluminescence (PL) spectrum of MTPE-TP in the solid state.
Figure 7:
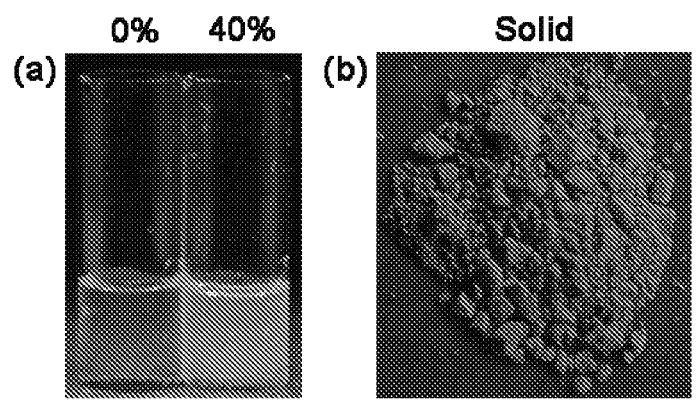
FIG. 7 shows photographs of (a) MTPE-TP in THF and THF/water mixtures with 40% water fraction (fw), and (b) the solid sample taken under 365 nm UV-light illumination.
Figure 13:
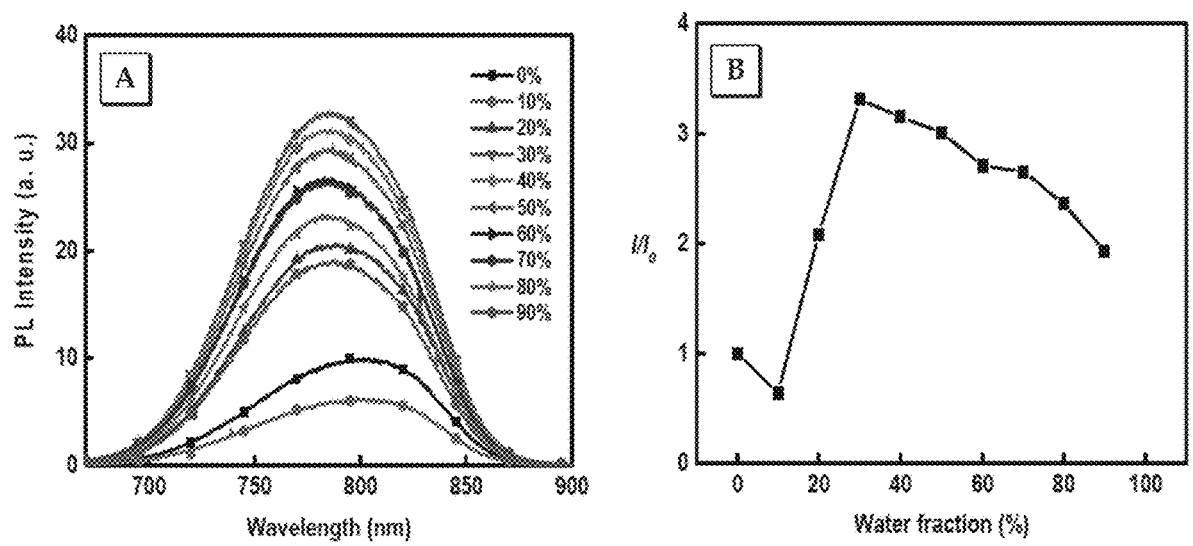
FIG. 13 shows (A) photoluminescence (PL) spectra of MTPE-TT in DMSO and DMSO/water mixtures with increasing water fractions (fw) from 10% to 90%. (B) Change in PL intensity of MTPE-TT versus water fraction in DMSO/water mixtures. Excitation at 610 nm.
Figure 14:
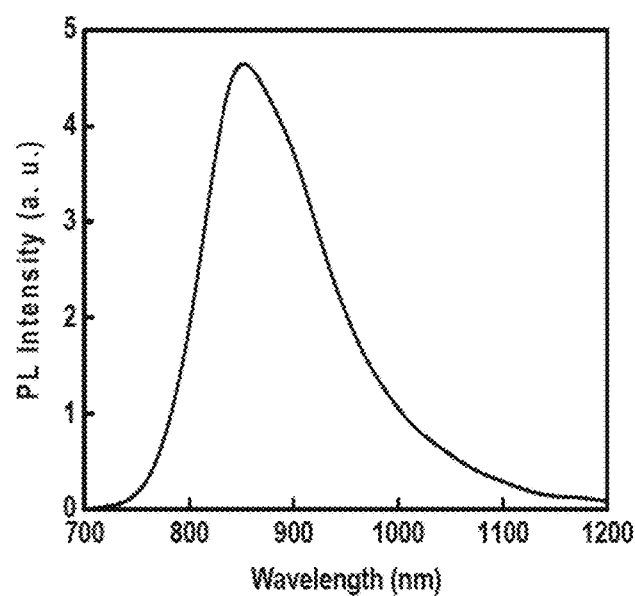
FIG. 14 shows photoluminescence (PL) spectrum of MTPE-TT in the solid state.
Figure 15:
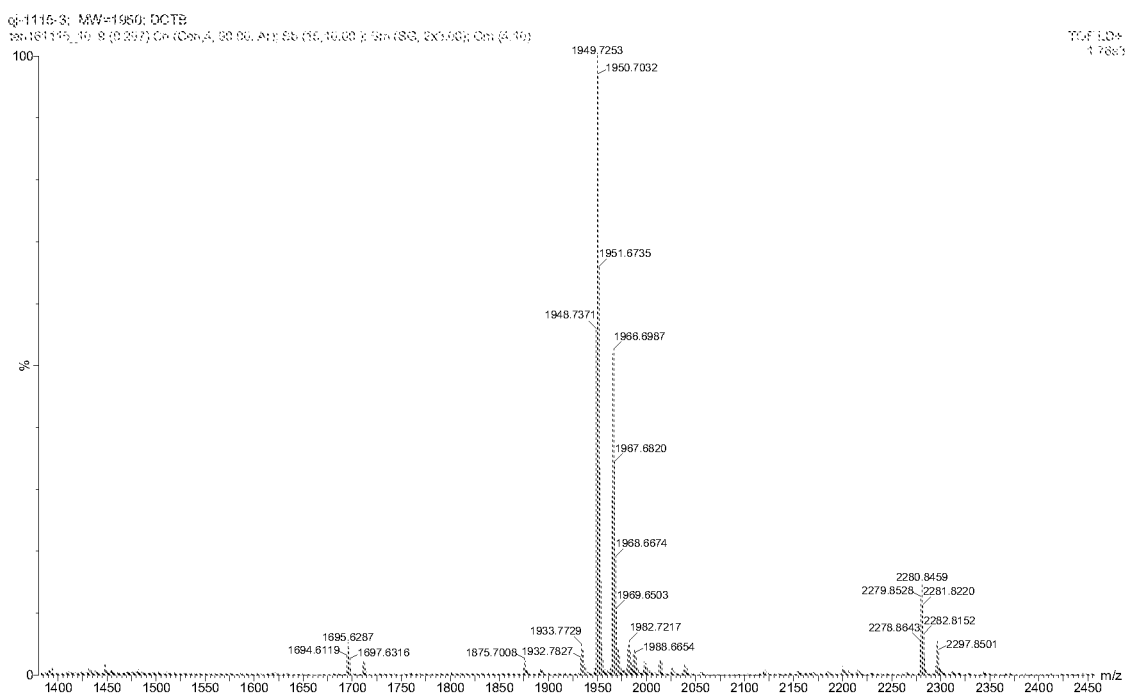
FIG. 15 shows mass spectrum of TPE-TPA-TT.
Figure 16:
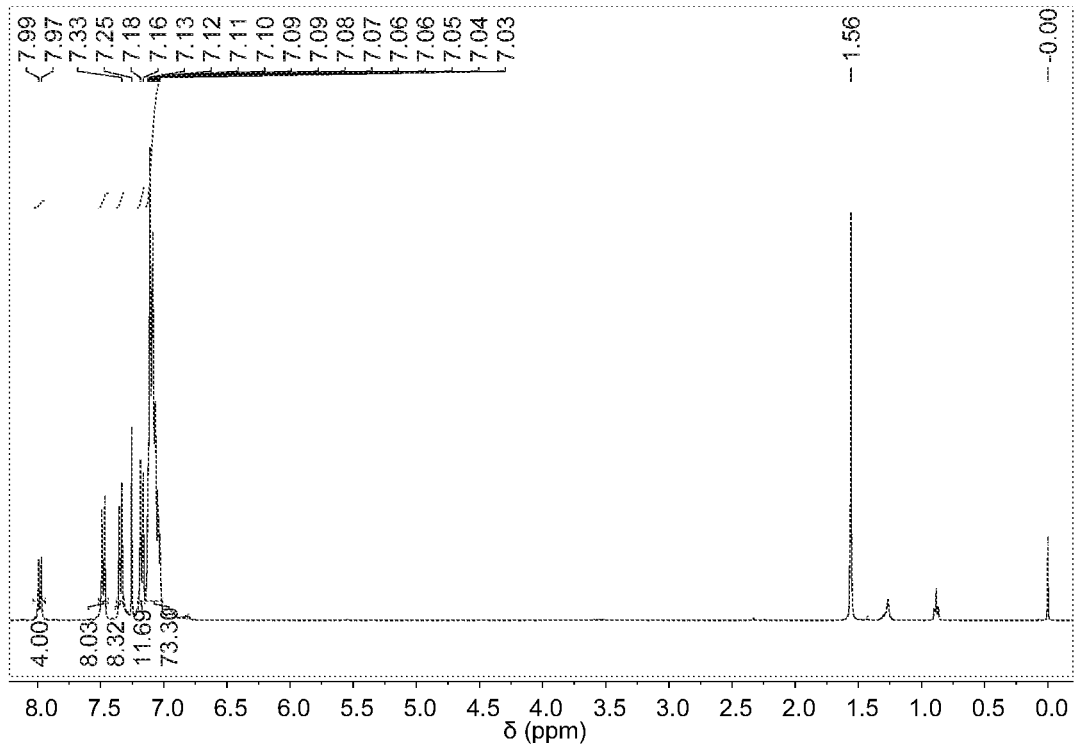
FIG. 16 shows $^1$H-NMR spectrum of TPE-TPA-TT in $CDCl_3$.
Figure 17:
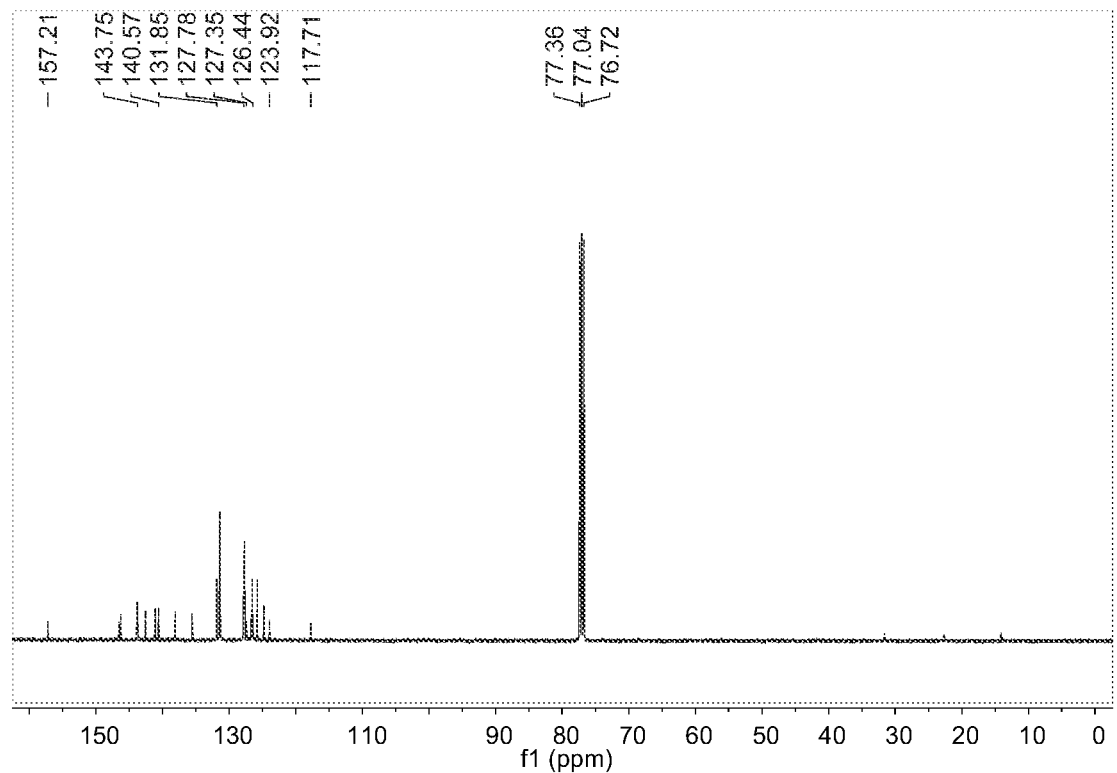
FIG. 17 shows $^{13}$C-NMR spectrum of TPE-TPA-TT in $CDCl_3$.
Figure 18:
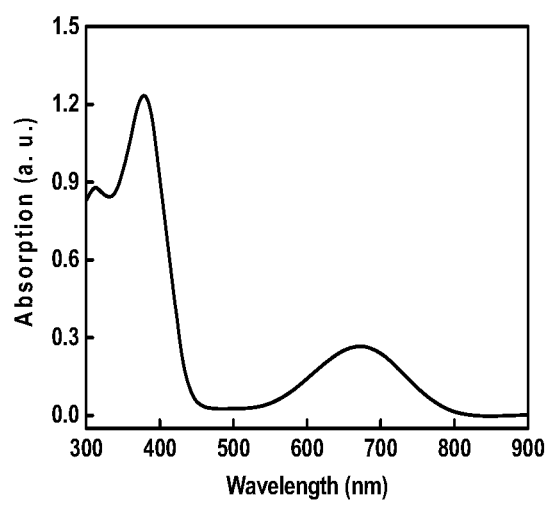
FIG. 18 shows absorption spectrum of TPE-TPA-TT in THF.
Figure 19:
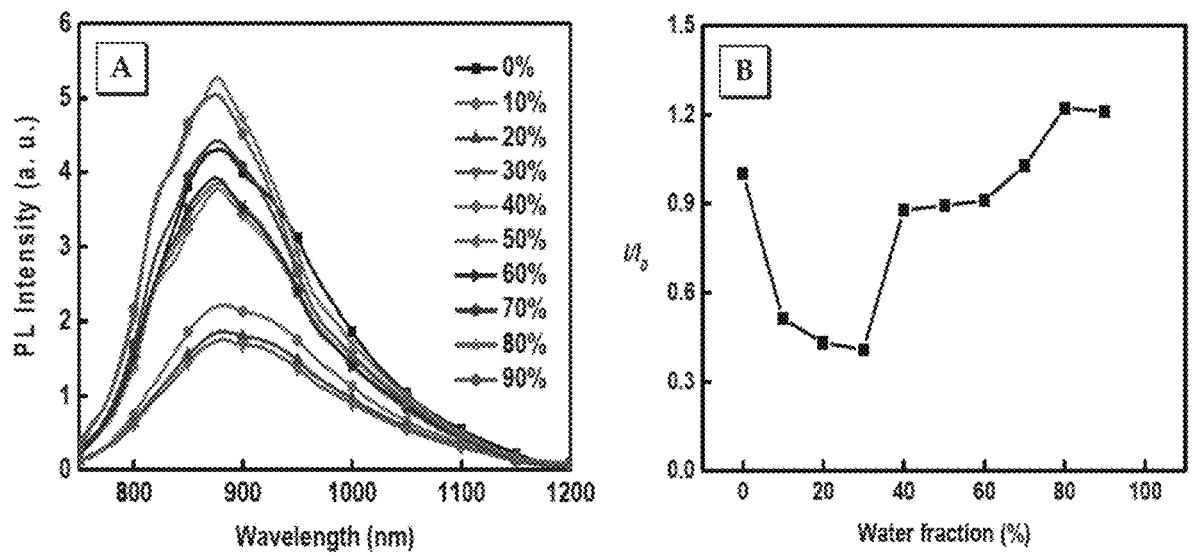
FIG. 19 shows (A) photoluminescence (PL) spectra of TPE-TPA-TT in THF and THF/water mixtures with increasing water fractions (fw) from 10% to 90%. (B) Change in PL intensity of TPE-TPA-TT versus water fraction in THF/water mixtures. Excitation at 670 nm.
Figure 20:
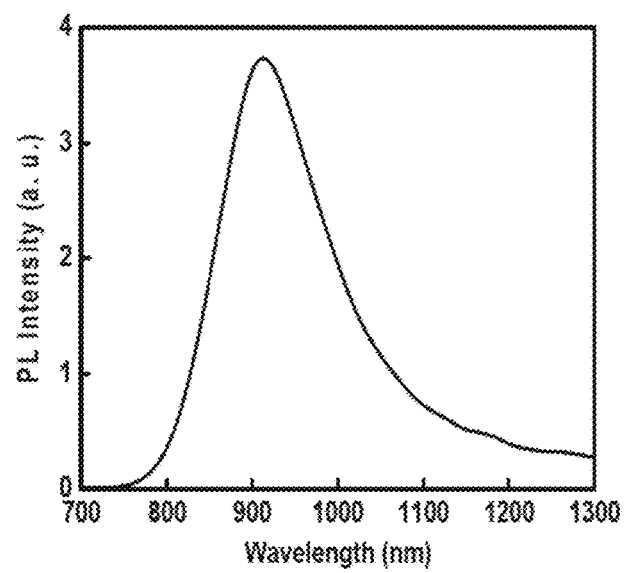
FIG. 20 shows photoluminescence (PL) spectrum of TPE-TPA-TT in the solid state.
Figure 21:
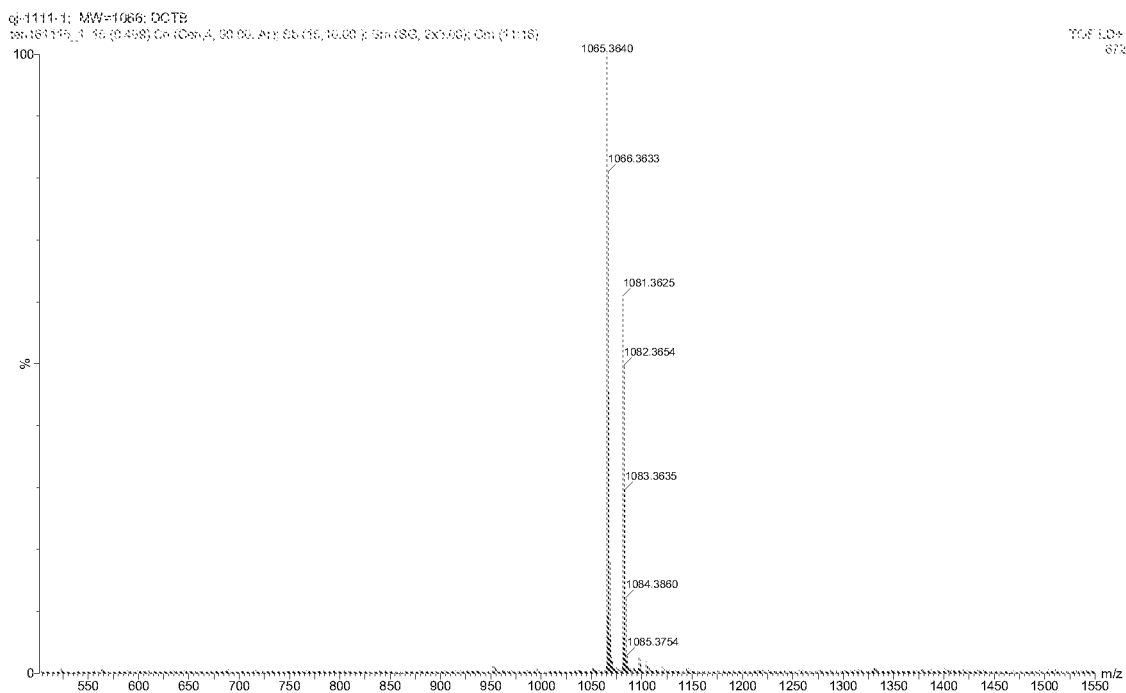
FIG. 21 shows mass spectrum of PTZ-BT-TPA.
Figure 22:
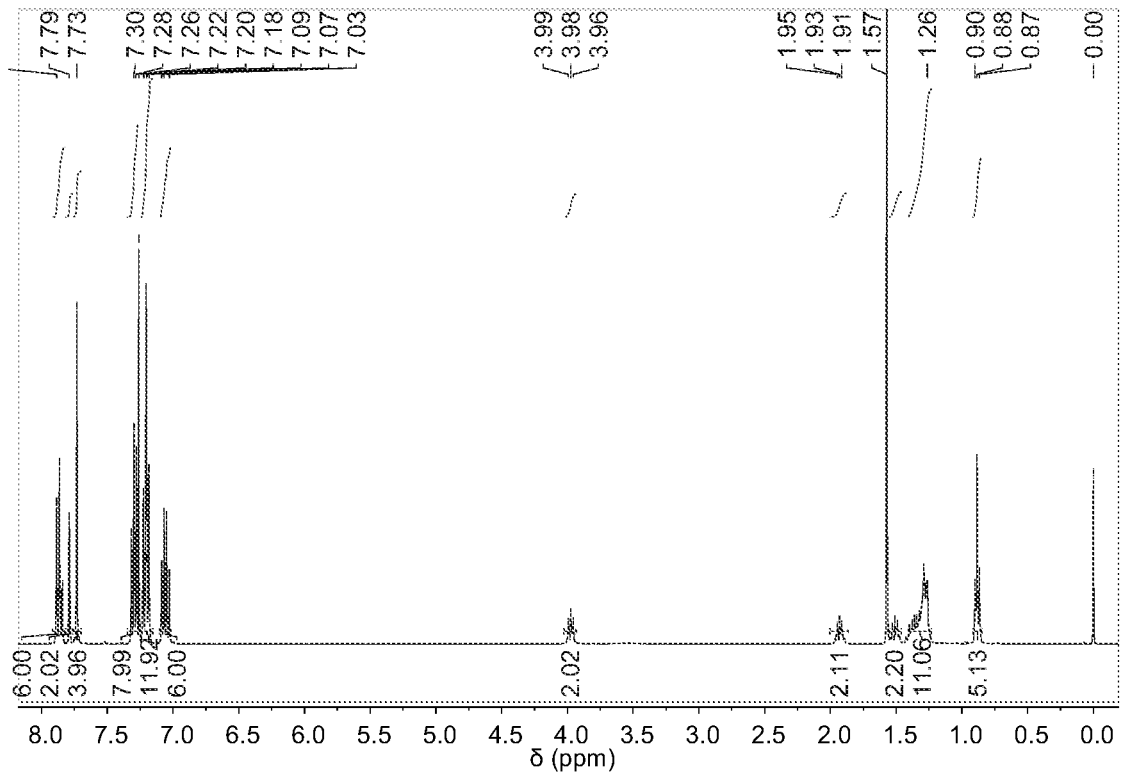
FIG. 22 shows $^1$H-NMR spectrum of PTZ-BT-TPA in $CDCl_3$.
Figure 23:
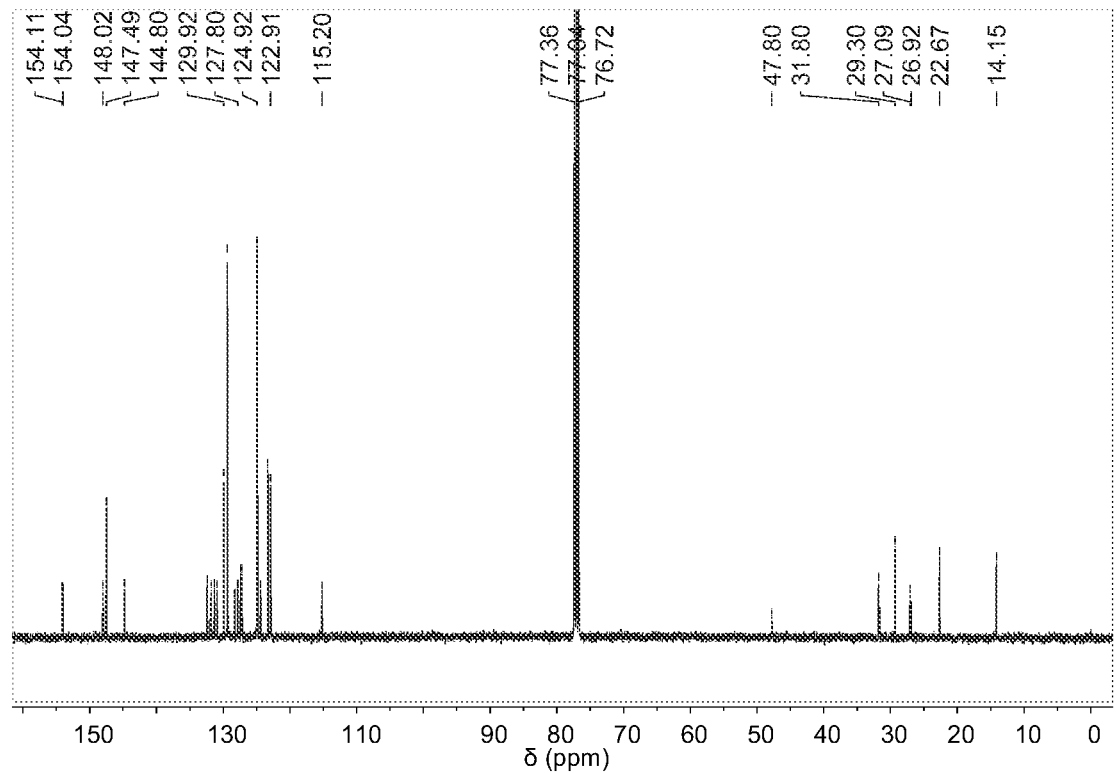
FIG. 23 shows $^{13}$C-NMR spectrum of PTZ-BT-TPA in $CDCl_3$.
Figure 24:
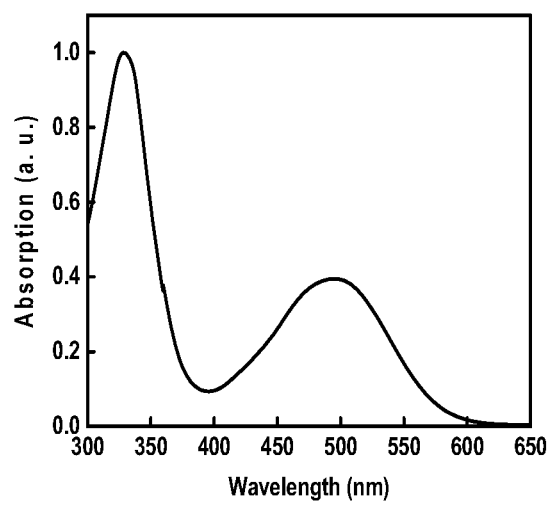
FIG. 24 shows absorption spectrum of PTZ-BT-TPA in THF.
Figure 25:
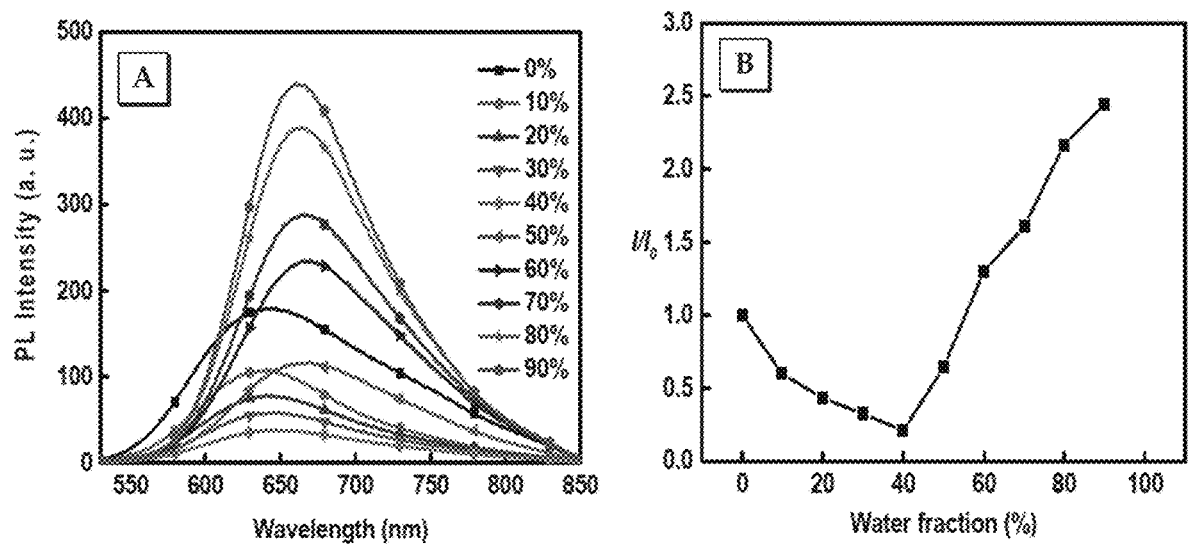
FIG. 25 shows (A) photoluminescence (PL) spectra of PTZ-BT-TPA in THF and THF/water mixtures with increasing water fractions (fw) from 10% to 90%. (B) Change in PL intensity of PTZ-BT-TPA versus water fraction in THF/water mixtures. Excitation at 500 nm.
Figure 26:
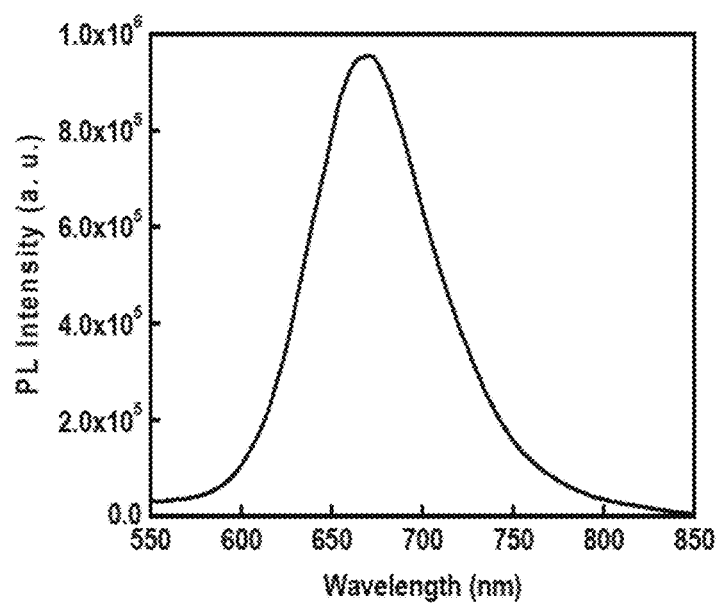
FIG. 26 shows photoluminescence (PL) spectrum of PTZ-BT-TPA in the solid state.
Figure 27:
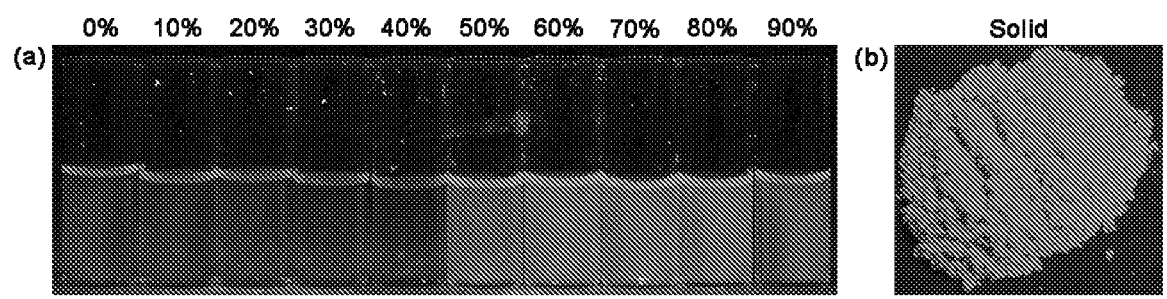
FIG. 27 shows photographs of (a) PTZ-BT-TPA in THF and THF/water mixtures with increasing water fractions (fw) from 10% to 90%, and (b) the solid sample taken under 365 nm UV-light illumination.

The dyes MTPE-TP and MTPE-TT showed typical twisted intramolecular charge transfer (TICT) and AIE features when the water fractions were increased in the DMSO/water mixtures (FIGS. 5 and 13). The dyes TPE-TPA-TT, PTZ-BT-TPA, NPB-TQ, TPE-TQ-A, and MTPE-BTSe showed typical twisted intramolecular charge transfer (TICT) and AIE features when the water fractions were increased in the THF/water mixtures as shown in (FIGS. 19, 25, 33, 38, and 44). Initially, a small amount of water was added, and the fluorescence decreased, a typical TICT effect arising from increased solvent polarity. When more water was added, the AIE molecules formed nanoaggregates, and the emission increased. The solutions of the AIEgens were slightly emissive in solution, while strongly emissive in the aggregation state of 90% water fraction.

Pyrazine-Containing Red/Near-Infrared AIE Luminogens

In the present subject matter, pyrazine-containing red and near-infrared AIEgens having D-A structures are generated in simple synthetic steps. Pyrazine or dipyrazine are used as acceptors to tune the electron accepting property, while triphenylamine, carbazole, and their derivatives or other groups are utilized as donors to tune the electron donating property, which enables the photo-physical property of AIEgens. The resulting AIEgens are conjugated with whole aromatic structures wherein no double bond is involved, thus making the luminogens much more stable than common, conventional luminogens.

The AIEgens show maximum emissions ranging from 630-900 nm, covering the spectral range from red to near-infrared light. Due to features including deep tissue penetration, negligible biological auto-fluorescence, low photo-damage, and high signal-to noise ratio, etc., the AIEgens exhibit huge application potential in preclinical research and clinical practice for noninvasive real-time tumor diagnosis and image-guided cancer therapy. Although no molecular rotator of TPE is incorporated into the structure, all of the luminogens are still AIE-active because they possess twisted and flexible molecular conformation.

In solution state, the luminogens are non-emissive or less emissive, because intramolecular motion easily takes place to dissipate the excitation state energy non-radiatively, whereas in the aggregated state, such motion is suppressed to open up the radiative transition channel. Meanwhile, the twisted conformation of pyrazine-contained luminogens may prohibit the formation of π-π stacking when molecules are closely located. Both factors collectively determine a remarkably enhanced emission in the aggregate state. The AIE behavior of pyrazine-contained luminogens may facilitate the fabrication of highly emissive nanoparticles with excellent stability, which is extremely desirable for biological applications.

Characterization $^1$H and $^{13}$C NMR spectra were measured with a Bruker AVIII 400 spectrometer using $CDCl_3$ or $CD_3Cl_2$ as the solvent. When $CDCl_3$ was used, the tetramethylsilane (TMS; δ=0) was used as the internal reference. High resolution mass spectra (HRMS) were recorded using a GCT premier CAB048 mass spectrometer operated in MALDI-TOF mode. Absorption spectra were recorded on a Varian Cary 50 spectrophotometer. Steady-state fluorescence spectra were measured using a Perkin Elmer LS 55 spectrometer or a HORIBA Spectrofluorometer.

Figure 55:
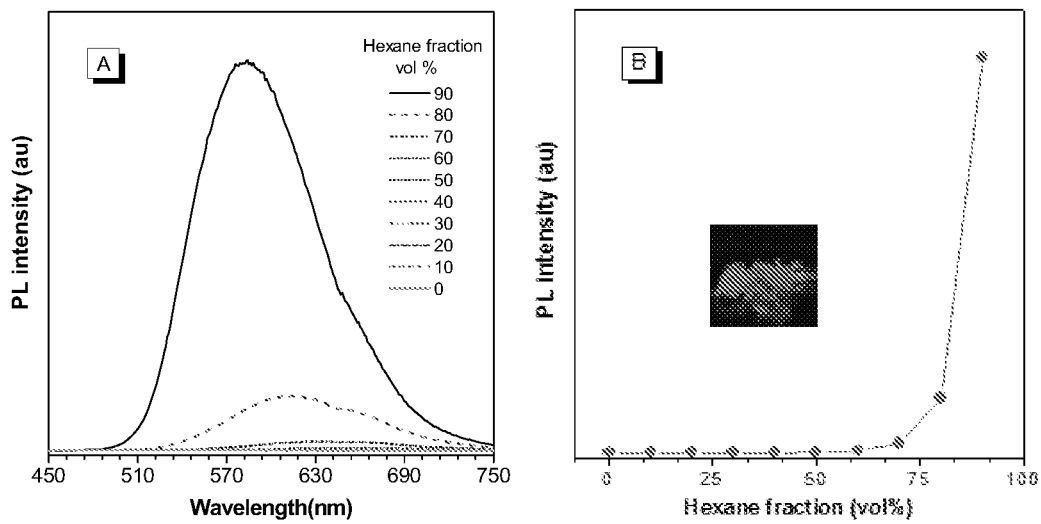
FIG. 55 shows (A) PL spectra of DCDPP-2TPA4M in THF/hexane mixtures with different hexane contents, concentration is $10^{-5}$ M, $\lambda_{ex}$=439 nm; (B) PL intensities of DCDPP-2TPA4M in THF/hexane mixtures with different water contents, insert: Photographs of the powder of DCP-2TPA4M taken under 365 nm UV light.
Figure 56:
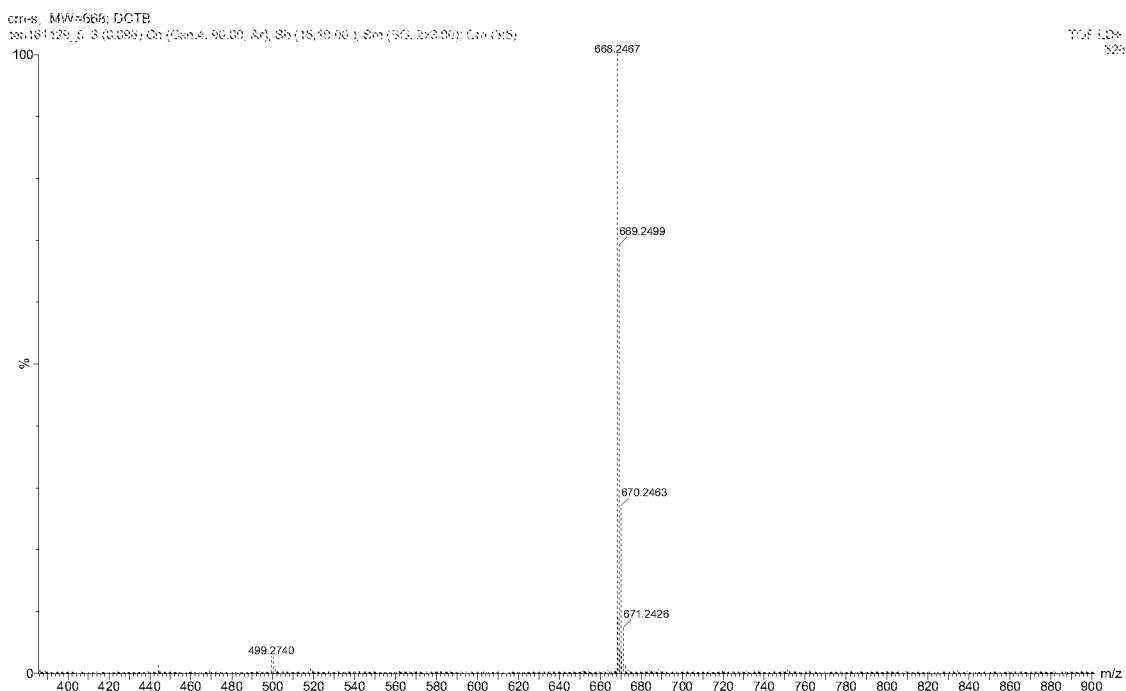
FIG. 56 shows HRMS of DCDP-2TPA.
Figure 57:
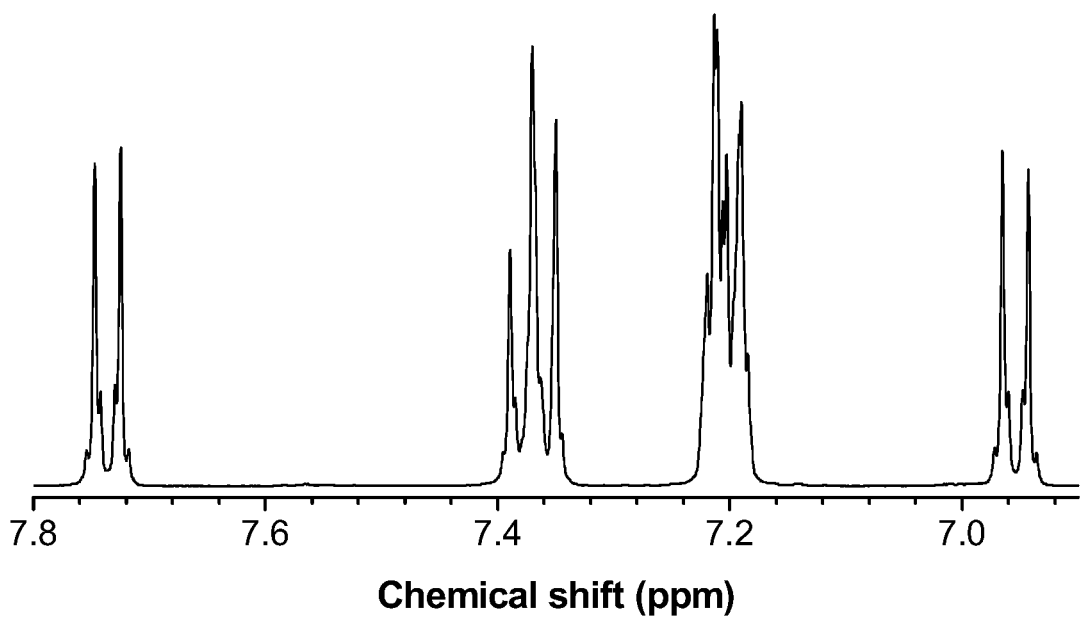
FIG. 57 shows $^1$H NMR spectrum of DCDP-2TPA in $CD_2Cl_2$.
Figure 58:
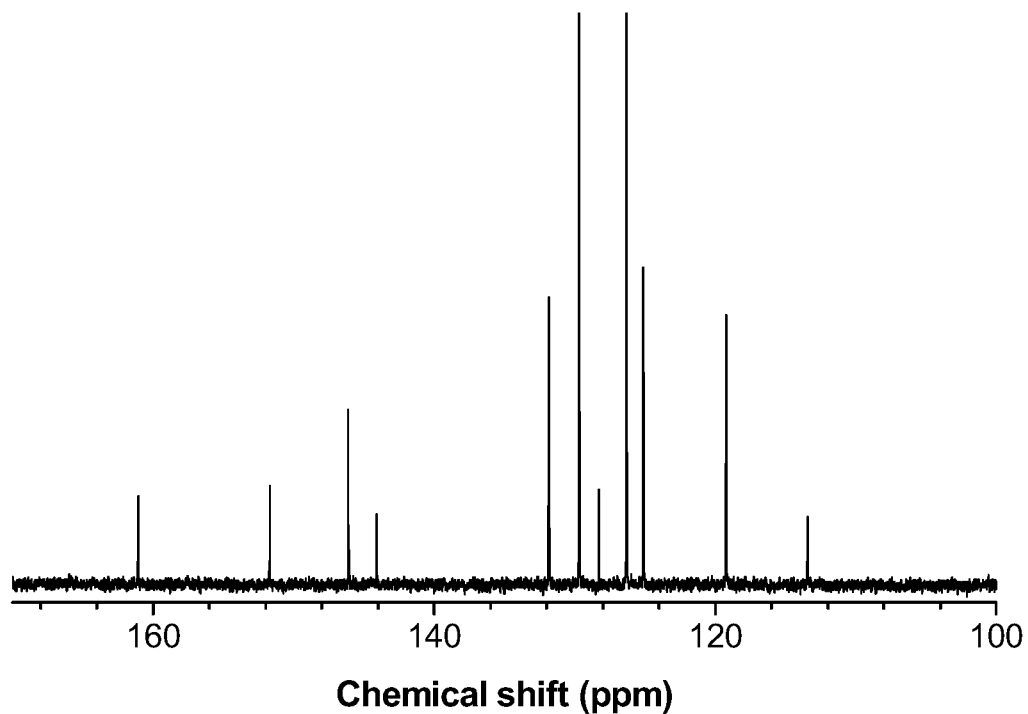
FIG. 58 shows $^{13}$C NMR spectrum of DCDP-2TPA in $CD_2Cl_2$.
Figure 59:
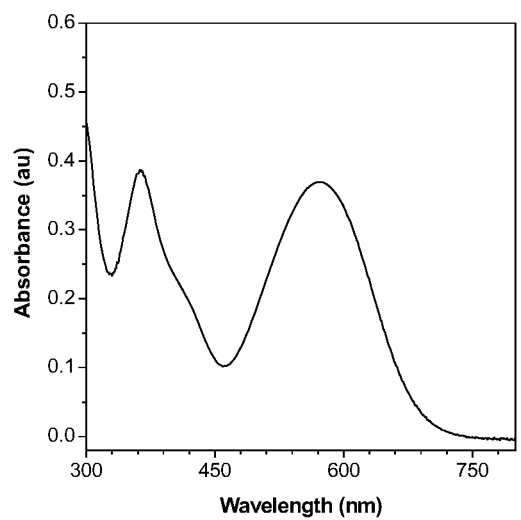
FIG. 59 shows UV-vis spectrum of DCDP-2TPA in THF.
Figure 60:
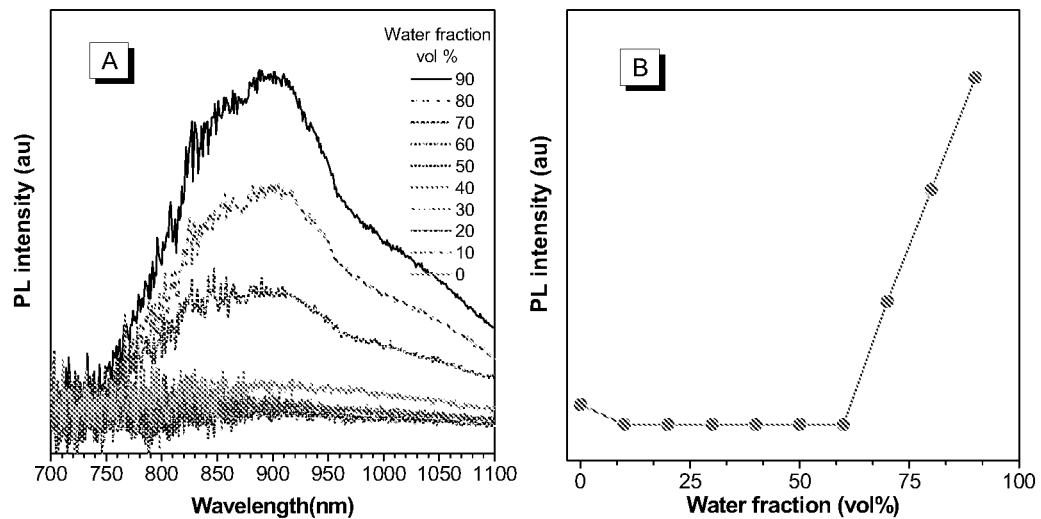
FIG. 60 shows (A) PL spectra of DCDP-2TPA in THF/water mixtures with different water contents, concentration is $10^{-5}$ M, $\lambda_{ex}$=574 nm; (B) PL intensities of DCDP-2TPA in THF/water mixtures with different water contents.
Figure 61:
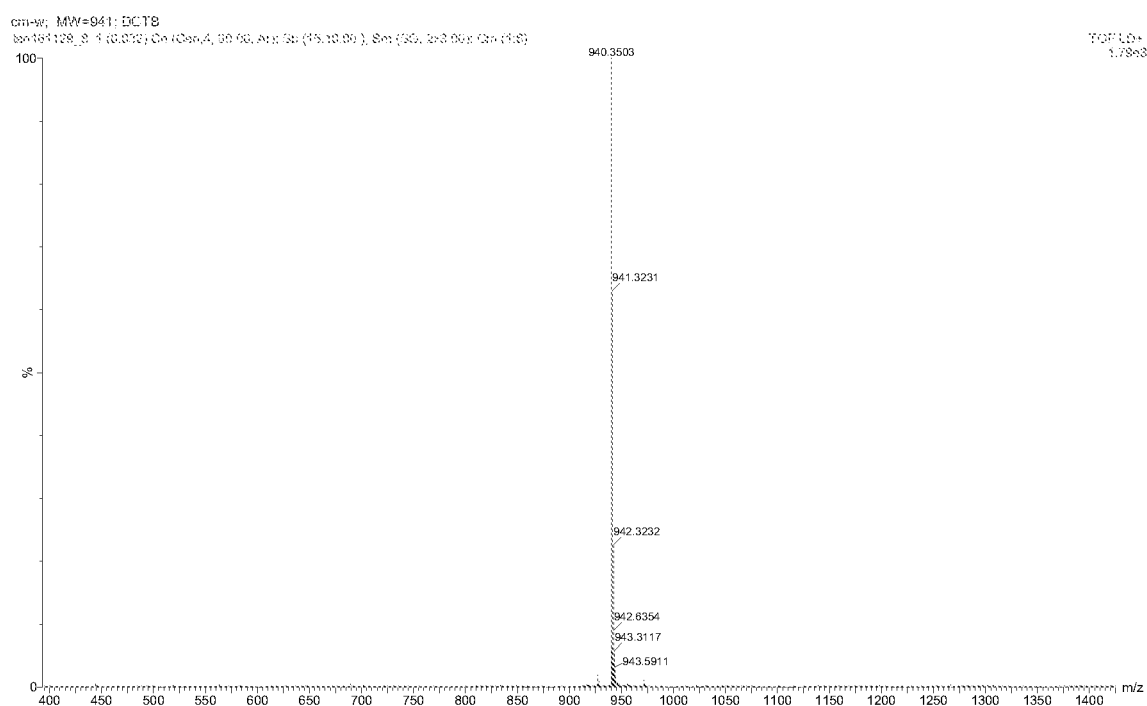
FIG. 61 shows HRMS of DCDP-2TPA4M.
Figure 62:
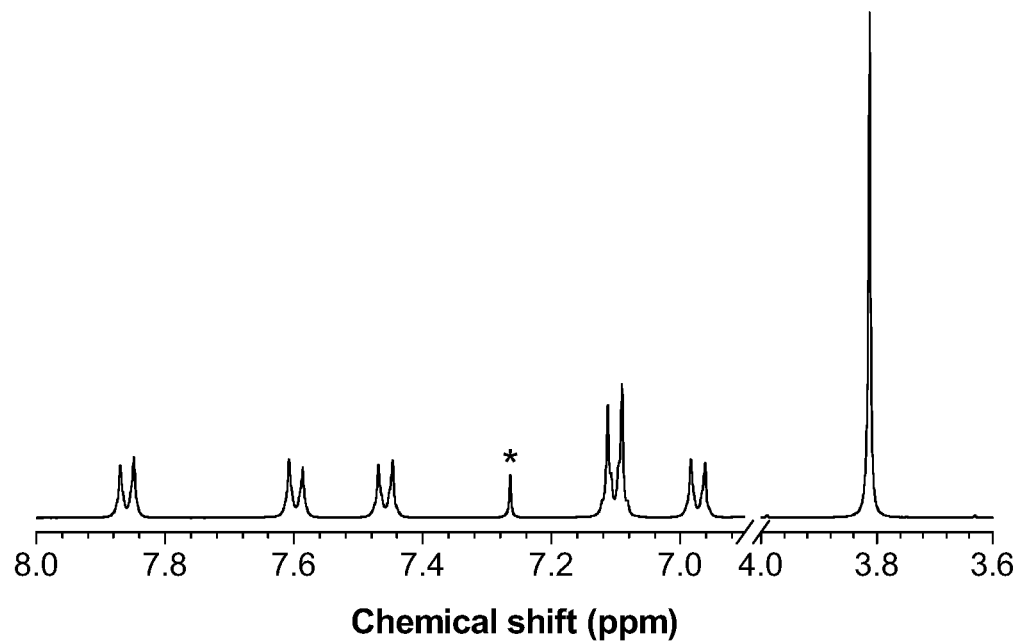
FIG. 62 shows $^1$H NMR spectrum of DCDP-2TPA4M in $CDCl_3$.
Figure 63:
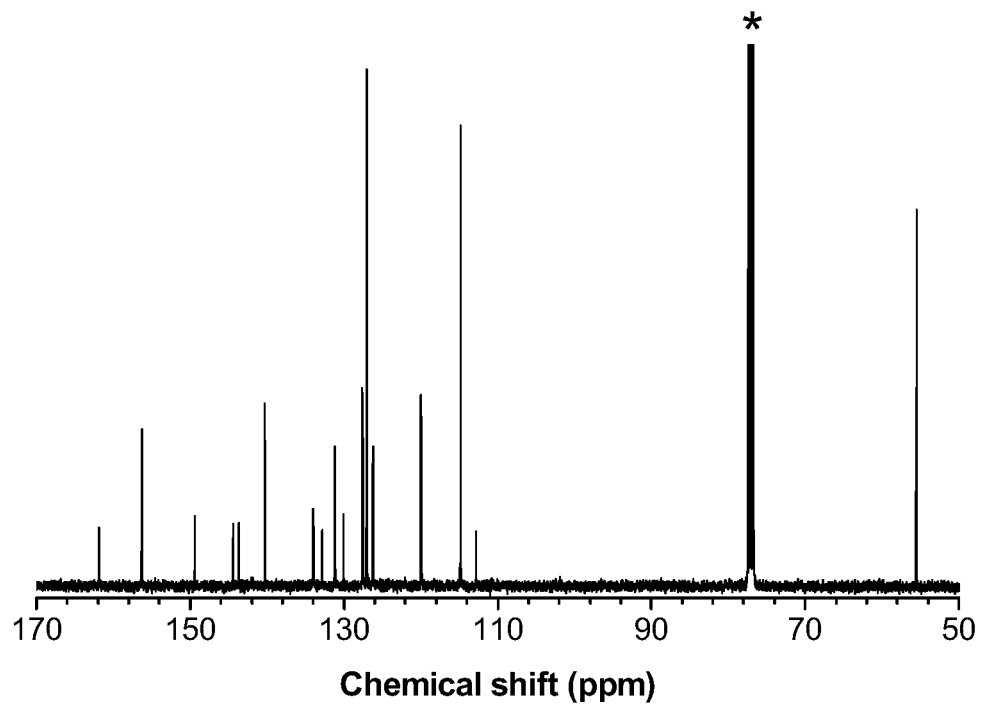
FIG. 63 shows $^{13}$C NMR spectrum of DCDP-2TPA4M in $CDCl_3$.
Figure 64:
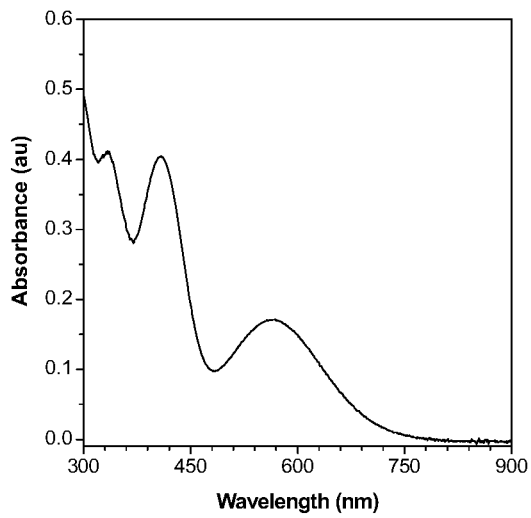
FIG. 64 shows UV-vis spectrum of DCDP-2TPA4M in THF.
Figure 65:
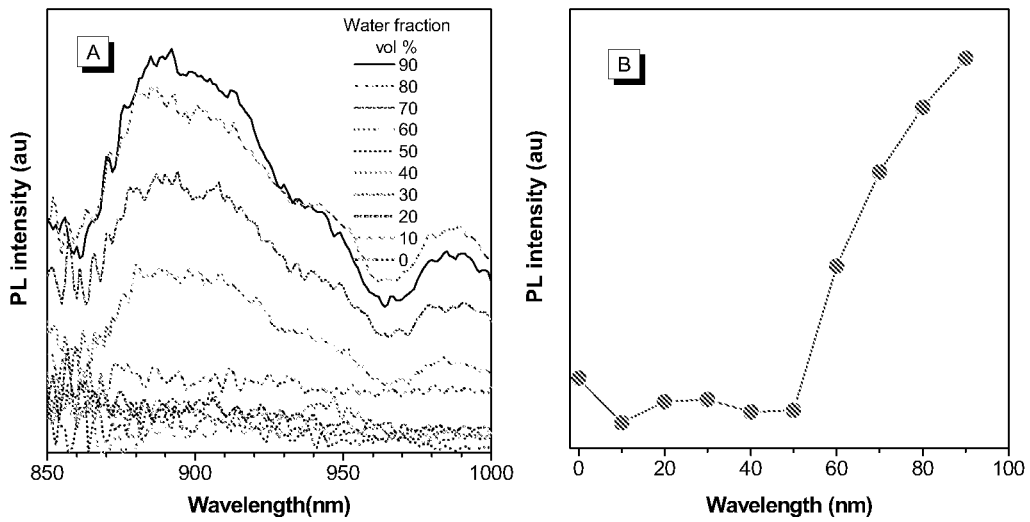
FIG. 65 shows (A) PL spectra of DCDP-2TPA4M in THF/water mixtures with different water contents, concentration is $10^{-5}$ M, $\lambda_{ex}$=570 nm; (B) PL intensities of DCDP-2TPA4M in THF/water mixtures with different water contents.

Some of the developed luminogens exhibited typical AIE properties, whereas others displayed weak twisted intramolecular charge transfer (TICT) effects plus strong AIE effects. For example, DCDPP-2TPA4M gives no emission when molecules are dissolved in THF. After addition of the poor solvent of hexane, no emission is observed when the hexane fraction reaches 60%. However, a remarkable enhanced emission can be detected when further increasing the hexane fraction. Because hexane is a poor solvent, the addition of a large amount of hexane into the THF solution must induce the formation of aggregates, thus giving rise to the AIE phenomenon (FIG. 55). The AIE effect can be also detected in aggregates of DCDP-2TPA formed in high water fractions of THF/water mixtures, and a very weak emission can be found when molecules are dispersed in THF, which is due to the TICT effect (FIG. 60).

Design and Synthesis of Red AIEgens for In Vivo Deep-Tissue Imaging

The present subject matter relates to a design strategy for ultrabright red luminogens with aggregation-induced emission (AIE) features in a strong donor-acceptor (D-A) system and use of said strategy for the development of AIE luminogens for in vivo deep-tissue imaging by two-photon imaging technique with high performances. In particular, the presently described subject matter relates to luminogens comprising tetraphenylethene derivatives featured with aggregation-induced emission characteristics (AIE).

In one embodiment, these luminogens have arylamine as the electron donor and benzothiadiazole or benzoselenadiazole as the electron acceptor. Moreover, the strategy sheds light on the development of efficient solid-state red/NIR emitters with high brightness, large Stokes shift, good biocompatibility, satisfactory photostablility and high two-photon absorption cross section for high contrast in vivo deep-tissue imaging.

In one embodiment, the present subject matter generally relates to a design strategy for ultrabright red luminogens with aggregation-induced emission (AIE) features based on the presence of a TPE group, an arylamine, and a benzothiadiazole or benzoselenadiazole unit. Due to enhanced charge transfer (CT) effect, the background emission in THF of red luminogen is successfully suppressed using such compounds, with several hundred fold of emission enhancements in the aggregated state. Moreover, thanks to the highly emissive feature of TPE derivatives in the solid state, in vivo deep-tissue imaging, including brain vascular imaging, sentinel lymph node mapping and tumor imaging, with high contrast and high penetration depth are achieved.

In an embodiment, the present subject matter relates to use of an AIE material as a fluorescent probe for brain vascular imaging, sentinel lymph node mapping and tumor imaging.

In another embodiment, the present subject matter relates to use of an AIE material as fluorescent probe with good biocompatibility.

Figure 66:
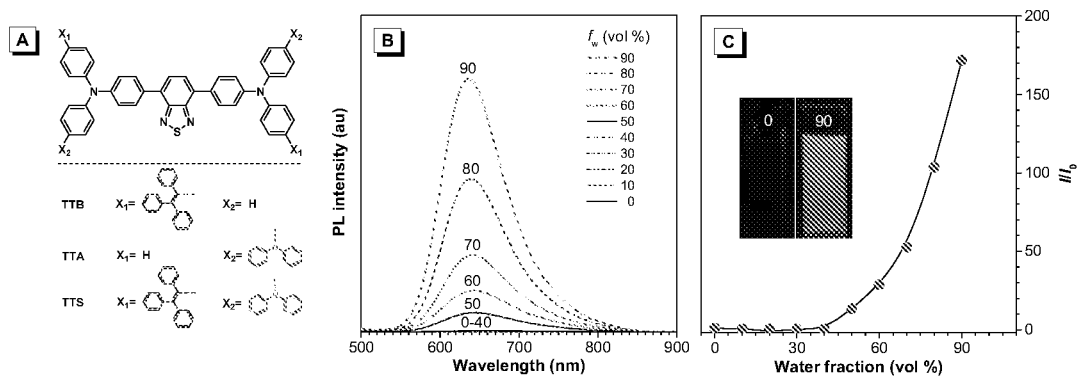
FIG. 66 shows (A) molecular structure of TTB, TTA and TTS. (B) PL spectra of TTS in THF/water mixtures with different water fractions ($f_w$). (C) Plots of relative PL intensity ($I/I_0$) versus the composition of THF/water mixtures of TTS. $I_0$=emission intensity in pure THF solution. Concentration: 10 µM; excitation wavelength: 480 nm. Inset: fluorescent photographs of TTS in THF ($f_w$=0%) and the THF/water mixture with $f_w$=90% taken under 365 nm UV illumination.

The photoluminescence (PL) spectrum of TTS (FIG. 66) is basically a flat line parallel to the abscissa in pure THF. The spectral pattern remains unchanged at water content up to 40%. Afterwards, the PL intensity increases dramatically. The higher the water fraction, the stronger the emission intensity. The emission peak reaches to ~636 nm. The emission intensity reaches its maximum value at 90% water content, which is 170-fold higher than that in pure THF solution.

Figure 67:
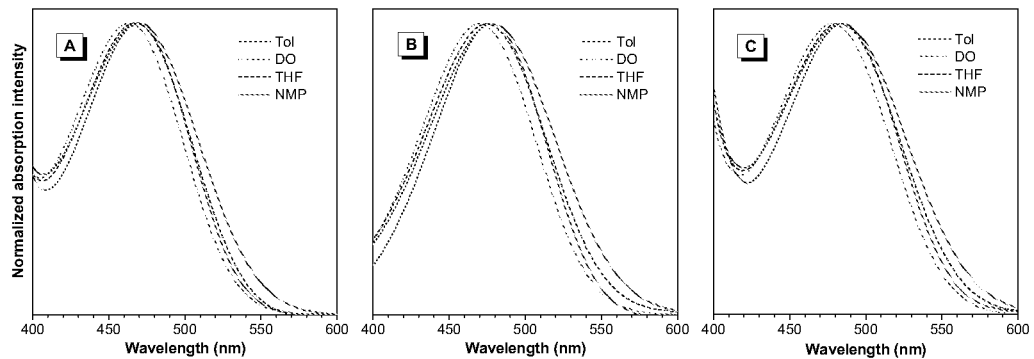
FIG. 67 shows normalized absorption spectra of (A) TTB, (B) TTA and (C) TTS in solvents with different polarities.

FIG. 67 shows the UV spectrum of TTB, TTA, and TTS measured in different solvents. With introduction of extra arylamine units to the TTB molecule, the absorption peak of TTS is slightly red-shifted due to longer electronic conjugation. The absorption peaks of TTB, TTA, and TTS are not significantly affected by the solvent polarity.

TABLE 1

Absorption and emission of TTB, TTA and TTS in different solvents.

| Solvent | TTB $\lambda_{ab}$ (nm)[a] | TTB $\lambda_{em}$ (nm)[b] | TTA $\lambda_{ab}$ (nm)[a] | TTA $\lambda_{em}$ (nm)[b] | TTS $\lambda_{ab}$ (nm)[a] | TTS $\lambda_{em}$ (nm)[b] |
|---|---|---|---|---|---|---|
| Tol | 470 | 596 | 478 | 620 | 484 | 623 |
| DO | 465 | 609 | 471 | 632 | 478 | 640 |
| THF | 469 | 618 | 474 | nd[c] | 481 | nd[c] |
| NMP | 469 | 654 | 478 | nd[c] | 484 | nd[c] |

[a]$\lambda_{ab}$ = absorption maximum.
[b]$\lambda_{em}$ = emission maximum.
[c]nd = not detected.

Figure 68:
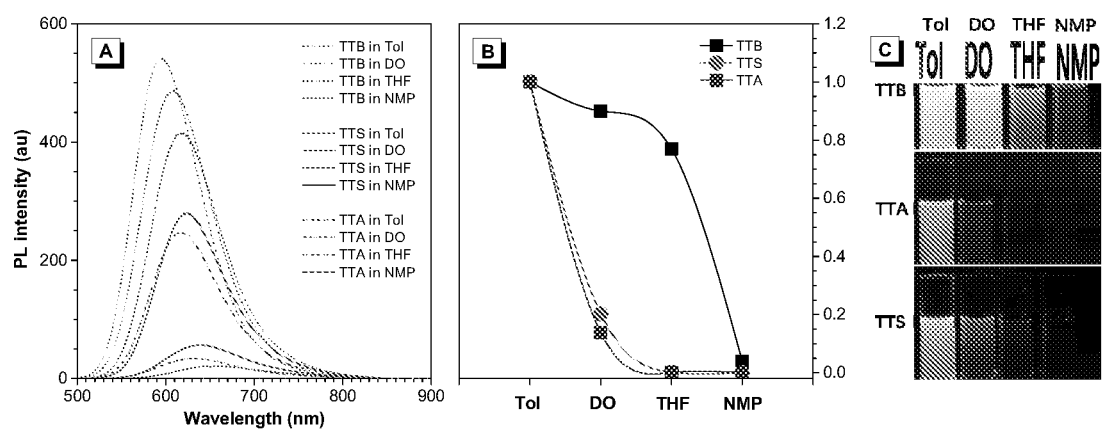
FIG. 68 shows (A) emission spectra of TTB, TTS and TTA in solvents with different polarities. Concentration: 10 µM; excitation wavelength: 480 nm. (B) Plots of fluorescence intensity of TTB, TTA or TTS in different solvents (I) versus emission intensity in toluene ($I_{Tol}$). (C) fluorescent photographs of TTB, TTA and TTS in different solvents taken under 365 nm UV illumination

The PL spectra of TTB, TTA, and TTS measured in different solvents are shown in FIG. 68. When the solvent polarity was increased from Tol to NMP, the emission of TTB, TTA, and TTS are red-shifted with an emission quenching effect. This suggests that these molecules have an intramolecular charge transfer (CT) effect from the electron-donating arylamine unit to the electron-accepting benzothiadiazole. However, compared with TTB molecule, TTA and TTS molecules are more sensitive to solvent polarity. TTA and TTS are emissive in Tol, weak emissive in DO and nonemissive in THF with medium polarity. In contrast, TTB is highly emissive in Tol, DO, and THF, and even in the high polarity solvent NMP, TTB is still emissive observed by the naked eye. The result shows that the stronger D-A system with two more arylamine units fusioned to the TTB molecular structure greatly enhances the CT effect. It is probable that even in THF with medium polarity, the conformation of the TTA or TTS becomes twisted and the charge becomes separated. Its light emission is red-shifted in color, but significantly decreased in intensity due to the locally excited (LE) state to twisted intramolecular charge transfer (TICT) state transition.

Figure 69:
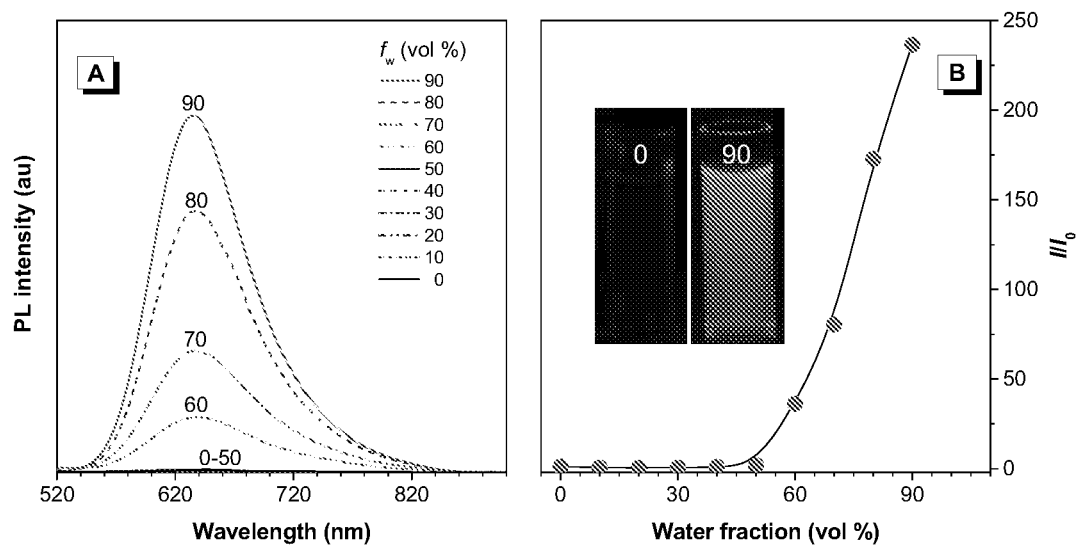
FIG. 69 shows (A) chemical structure of TTA. (B) UV spectrum of TTA in THF solution. Concentration: 10 µM. (C) PL spectra of TTA in THF/water mixtures with different water fractions ($f_w$). (D) Plots of relative PL intensity ($I/I_0$) versus the composition of THF/water mixtures of TTA. $I_0$=emission intensity in pure THF solution. Concentration: 10 µM; excitation wavelength: 480 nm. Inset: fluorescent photographs of TTA in THF ($f_w$=0%) and the THF/water mixture with $f_w$=90% taken under 365 nm UV illumination.

In an embodiment, the PL spectrum of TTA shows a similar behavior to TTS (FIG. 69). In pure THF solution, it is non-emissive. The PL intensity remains unchanged at water fraction $f_w$<50%. Afterwards, the PL intensity reaches its maximum value at 90% water content with emission peak at ~635 nm. Thus, both TTS and TTA are AIE-active.

TABLE 2

Optical properties of TTS.

| | $\lambda_{ab}$ (nm)[a] | $\lambda_{em}$ (nm)[b] soln | $\lambda_{em}$ (nm)[b] aggr | powder ($\Phi_F$)[c] | τ (ns)[d] | $E_g$ (eV)[e] | HOMO/ LUMO(eV)[f] |
|---|---|---|---|---|---|---|---|
| TTS | 481 | 641 (0.1) | 636 | 636 (34.1) | 1.86 | 2.21 (2.29) | −5.05 (−4.52)/ −2.84 (−2.23) |

[a]$\lambda_{ab}$ = absorption maximum in THF.
[b]$\lambda_{em}$ = emission maximum in THF solution (soln), THF/water mixture (1:9 by volume) (aggr).
[c]solid powders fluorescence quantum yield ($\Phi_F$, %) given in the parentheses.
[d]fluorescence lifetime of solid powders (τ).
[e]$E_g$ = energy band gap calculated from the onset of the absorption spectrum.
[f]HOMO = highest occupied molecular orbitals calculated from the onset oxidation potential, LUMO = lowest unoccupied molecular orbitals estimated by using the equation: LUMO = HOMO + Eg, the values in the parentheses are derived from theoretical DFT calculations.

Figure 70:
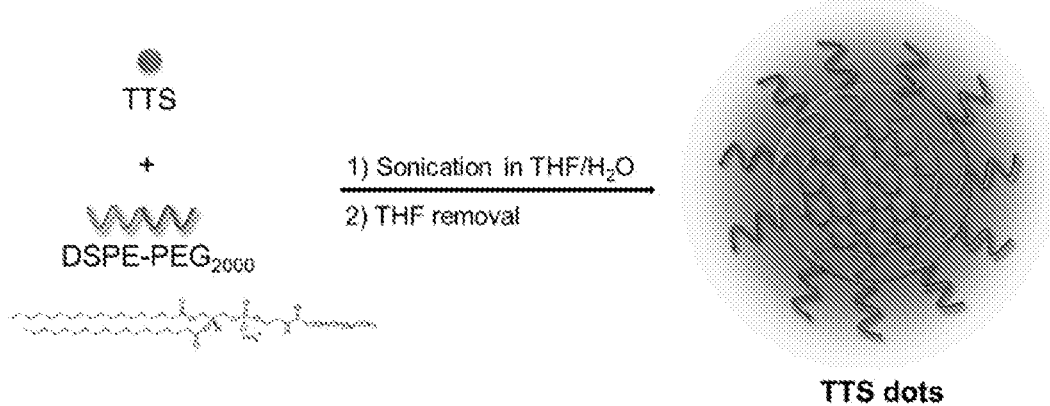
FIG. 70 shows the schematic illustration of AIE dot fabrication.
Figure 71:
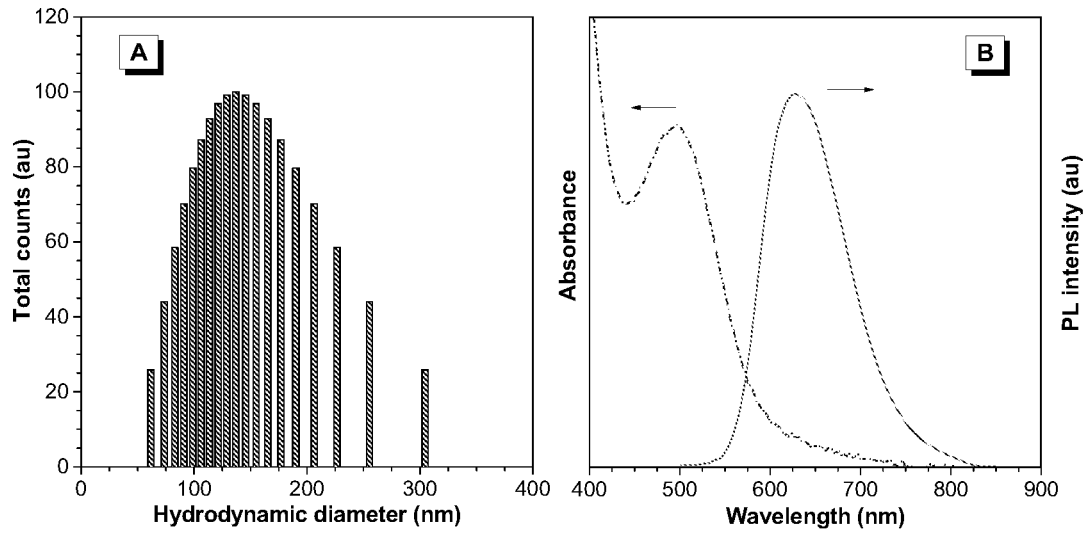
FIG. 71 shows (A) particle size distribution studied by dynamical light scattering (DLS) and (B) absorption and emission spectra of TTS dots suspended in water; $\lambda_{ex}$=488 nm.

Due to the higher $\Phi_F$ and much better processability of TTS, it was chosen for further biological applications. For easy dispersion of the highly hydrophobic TTS molecules in an aqueous environment, the TTS dots were formulated through a simple procedure by a nanoprecipitation method with amphiphilic and biocompatible 1,2-distearoyl-sn-glycero-3-phosphoethanolamine-N [methoxy(polyethyleneglycol)-2000] (DSPE-PEG 2000) as the encapsulation matrix (FIG. 70). The size of TTS dots was measured by laser light scattering (LLS), which indicated that the hydrodynamic diameter was ~120 nm (FIG. 71A). TTS dots have an absorption maxima at 497 nm in aqueous media, which fits well with the commercial laser excitation at 488 nm. The strong emission of TTS dots (FIG. 71B) peaks at the red region (630 nm) and tails to the near-infrared region (820 nm). It is noteworthy that the Stokes shift of the TTS dots is big enough (>130 nm) to solve the serious problem of the self-quenching effect common in conventional organic dye molecules.

Figure 72:
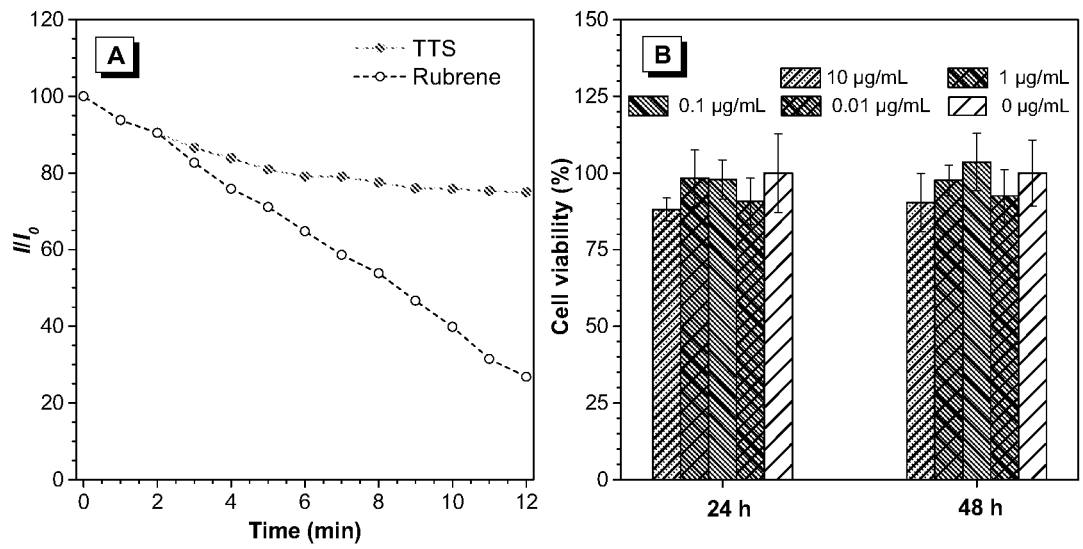
FIG. 72 shows (A) photostability of TTS dots under continuous scanning at 480 nm using 450 W Xe lamp. $I_0$ is the initial PL intensity, while I is that of the corresponding sample after a designated time interval. (B) Cell viability of A549 cells after incubation with 0, 0.01, 0.1, 1, and 10 µg/mL TTS dots for 24 hours, 48 hours, respectively.

FIG. 72A shows the different fluorescence stability of AIE dots and rubrene dots at continuous irradiation with a 480 nm Xe lamp. After 12 minutes of irradiation, the AIE dots maintained ~80% of their initial fluorescence intensity, which is much higher than that of rubrene dots (~25%). The cytotoxicity of the AIE dots was evaluated by metabolic viability of A549 cells after incubation at different concentrations and time intervals (FIG. 72B). Cell viabilities remained above 90% after being treated with 0.01, 0.1, and 1 µg/mL AIE dots within the tested periods of time. After being treated with a higher concentration (10 gig/mL) AIE dots for 24 or 48 hours, ~90% was still maintained, indicative of low cytotoxicity of the AIE dots.

Figure 73:
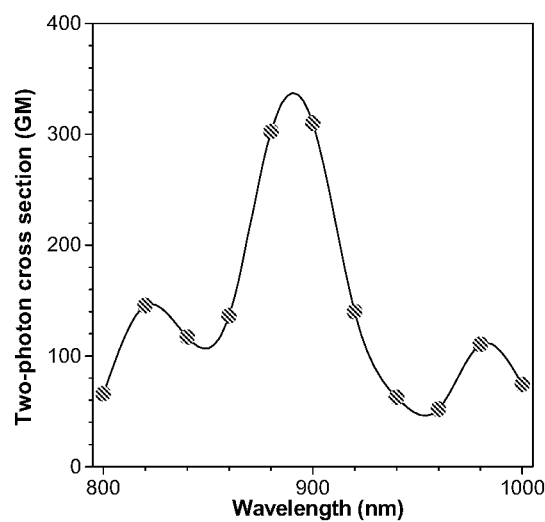
FIG. 73 shows two-photon cross section of TTS in THF/water suspension ($f_w$=99% water) with a concentration of 10 µM at different excitation wavelength.

The TPA spectrum of AIE dots in water with the wavelength range from 800-1000 nm at 20 nm intervals was investigated. The TTS molecule in aggregate shows efficient two-photon absorption properties, giving a high maximum δ value of 310 GM and a high quantum efficiency of 38.5% relative to rhodamine B ($\Phi_F$=41.9% in methanol) under excitation of a 900 nm laser light (FIG. 73). Moreover, a 900 nm fs laser expects to have deeper penetration and better focusing capability than the commonly used 770-860 nm Ti:Sapphire fs laser. Therefore, the TTS dots are a promising candidate for two-photon deep-tissue in vivo bioimaging.

Figure 74:
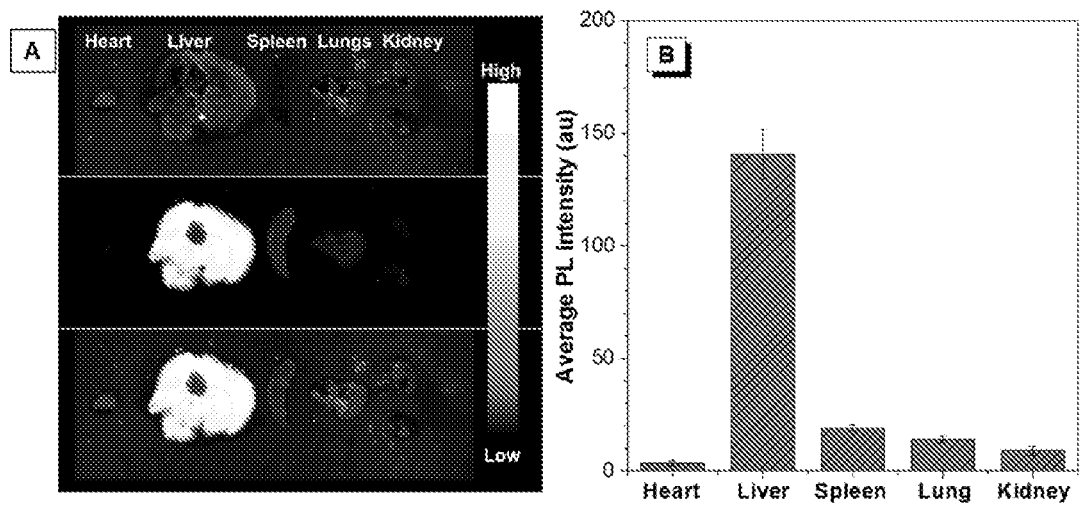
FIG. 74 shows (A) fluorescent image of the mouse after dissection. (B) Ex vivo one-photon confocal fluorescent images and two-photon confocal fluorescent images of the liver of a mouse intravenously injected TTS dots. (C) Quantitative fluorescence intensity distribution of the liver from the mice sacrificed at 3 hours post-injection with TTS dots at different penetration depth from 0 to 300 µm.
Figure 75:
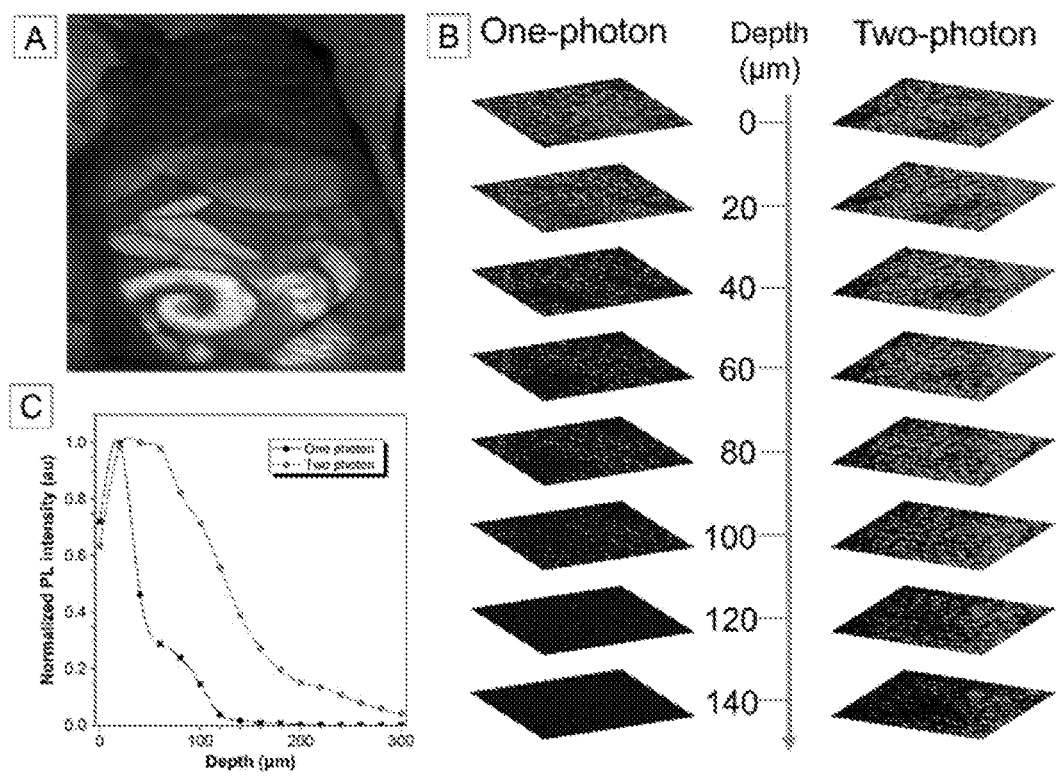
FIG. 75 shows (A) the ex vivo bright field (up), fluorescent images (middle) and overlay images (down) of the major organs (heart, liver, spleen, lungs and kidney) of the sacrificed mice at 3 hours post-injection with TTS dots. (B) Average fluorescence intensity distribution for internal organs from mice sacrificed at 3 hours post-injection with TTS dots.

To study the biodistribution of AIE-dots in mice, AIE-dots were intravenously injected from a tail vein. Major organs of the mouse including heart, liver, spleen, lungs, and kidney were resected at 3 hours post-injection and imaged immediately (FIG. 74A). Due to the metabolic functions of the mouse, the average fluorescence intensity of the AIE-dots mainly appears in the liver (FIG. 74B). To obtain further proof, the excised liver was imaged using one-photon excitation (FIG. 75A) and two-photon excitation. Using one-photon microscopy, the strong fluorescence from AIE dots was observed in the liver at a penetration depth of ~40 µm. However, it quickly faded out at a depth of ~80 µm and disappeared at a penetration depth of ~120 µm because of the significant absorption/scattering loss of the 488 nm excitation in the liver (FIGS. 75B-C). In contrast, the deeper penetration (>200 µm) and milder decay rate of fluorescence was achieved with two-photon excitation (FIGS. 75B-C). Therefore, the two-photon fluorescence imaging technique is more advantageous for deep-tissue imaging with higher penetration depth.

Figure 76:
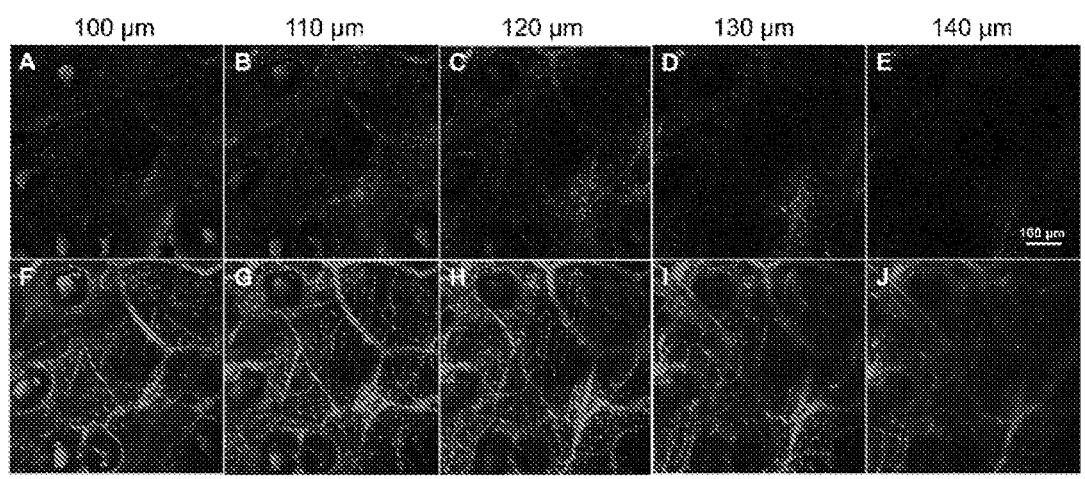
FIG. 76 shows (A-E) one-photon confocal luminescence and (F-J) two-photon scanning luminescence images of the intravenously injected TTS dots in the blood vessel of the ear of a mouse (penetration depth: 100-140 µm). Scale bar: 100 µm.
Figure 77:
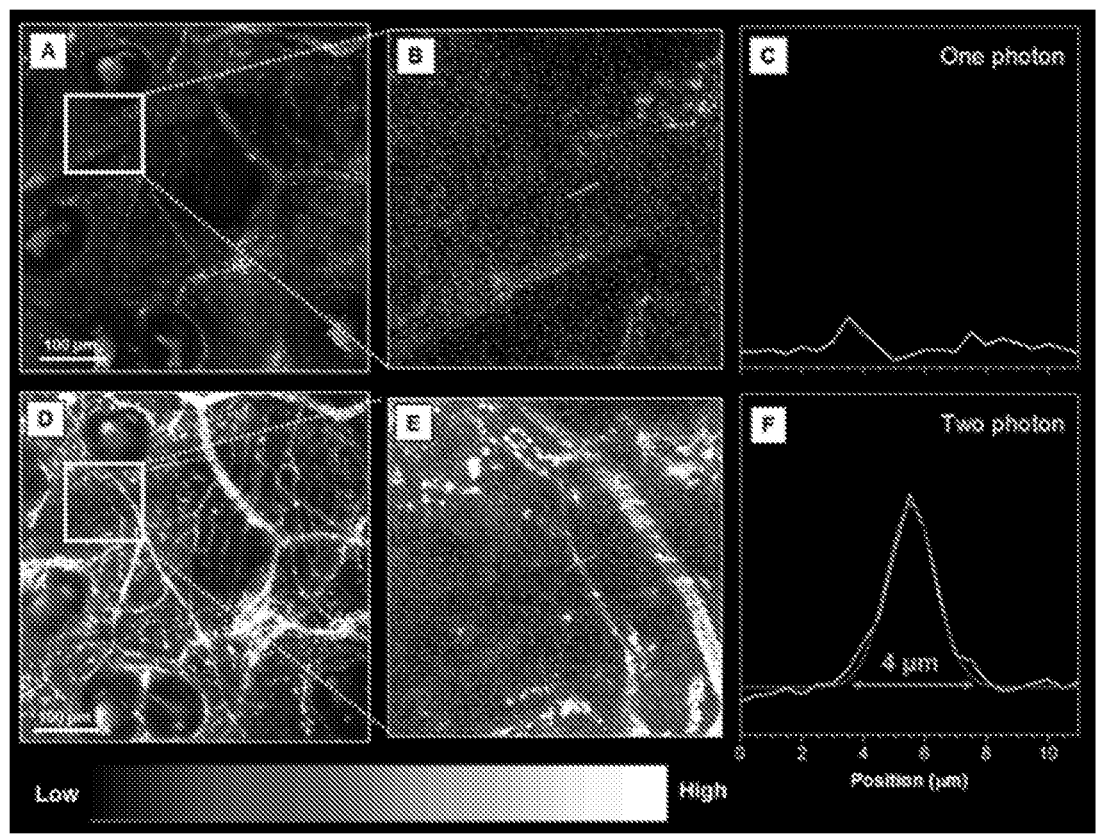
FIG. 77 shows (A) one-photon fluorescent images (pseudo-color) of the blood vessel of the ear of the mouse after intravenously injection of TTS dots (z-stage at 110 µm). (B) A zoom-in image of the selected zone in A. (C) A cross-sectional intensity profile measured along the green line in B. (D) Two-photon fluorescent images (pseudo-color) of the blood vessel of the ear of the mouse after intravenously injection of TTS dots (z-stage at 110 µm). (E) A zoom-in image of the selected zone in D. (F) A cross-sectional intensity profile measured along the green line in E. Scale bar: 100 µm.

One-photon and two-photon blood vasculature imaging in a live mouse ear was investigated using AIE dots (FIG. 76). The red fluorescence was observed from the small capillaries at a depth of 100-140 µm. However, with the increase of depth, the two-photon signal shows an obvious advantage over the one-photon signal with a much milder signal decay rate. For further comparison of signal difference between the one-photon and two-photon techniques, images at 110 µm were selected with pseudo-color. For one photon excitation, the signal contrast was low, indicated by the ambiguous signal from small capillaries and surrounding tissue (FIGS. 77A-C). In comparison, the image contrast was substantially improved using the two-photon technique. After careful measurement (FIGS. 77D-F), the quantitative measurement of the diameter of the indicated tiny capillary was ~4 µm in the deep location (110 µm). This is believed to be the first report using AIE dots for the accurate measurement of capillary diameter of a mouse ear. Therefore, compared to the one-photon imaging technique, the two-photon imaging technique enables observation of finer details of the tiny capillaries with a high signal-to-noise ratio.

Figure 78:
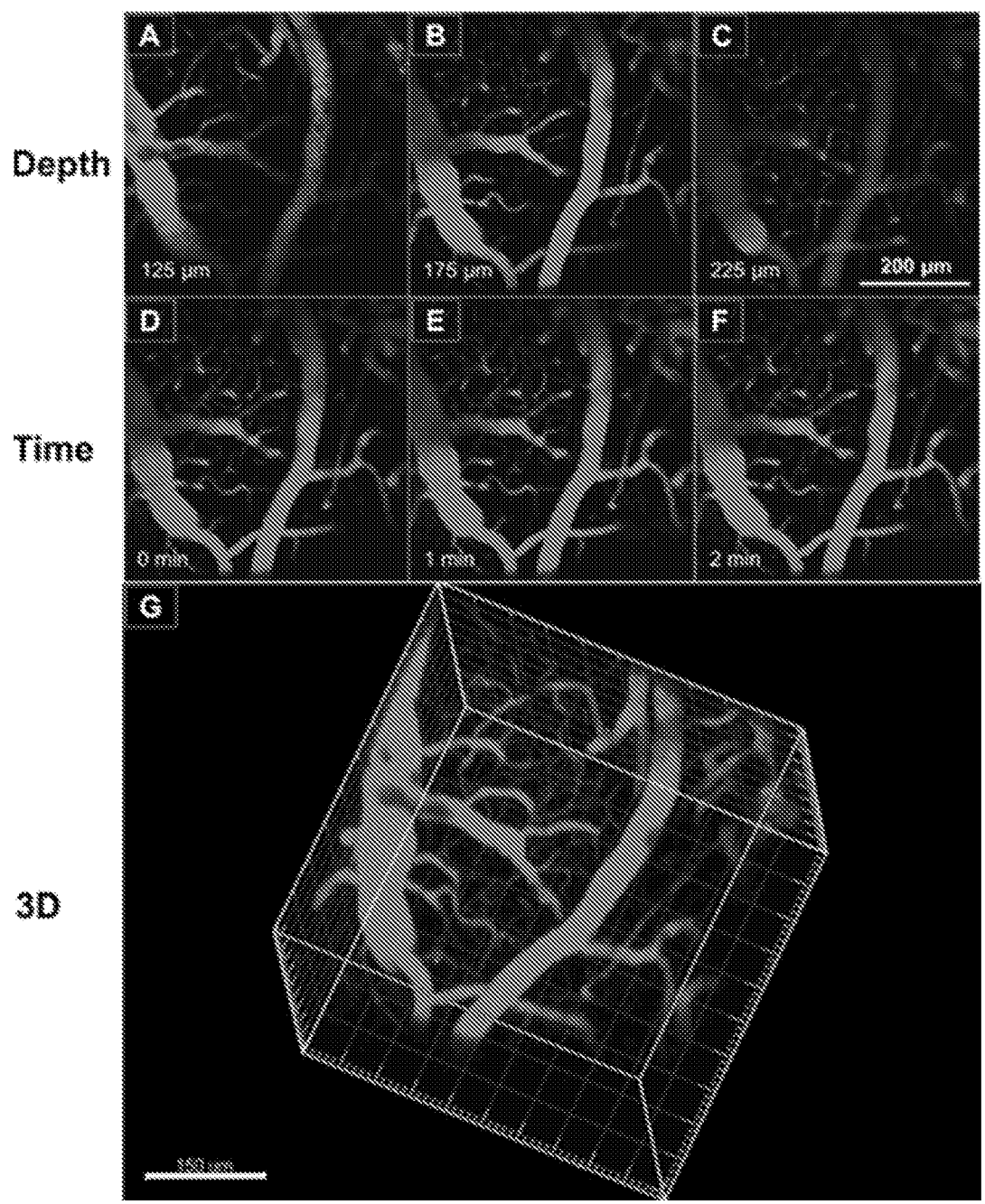
FIG. 78 shows (A-C) representative two-photon fluorescent images of the brain blood vessels of a mouse after 0.5 h injection of the TTS dots with different penetration depths. (D-F) Representative time-lapse images of the brain blood vessels of a mouse after 0.5 hour injection of the TTS dots at different monitoring time points at depth of 200 µm. Scale bar: 200 µm. (G) The reconstructed 3D image of the blood vessels of the mouse brain after 0.5 hour injection of the TTS dots. Scale bar: 150 µm.

Because TTS dots enable deep penetration and high contrast imaging by the two-photon technique, TTS dots were further exploited in real-time imaging of blood vessels at a deeper level of a mouse brain. FIGS. 78A-C show representative images of the mouse brain vasculature imaged through a cranial window at a penetration depth from 125-225 µm. The fluorescence signal from the AIE-dots was still detectable up to 350 µm. FIGS. 78D-F are representative high contrast images of the mouse brain vasculature at different designed time intervals. The dynamic real-time blood flow process in major blood vessels, even in other smaller capillaries, could be accurately and vividly displayed by intense red fluorescence from AIE dots. A high resolution 3D in vivo image was reconstructed (FIG. 78G), which provides a general and clear spatial picture about major blood vasculature networks, as well as the details of tiny capillaries. Thus, AIE dots have successfully realized real-time monitoring of the dynamic blood flow process in vivo with high spatial and temporal resolution.

EXAMPLES

Synthesis of MTPE-TP

The synthesis of MTPE-TP is shown below in Scheme 1.

Scheme 1: Synthetic route to MTPE-TP

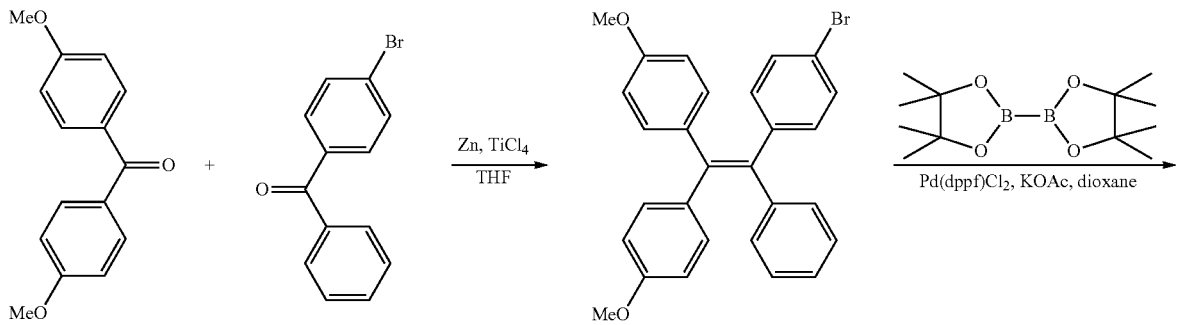

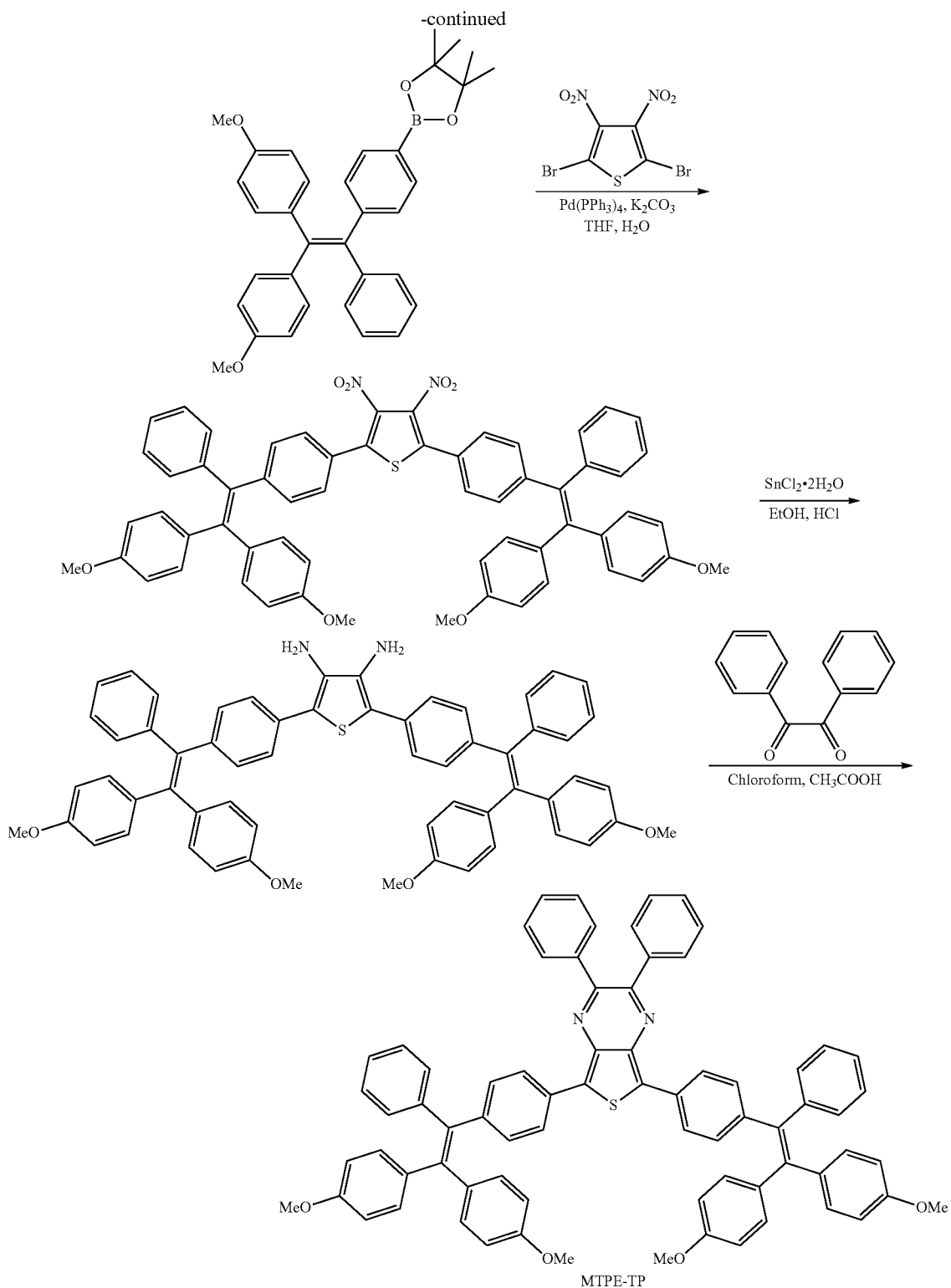

MTPE-TP 4,4'-dimethoxybenzophenone (20 mmol, 4.84 g), 4-bromobenzophenone (24 mmol, 6.26 g) and zinc dust (80 mmol, 5.2 g) were added to a 500 mL round-bottom flask. Then the flask was evacuated under vacuum and flushed with dry nitrogen three times. After addition of 250 mL of anhydrous THF, the mixture was cooled to −10° C. and TiCl$_4$ (7.7 mL, 70 mmol) was added dropwise and stirred for 30 minutes. The mixture was heated to reflux and stirred for 12 hours. After cooling to room temperature, the reaction was quenched by 1 M HCl solution, and the mixture was extracted with dichloromethane three times. The organic phase was combined, dried with MgSO$_4$, and the solvent was evaporated under reduced pressure. The crude product was purified on a silica gel column chromatography using dichloromethane/hexane (v/v 1:5) as the eluent to give 4,4'-(2-(4-bromophenyl)-2-phenylethene-1,1-diyl)bis(methoxybenzene) as a white solid (46% yield).

4,4'-(2-(4-Bromophenyl)-2-phenylethene-1,1-diyl)bis(methoxybenzene) (3.77 g, 8 mmol), [1,1'-bis(diphenylphosphino)ferrocene]dichloropalladium (II) (Pd(dppf)Cl$_2$) (0.22 g, 0.3 mmol), KOAc (3.0 g, 30 mmol), and bis(pinacolato)diboron (3.05 g, 12 mmol) were added into a 100 mL two-necked round-bottom flask, and the flask was evacuated under vacuum and flushed with dry nitrogen for three times. Anhydrous 1,4-dioxane (40 mL) was added, and the mixture was heated to reflux and stirred under nitrogen atmosphere for 24 hours. Afterwards, water was added, and the mixture was washed with dichloromethane three times. The organic phase was combined, dried with MgSO$_4$, and the solvent was evaporated under reduced pressure. The crude product was purified by silica gel column chromatography using dichloromethane/hexane (v/v 1:3) as the eluent to afford 2-(4-(2,2-bis(4-methoxyphenyl)-1-phenylvinyl)phenyl)-4,4,5,5-tetramethyl-1,3,2-dioxaborolane as a white solid (85% yield).

2-(4-(2,2-Bis(4-methoxyphenyl)-1-phenylvinyl)phenyl)-4,4,5,5-tetramethyl-1,3,2-dioxaborolane (2.59 g, 5 mmol), 2,5-dibromo-3,4-dinitrothiophene (0.67 g, 2 mmol), tetrakis(triphenylphosphine)palladium (0) (Pd(PPh$_3$)$_4$) (60 mg, 0.05 mmol), and K$_2$CO$_3$ (2.07 g, 15 mmol) were added into a 100 mL two-necked round-bottom flask. The flask was vacuumed and purged with dry nitrogen three times. Then anhydrous tetrahydrofuran (40 mL) and water (10 mL) were added, and the mixture was heated to reflux and stirred under nitrogen atmosphere for 24 hours in the absence of light. Afterwards, water was added, and the mixture was extracted with dichloromethane. The organic phase was combined and dried with MgSO$_4$. After the removal of the solvent under reduced pressure, the residue was purified by silica gel column chromatography using dichloromethane/hexane (v/v 1:3) as the eluent to result in 2,5-bis(4-(2,2-bis(4-methoxyphenyl)-1-phenylvinyl)phenyl)-3,4-dinitrothiophene as an orange solid (81% yield).

2,5-Bis(4-(2,2-bis(4-methoxyphenyl)-1-phenylvinyl)phenyl)-3,4-dinitrothiophene (1.43 g, 1.5 mmol) was suspended in a solution of 30 mL of ethanol and 20 mL of concentrated HCl under vigorous stirring, and SnCl$_2$.2H$_2$O (6.75 g, 30 mmol) was added into the mixture in three portions. Then the mixture was heated to reflux and stirred under nitrogen atmosphere for 20 hours. After cooling to room temperature, 100 mL of water was added. The suspension was filtered through to give 2,5-bis(4-(2,2-bis(4-methoxyphenyl)-1-phenylvinyl)phenyl)thiophene-3,4-diamine as a yellow-organic solid, and it was used without further purification.

2,5-Bis(4-(2,2-bis(4-methoxyphenyl)-1-phenylvinyl)phenyl)thiophene-3,4-diamine (1.07 g, 1.2 mmol) was dissolved in chloroform (20 mL) and acetic acid (20 mL), and benzil (0.32 g, 1.5 mmol) was added. The mixture was heated to reflux and stirred for 18 hours. After cooling to room temperature, water was added to the solution, and the mixture was extracted with dichloromethane three times. The organic phase was washed with brine several times, and dried with MgSO$_4$. After the removal of the solvent under reduced pressure, the residue was purified by silica gel column chromatography using dichloromethane/hexane (v/v 1:3) as the eluent to result in 5,7-bis(4-(2,2-bis(4-methoxyphenyl)-1-phenylvinyl)phenyl)-2,3-diphenylthieno[3,4-b']pyrazine (MTPE-TP) as a dark purple solid (81% yield).

$^1$H NMR (400 MHz, CDCl$_3$, δ, ppm): 8.07 (d, 4H), 7.50 (d, 4H), 7.37-7.27 (m, 6H), 7.17-7.05 (m, 14H), 7.02 (d, 4H), 6.95 (d, 4H), 6.66 (dd, 8H), 3.74 (d, 12H). $^{13}$C NMR (100 MHz, CDCl$_3$, δ, ppm): 158.29, 158.12, 152.17, 144.23, 143.91, 140.57, 139.30, 138.79, 136.42, 136.31, 132.70, 132.68, 131.95, 131.61, 131.19, 131.05, 129.87, 128.84, 128.07, 127.77, 126.81, 126.20, 113.22, 113.00, 55.11. HRMS (MALDI) m/z calcd for C$_{74}$H$_{56}$O$_4$N$_2$S 1068.3961, found 1068.3969.

Synthesis of MTPE-TT

The synthesis of MTPE-TT is shown below in Scheme 2.

Scheme 2: Synthetic route to MTPE-TT

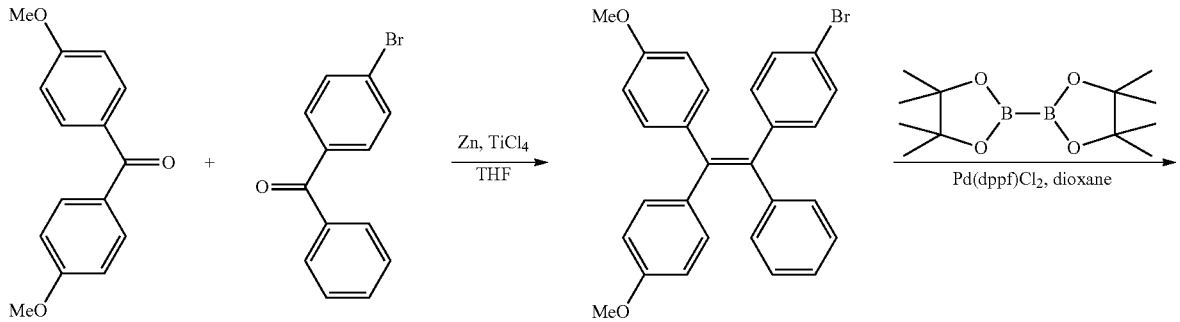

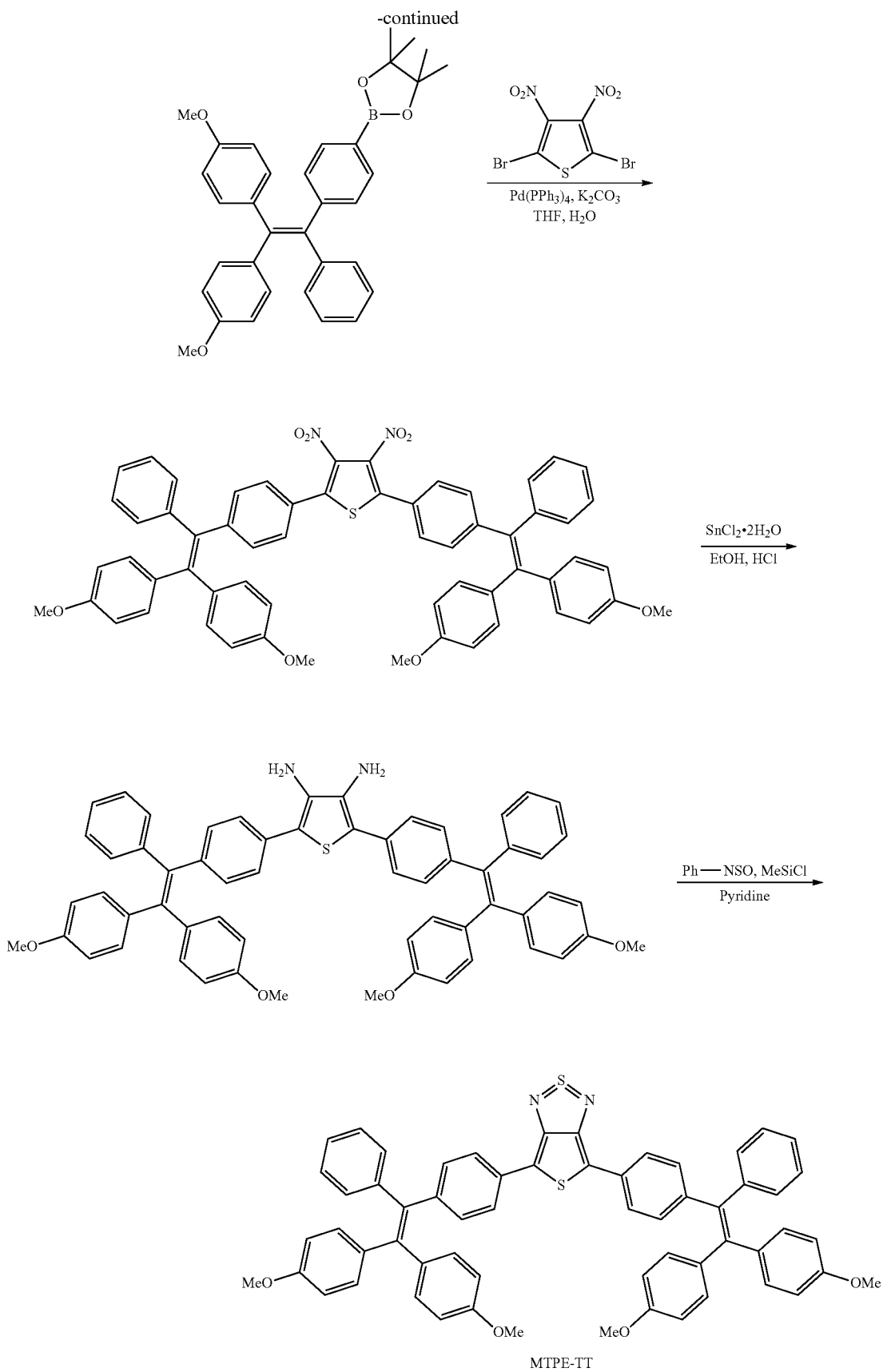

2,5-Bis(4-(2,2-bis(4-methoxyphenyl)-1-phenylvinyl)phenyl)thiophene-3,4-diamine (0.9 g, 1 mmol) was dissolved in dry pyridine (35 mL) under nitrogen atmosphere. Then N-thionylaniline (0.225 mL, 2 mmol) and $Me_3SiCl$ (0.23 mL, 1.8 mmol) were added into this solution. The reaction continued at 80° C. for 18 hours. Most of the pyridine was evaporated and the residue was purified by silica gel column chromatography on silica gel using dichloromethane/hexane (v/v 1:3) as the eluent to give 5,7-bis(4-(2,2-bis(4-methoxyphenyl)-1-phenylvinyl)phenyl)-2,3-diphenylthieno[3,4-b][1,2,5]thia diazole (MTPE-TT) as a dark blue solid (76% yield).

$^1$H NMR (400 MHz, $CDCl_3$, δ, ppm): 7.85 (d, 4H), 7.16-7.04 (m, 14H), 7.01 (d, 4H), 6.94 (d, 4H), 6.65 (dd, 8H), 3.74 (d, 12H). $^{13}$C NMR (100 MHz, $CDCl_3$, δ, ppm): 158.31, 158.16, 157.49, 144.08, 143.73, 140.72, 138.63, 136.30, 136.28, 132.65, 132.21, 131.52, 130.49, 127.80, 126.26, 124.96, 118.77, 113.25, 113.01, 55.10. HRMS (MALDI) m/z calcd for $C_{60}H_{46}O_4N_2S_2$ 922.2857, found 922.2899.

Synthesis of TPE-TPA-TT

The synthesis of TPE-TPA-TT is shown below in Scheme 3.

Scheme 3: Synthetic route to TPE-TPA-TT

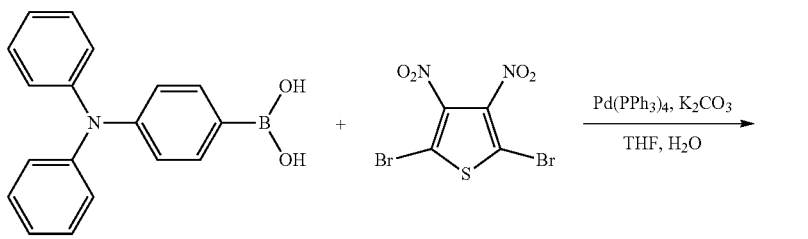

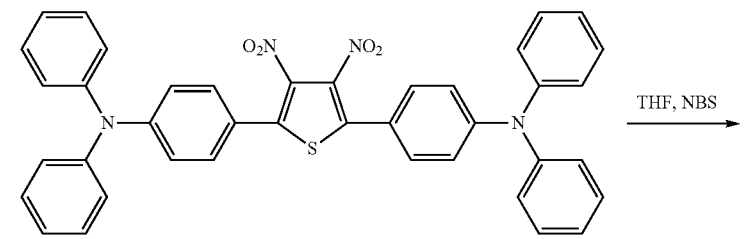

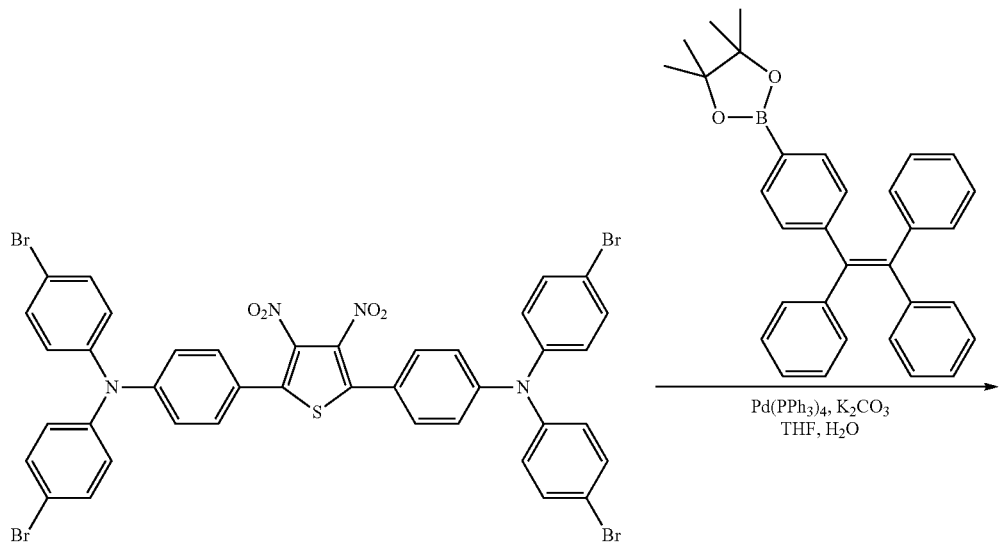

-continued
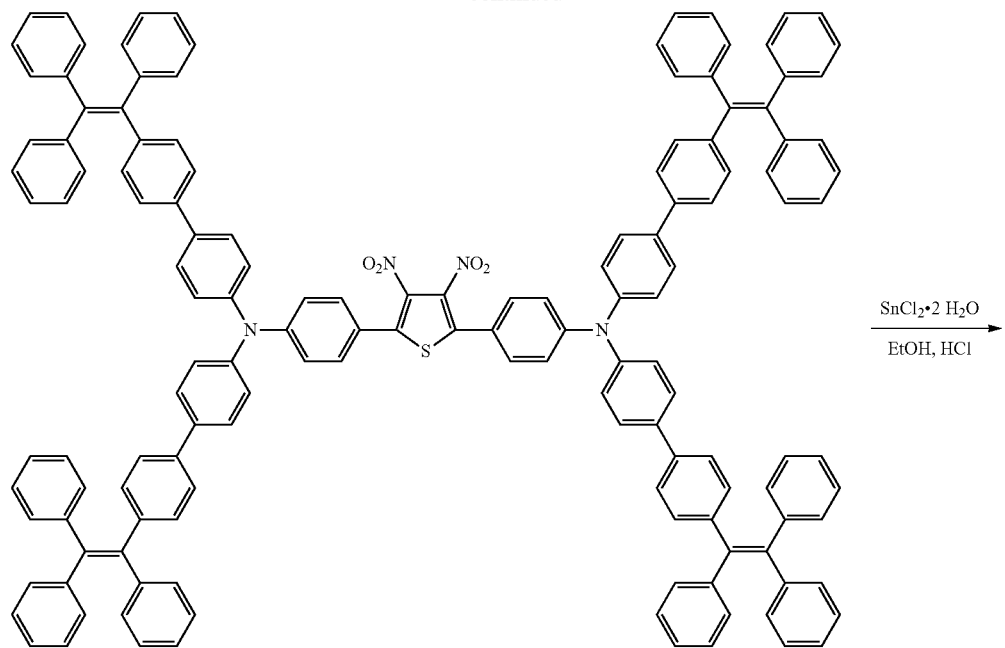
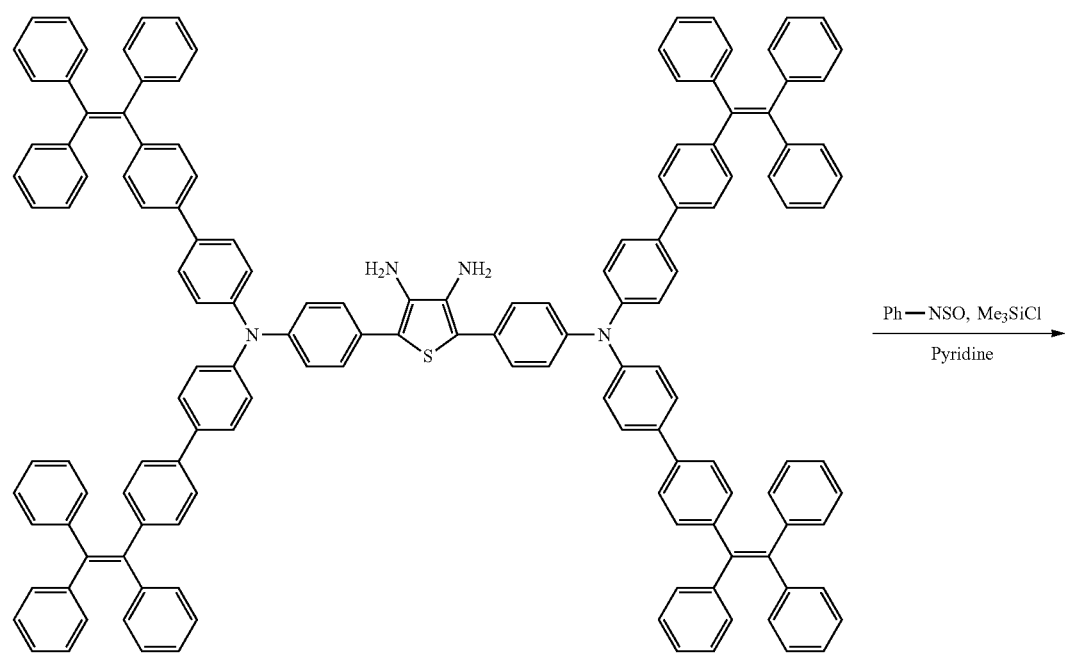

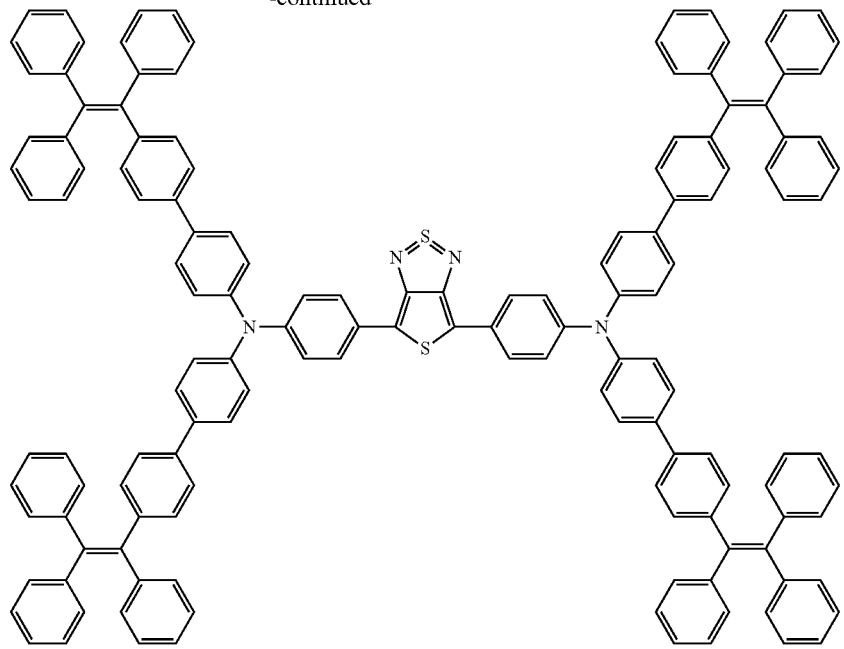

TPE-TPA-TT 4-(Diphenylamino)phenyl)boronic acid (2.89 g, 10 mmol), 2,5-dibromo-3,4-dinitrothiophene (1.33 g, 4 mmol), Pd(PPh$_3$)$_4$ (93 mg, 0.08 mmol), and K$_2$CO$_3$ (4.14 g, 30 mmol) were added into a 250 mL two-necked round-bottom flask. The flask was vacuumed and purged with dry nitrogen three times. Then anhydrous tetrahydrofuran (80 mL) and water (20 mL) were added, and the mixture was heated to reflux and stirred under nitrogen atmosphere for 24 hours in the absence of light. After cooling to room temperature, water was added, and the mixture was extracted with dichloromethane. The organic phase was combined, and dried with MgSO$_4$. After the removal of the solvent under reduced pressure, the residue was purified by silica gel column chromatography using dichloromethane/hexane (v/v 1:4) as the eluent to result in 4,4'-(3,4-dinitrothiophene-2,5-diyl)bis (N,N-diphenylaniline) as a red solid (81% yield).

4,4'-(3,4-Dinitrothiophene-2,5-diyl)bis(N,N-diphenylaniline) (1.98 g, 3 mmol) and anhydrous tetrahydrofuran (80 mL) were added into a 250 mL two-necked round-bottom flask. N-Bromosuccinimide (NBS, 2.97 g, 15 mmol) was added into the solution in three portions, and the mixture was stirred at room temperature in the absent of light. Thin layer chromatography (TLC) was used to monitor the reaction process. When the reaction was completed, aqueous NaHCO$_3$ solution was added into the mixture. The solution was extracted with dichloromethane three times. The organic phase was combined and dried with MgSO$_4$. After removal of the solvent under reduced pressure, the residue was purified by silica gel column chromatography using dichloromethane/hexane (v/v 1:4) as the eluent to result in 4,4'-(3,4-dinitrothiophene-2,5-diyl)bis(N,N-bis(4-bromophenyl)aniline) as a red solid (92% yield).

4,4'-(3,4-Dinitrothiophene-2,5-diyl)bis(N,N-bis(4-bromophenyl)aniline) (2.44 g, 2.5 mmol), 4,4,5,5-tetramethyl-2-(4-(1,2,2-triphenylvinyl)phenyl)-1,3,2-dioxaborolane (5.50 g, 12 mmol), Pd(PPh$_3$)$_4$ (230 mg, 0.2 mmol), and K$_2$CO$_3$ (4.14 g, 30 mmol) were added into a 250 mL two-necked round-bottom flask. The flask was vacuumed and purged with dry nitrogen three times. Then anhydrous tetrahydrofuran (60 mL) and water (15 mL) were added, and the mixture was heated to reflux and stirred under nitrogen atmosphere for 24 hours in the absence of light. After cooling to room temperature, water was added, and the mixture was extracted with dichloromethane three times. The organic phase was combined, and dried with MgSO$_4$. After the removal of the solvent under reduced pressure, the residue was purified by silica gel column chromatography using dichloromethane/hexane (v/v 1:4) as the eluent to result in N,N'-((3,4-dinitrothiophene-2,5-diyl)bis(4,1-phenylene))bis(4'-(1,2,2-triphenylvinyl)-N-(4'-(1,2,2-triphenylvinyl)-[1,1'-biphenyl]-4-yl)-[1,1'-biphenyl]-4-amine) as a red solid (78% yield).

N,N'-((3,4-dinitrothiophene-2,5-diyl)bis(4,1-phenylene))bis(4'-(1,2,2-triphenylvinyl)-N-(4'-(1,2,2-triphenylvinyl)-[1,1'-biphenyl]-4-yl)-[1,1'-biphenyl]-4-amine) (2.97 g, 1.5 mmol) was suspended in a solution of 60 mL of ethanol and 40 mL of concentrated HCl under vigorous stirring in a 250 mL two-necked round-bottom flask, and SnCl$_2$.2H$_2$O (6.75 g, 30 mmol) was added in three portions. Then the mixture was heated to reflux and stirred under nitrogen atmosphere for 20 hours. After cooling to room temperature, 150 mL of water was added. The suspension was filtered through to give 2,5-bis(4-(bis(4'-(1,2,2-triphenylvinyl)-[1,1'-biphenyl]-4-yl)amino)phenyl)thiophene-3,4-diamine as a yellow-organic solid, and it was used without further purification.

2,5-Bis(4-(bis(4'-(1,2,2-triphenylvinyl)-[1,1'-biphenyl]-4-yl)amino)phenyl)thiophene-3,4-diamine (1.92 g, 1 mmol) was dissolved in dry pyridine (35 mL) under nitrogen. N-thionylaniline (0.225 mL, 2 mmol) and Me$_3$SiCl (0.23 mL, 1.8 mmol) were added to this solution. The reaction continued at 80° C. for 18 hours. Most of the pyridine was evaporated and the residue was purified by silica gel column chromatography using dichloromethane/hexane (v/v 1:4) as the eluent to give N,N'-(thieno[3,4-b][1,2,5]thiadiazole-5,7- diylbis(4,1-phenylene))bis(4'-(1,2,2-triphenylvinyl)-N-(4'-(1,2,2-triphenylvinyl)-[1,1'-biphenyl]-4-yl)-[1,1'-biphenyl]-4-amine) (TPE-TPA-TT) as a blue solid (71% yield).
$^1$H NMR (400 MHz, CDCl$_3$, δ, ppm): 7.98 (d, 4H), 7.48 (d, 8H), 7.34 (d, 8H), 7.17 (d, 12H), 7.14-7.01 (m, 68H). $^{13}$C NMR (100 MHz, CDCl$_3$, δ, ppm): 157.21, 146.52, 146.25, 143.80, 143.78, 143.75, 142.53, 141.08, 140.57, 138.09, 135.51, 131.85, 131.44, 131.38, 127.78, 127.70, 127.66, 127.35, 126.66, 126.50, 126.44, 125.75, 124.74, 123.92, 117.71. HRMS (MALDI) m/z calcd for C$_{144}$H$_{110}$N$_4$S$_2$ 1949.7423, found 1949.7253.
Synthesis of PTZ-BT-TPA
The synthesis of PTZ-BT-TPA is shown below in Scheme 4.
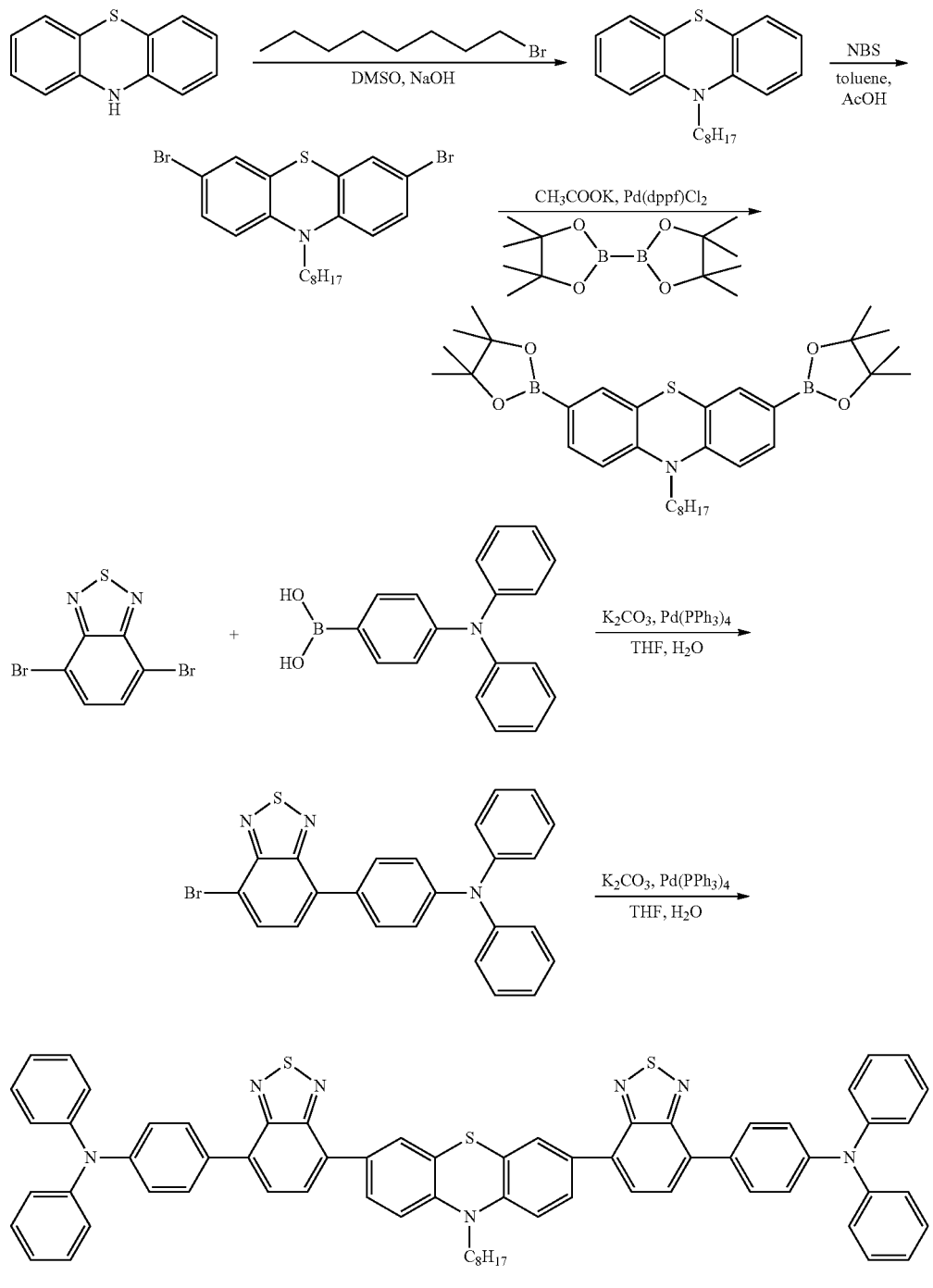
Scheme 4: Synthetic route to PTZ-BT-TPA
PTZ-BT-TPA 10H-phenothiazine (10 g, 50 mmol), 1-bromooctane (11.6 g, 60 mmol), sodium hydroxide (12 g, 300 mmol), and dimethyl sulfoxide (DMSO) (100 mL) were added into a 250 mL two-necked round-bottom flask, and the mixture was stirred at room temperature for 2 days. Then brine was added, and the mixture was extracted with ethyl acetate three times. The organic phase was combined and dried with MgSO$_4$. After removal of the solvent under reduced pressure, the residue was purified by silica gel column chromatography using dichloromethane/hexane (v/v 1:4) as the eluent to result in 10-octyl-10H-phenothiazine as a colorless oil (86% yield).

NBS (7.83 g, 44 mmol) was added to a solution of 10-octyl-10H-phenothiazine (6.23 g, 20 mmol) in toluene (20 mL) and acetic acid (70 mL). The reaction mixture was stirred for 3 hours at room temperature in the absent of light. Water was added to stop the reaction, and the mixture was extracted with ethyl acetate three times. The organic phase was combined and dried with MgSO$_4$. After removal of the solvent under reduced pressure, the residue was purified by silica gel column chromatography using dichloromethane/hexane (v/v 1:3) as the eluent to result in 3,7-dibromo-10-octyl-10H-phenothiazine as a viscous oil (91% yield).

3,7-Dibromo-10-octyl-10H-phenothiazine (2.35 g, 5 mmol), bis(pinacolato)diboron (3.18 g, 12.5 mmol), PdCl$_2$(dppf) (163 mg, 0.2 mmol), and KOAc (1.96 g, 20 mmol) were added into a 100 mL two-necked round-bottom flask. The flask was vacuumed and purged with dry nitrogen three times. Then anhydrous 1,4-dioxane (40 mL) was added, and the mixture was heated to 90° C. and stirred for 24 hours in the absence of light. Afterwards, water was added, and the mixture was extracted with dichloromethane. The organic phase was combined and dried with MgSO$_4$. After removal of the solvent under reduced pressure, the residue was purified by silica gel column chromatography using dichloromethane/hexane (v/v 1:2) as the eluent to result in 10-octyl-3,7-bis(4,4,5,5-tetramethyl-1,3,2-dioxaborolan-2-yl)-10H-phenothiazine as a colorless solid (91% yield).

4-(Diphenylamino)phenyl)boronic acid (2.89 g, 10 mmol), 4,7-dibromobenzo[c][1,2,5]thiadiazole (3.53 g, 12 mmol), Pd(PPh$_3$)$_4$ (120 mg, 0.1 mmol), and K$_2$CO$_3$ (2.76 g, 20 mmol) were added into a 250 mL two-necked round-bottom flask. The flask was vacuumed and purged with dry nitrogen three times. Then anhydrous tetrahydrofuran (80 mL) and water (20 mL) were added, and the mixture was heated to reflux and stirred for 24 hours in the absence of light. After cooling to room temperature, water was added, and the mixture was extracted with dichloromethane. The organic phase was combined and dried with MgSO$_4$. After removal of the solvent under reduced pressure, the residue was purified by silica gel column chromatography using dichloromethane/hexane (v/v 1:4) as the eluent to result in 4-(7-bromobenzo[c][1,2,5]thiadiazol-4-yl)-N,N-diphenylaniline as a red solid (72% yield).

4-(7-Bromobenzo[c][1,2,5]thiadiazol-4-yl)-N,N-diphenylaniline (2.29 g, 5 mmol), 10-octyl-3,7-bis(4,4,5,5-tetramethyl-1,3,2-dioxaborolan-2-yl)-10H-phenothiazine (1.13 g, 2 mmol), Pd(PPh$_3$)$_4$ (60 mg, 0.05 mmol), and K$_2$CO$_3$ (2.76 g, 20 mmol) were added into a 100 mL two-necked round-bottom flask. The flask was vacuumed and purged with dry nitrogen three times. Then anhydrous tetrahydrofuran (40 mL) and water (10 mL) were added, and the mixture was heated to reflux and stirred for 24 hours in the absence of light. After cooling to room temperature, water was added, and the mixture was extracted with dichloromethane. The organic phase was combined and dried with MgSO$_4$. After removal of the solvent under reduced pressure, the residue was purified by silica gel column chromatography using dichloromethane/hexane (v/v 1:3) as the eluent to result in 4,4'-((10-octyl-10H-phenothiazine-3,7-diyl)bis(benzo[c][1,2,5]thiadiazole-7,4-diyl))bis(N,N-diphenylaniline) (PTZ-BT-TPA) as a red solid (78% yield).

$^1$H NMR (400 MHz, CDCl$_3$, δ, ppm): 7.92-7.82 (m, 6H), 7.79 (d, 2H), 7.73 (s, 4H), 7.34-7.26 (m, 8H), 7.24-7.15 (m, 12H), 7.10-7.01 (m, 6H), 3.98 (t, 2H), 2.00-1.87 (m, 2H), 1.54-1.45 (m, 2H), 1.41-1.23 (m, 8H), 0.88 (t, 3H). $^{13}$C NMR (100 MHz, CDCl$_3$, δ, ppm): 154.11, 154.04, 148.02, 147.49, 144.80, 132.41, 131.79, 131.32, 130.94, 129.92, 129.38, 128.31, 127.80, 127.37, 127.22, 124.92, 124.39, 123.32, 122.91, 115.20, 47.80, 31.80, 31.61, 29.30, 27.09, 26.92, 22.67, 14.15. HRMS (MALDI) m/z calcd for C$_{68}$H$_{55}$N$_7$S$_3$ 1065.3681, found 1065.3640.

Synthesis of NPB-TQ

The synthesis of NPB-TQ is shown below in Scheme 5.

Scheme 5: Synthetic route to NPB-TQ

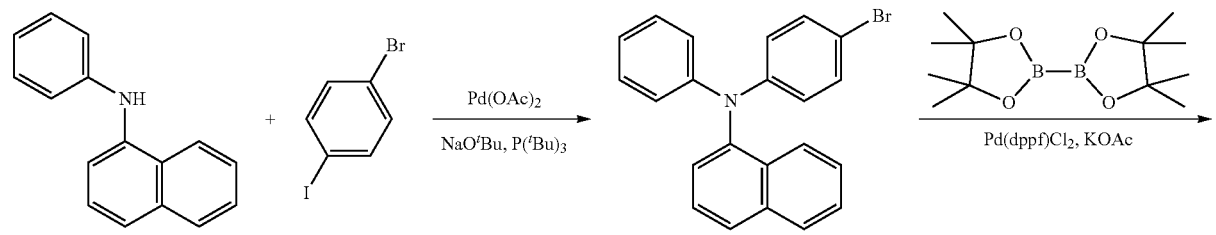

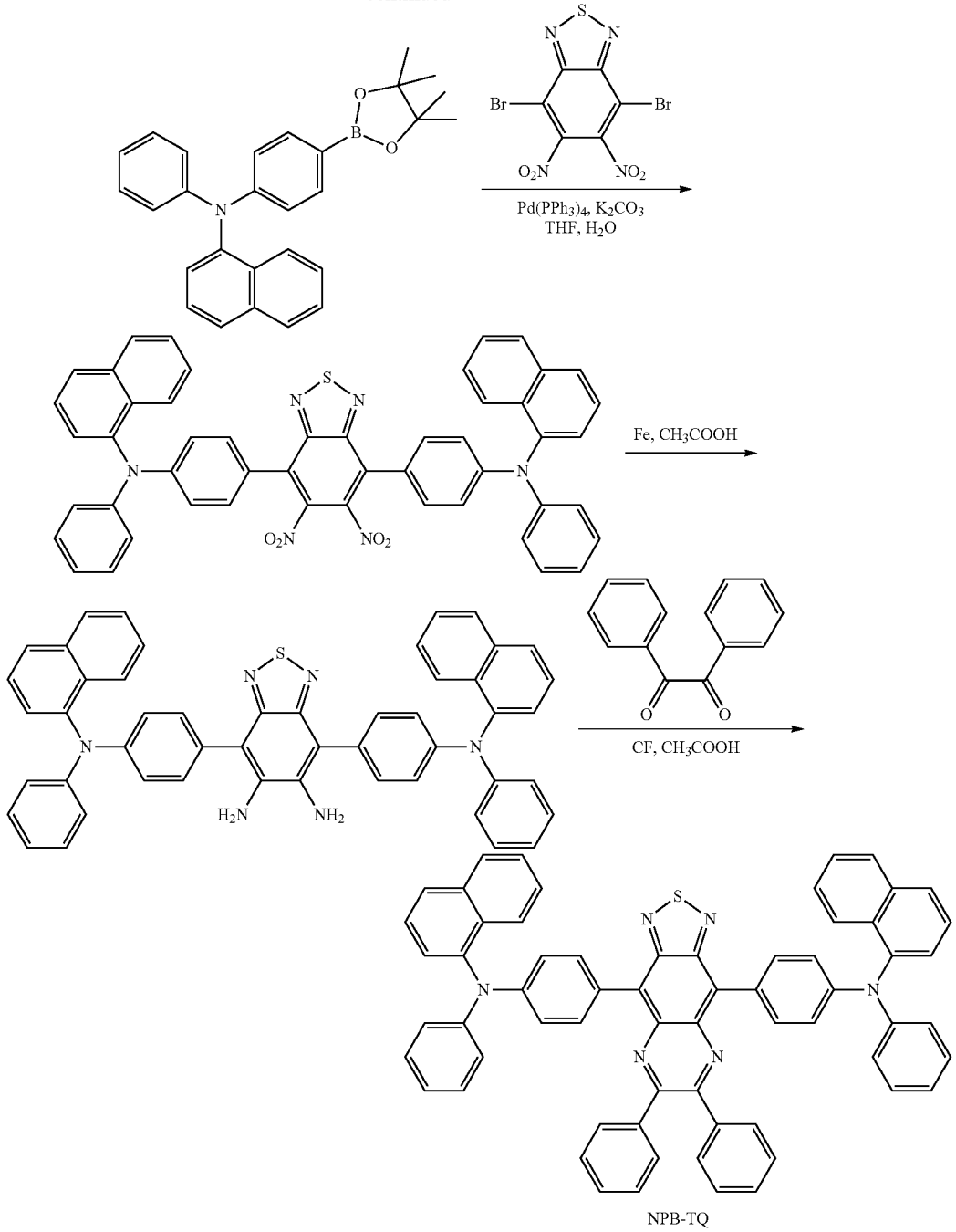

N-phenylnaphthalen-1-amine (5.28 g, 24 mmol), 1-bromo-4-iodobenzene (5.66 g, 20 mmol), sodium tert-butoxide (2.3 g, 24 mmol), and palladium (II) acetate (Pd(OAc)$_2$) (225 mg, 1 mmol) were added into a 250 mL two-necked round-bottom flask. The flask was vacuumed and purged with dry nitrogen three times. Then anhydrous toluene (60 mL) and tri-tert-butylphosphine ($^t$Bu$_3$P, 1.5 mmol, 1 M toluene solution, 1.5 mL) were added, and the mixture was heated to reflux and stirred for 24 hours in the absence of light. After cooling to room temperature, water was added, and the mixture was extracted with dichloromethane. The organic phase was combined and dried with MgSO$_4$. After removal of the solvent under reduced pressure, the residue was purified by column chromatography on silica gel using dichloromethane/hexane (v/v 1:5) as the eluent to result in N-(4-bromophenyl)-N-phenylnaphthalen-1-amine as a colorless solid (76% yield).

N-(4-Bromophenyl)-N-phenylnaphthalen-1-amine (5.61 g, 15 mmol), [1,1'-bis(diphenylphosphino)ferrocene]dichloropalladium (II) (Pd(dppf)Cl$_2$) (0.36 g, 0.5 mmol), KOAc (5.0 g, 50 mmol), and bis(pinacolato)diboron (6.1 g, 24 mmol) were added into a 250 mL two-necked round-bottom flask, and the flask was evacuated under vacuum and flushed with dry nitrogen three times. Anhydrous 1,4-dioxane (80 mL) was added, and the mixture was heated to reflux and stirred under nitrogen atmosphere for 24 hours. Afterwards, water was added, and the mixture was washed with dichloromethane three times. The organic phase was combined, dried with MgSO₄, and the solvent was evaporated under reduced pressure. The crude product was purified by silica gel column chromatography using dichloromethane/hexane (v/v 1:4) as the eluent to afford N-phenyl-N-(4-(4,4,5,5-tetramethyl-1,3,2-dioxaborolan-2-yl)phenyl)naphthalen-1-amine as a light yellow solid (83% yield).

N-phenyl-N-(4-(4,4,5,5-tetramethyl-1,3,2-dioxaborolan-2-yl)phenyl)naphthalen-1-amine (2.29 g, 5 mmol), 4,7-dibromo-5,6-dinitrobenzo[c][1,2,5]thiadiazole (0.77 g, 2 mmol), K₂CO₃ (2.76 g, 20 mmol), and Pd(PPh₃)₄ (120 mg, 0.1 mmol) were added into a 100 mL two-necked round-bottom flask. The flask was vacuumed and purged with dry nitrogen three times. Then anhydrous tetrahydrofuran (40 mL) and water (10 mL) were added, and the mixture was heated to reflux and stirred for 24 hours in the absence of light. After cooling to room temperature, water was added, and the mixture was extracted with dichloromethane three times. The organic phase was combined and dried with MgSO₄. After removal of the solvent under reduced pressure, the residue was purified by column chromatography on silica gel using dichloromethane/hexane (v/v 1:3) as the eluent to result in N,N'-((5,6-dinitrobenzo[c][1,2,5]thiadiazole-4,7-diyl)bis(4,1-phenylene))bis(N-phenylnaphthalen-1-amine) as a dark purple solid (81% yield).

N,N'-((5,6-dinitrobenzo[c][1,2,5]thiadiazole-4,7-diyl)bis(4,1-phenylene))bis(N-phenyl naphthalen-1-amine) (1.22 g, 1.5 mmol) was suspended in a solution of 50 mL of acetic acid under vigorous stirring in a 100 mL two-necked round-bottom flask, and iron power (2.24 g, 40 mmol) was added into the mixture. Then the mixture was heated to 80° C. and stirred for 12 hours. After cooling to room temperature, 100 mL of water was added, and the mixture was extracted with dichloromethane three times. The organic phase was combined, washed with aqueous NaHCO₃, and dried with MgSO₄. After removal of the solvent under reduced pressure, a dark solid of 4,7-bis(4-(naphthalen-1-yl(phenyl)amino)phenyl)benzo[c][1,2,5]thiadiazole-5,6-diamine was obtained, and it was used without further purification.

4,7-Bis(4-(naphthalen-1-yl(phenyl)amino)phenyl)benzo[c][1,2,5]thiadiazole-5,6-diamine (0.75 g, 1.0 mmol) was dissolved in chloroform (20 mL) and acetic acid (20 mL) in a 100 mL two-necked round-bottom flask under nitrogen. Benzil (0.32 g, 1.5 mmol) was added into this solution. The mixture was heated to 70° C. and stirred for 12 hours. After cooling to room temperature, 100 mL of water was added. The mixture was extracted with dichloromethane three times. The organic phase was combined, washed with aqueous NaHCO₃, and dried with MgSO₄. After removal of the solvent under reduced pressure, the residue was purified by column chromatography on silica gel using dichloromethane/hexane (v/v 1:3) as the eluent to result in N,N'-((6,7-diphenyl-[1,2,5]thiadiazolo[3,4-g]quinoxaline-4,9-diyl)bis(4,1-phenylene))bis(N-phenylnaphthalen-1-amine) (NPB-TQ) as a dark blue solid (75% yield).

¹H NMR (400 MHz, CDCl₃, δ, ppm): 8.07 (d, 2H), 7.96-7.89 (m, 6H), 7.83 (d, 2H), 7.61 (d, 4H), 7.55-7.46 (m, 6H), 7.42-7.34 (m, 4H), 7.31-7.23 (m, 12H), 7.21 (d, 4H), 7.06-6.97 (m, 2H). ¹³C NMR (100 MHz, CDCl₃, δ, ppm): 153.15, 152.58, 148.62, 147.88, 143.22, 138.58, 136.00, 135.34, 133.99, 131.39, 130.05, 129.46, 129.24, 128.49, 128.43, 128.16, 127.69, 127.34, 126.80, 126.58, 126.43, 126.23, 124.43, 123.13, 122.56, 119.52. HRMS (MALDI) m/z calcd for C₆₄H₄₂N₆S 926.3192, found 926.3170.

Synthesis of TPE-TQ-A

The synthesis of TPE-TQ-A is shown below in Scheme 6.

Scheme 6: Synthetic route to TPE-TQ-A

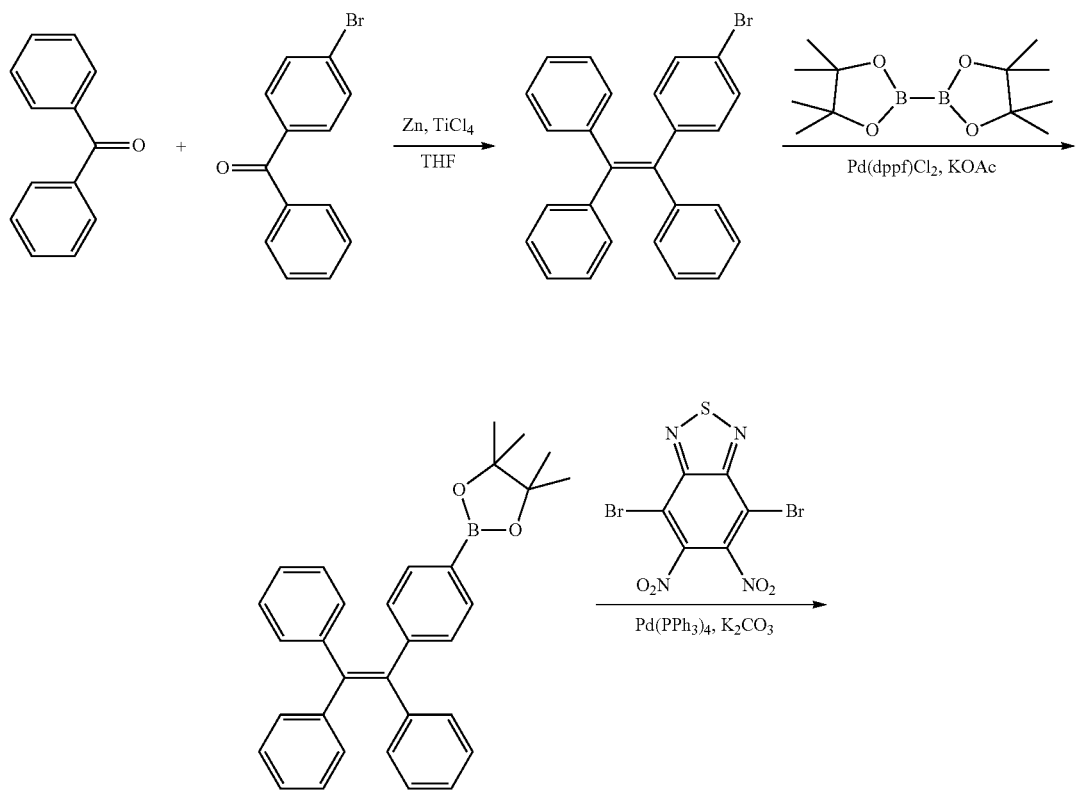

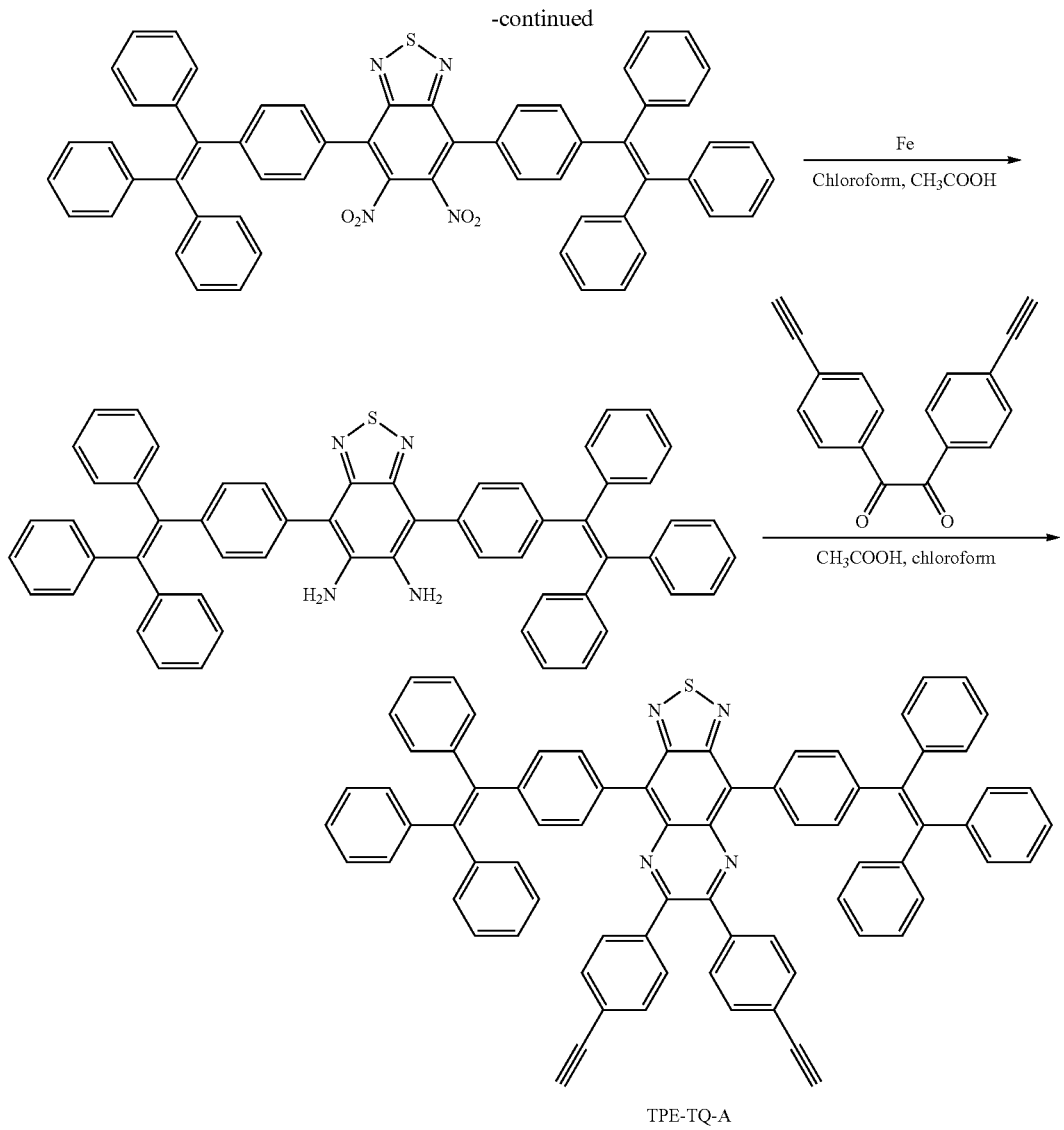

TPE-TQ-A 4,4,5,5-Tetramethyl-2-(4-(1,2,2-triphenylvinyl)phenyl)-1,3,2-dioxaborolane (2.29 g, 5 mmol), 4,7-dibromo-5,6-dinitrobenzo[c][1,2,5]thiadiazole (0.77 g, 2 mmol), and Pd(PPh$_3$)$_4$ (60 mg, 0.05 mmol) were added into a 100 mL two-necked round-bottom flask. The flask was vacuumed and purged with dry nitrogen three times. Then anhydrous tetrahydrofuran (40 mL) was added, and the mixture was heated to reflux and stirred for 24 hours in the absence of light. After cooling to room temperature, water was added, and the mixture was extracted with dichloromethane three times. The organic phase was combined and dried with MgSO$_4$. After removal of the solvent under reduced pressure, the residue was purified by column chromatography on silica gel using dichloromethane/hexane (v/v 1:4) as the eluent to result in 5,6-dinitro-4,7-bis(4-(1,2,2-triphenylvinyl)phenyl)benzo[c][1,2,5]thiadiazole as a red solid (80% yield).

5,6-Dinitro-4,7-bis(4-(1,2,2-triphenylvinyl)phenyl)benzo[c][1,2,5]thiadiazole (1.33 g, 1.5 mmol) was suspended in a solution of 50 mL of acetic acid under vigorous stirring in a 100 mL two-necked round-bottom flask, and iron power (2.24 g, 40 mmol) was added into the mixture. Then the mixture was heated to 80° C. and stirred for 12 hours. After cooling to room temperature, 100 mL of water was added. The mixture was extracted with dichloromethane three times. The organic phase was combined, washed with aqueous NaHCO$_3$, and dried with MgSO$_4$. After removal of the solvent under reduced pressure, a yellow solid (4,7-bis(4-(1,2,2-triphenylvinyl)phenyl)benzo[c][1,2,5]thiadiazole-5,6-diamine) was obtained, and it was used without further purification.

4,7-Bis(4-(1,2,2-triphenylvinyl)phenyl)benzo[c][1,2,5]thiadiazole-5,6-diamine (0.83 g, 1.0 mmol) was dissolved in chloroform (20 mL) and acetic acid (20 mL) in a 100 mL two-necked round-bottom flask under nitrogen. Then 1,2-bis(4-ethynylphenyl)ethane-1,2-dione (0.39 g, 1.5 mmol) was added into this solution. The mixture was heated to 70° C. and stirred for 12 hours. After cooling to room temperature, 100 mL of water was added. The mixture was extracted with dichloromethane three times. The organic phase was combined, washed with aqueous NaHCO$_3$, and dried with MgSO$_4$. After removal of the solvent under reduced pressure, the residue was purified by chromatography on silica gel using dichloromethane/hexane (v/v 1:3) as the eluent to result in 6,7-bis(4-ethynylphenyl)-4,9-bis(4-(1,2,2-triphenylvinyl)phenyl)-[1,2,5]thiadiazolo[3,4-g]quinoxaline (TPE-TQ-A) as a dark red solid (65% yield).
$^1$H NMR (400 MHz, CDCl$_3$, δ, ppm): 7.78 (d, 4H), 7.54 (d, 4H), 7.47 (d, 4H), 7.29 (d, 4H), 7.23-7.05 (m, 30H), 3.22 (s, 2H). $^{13}$C NMR (100 MHz, CDCl$_3$, δ, ppm): 153.15, 151.61, 143.93, 143.89, 143.78, 143.71, 141.57, 140.72, 138.49, 135.93, 132.65, 132.37, 132.13, 131.62, 131.51, 131.45, 131.43, 130.66, 129.85, 129.48, 127.83, 127.76, 127.68, 126.72, 126.59, 126.54, 126.49, 123.46, 83.19, 79.25. HRMS (MALDI) m/z calcd for C$_{76}$H$_{48}$N$_4$S 1048.3600, found 1048.3593.
Synthesis of MTPE-BTSe
The synthesis of MTPE-BTSe is shown below in Scheme 7.
Scheme 7: Synthetic route to MTPE-BTSe
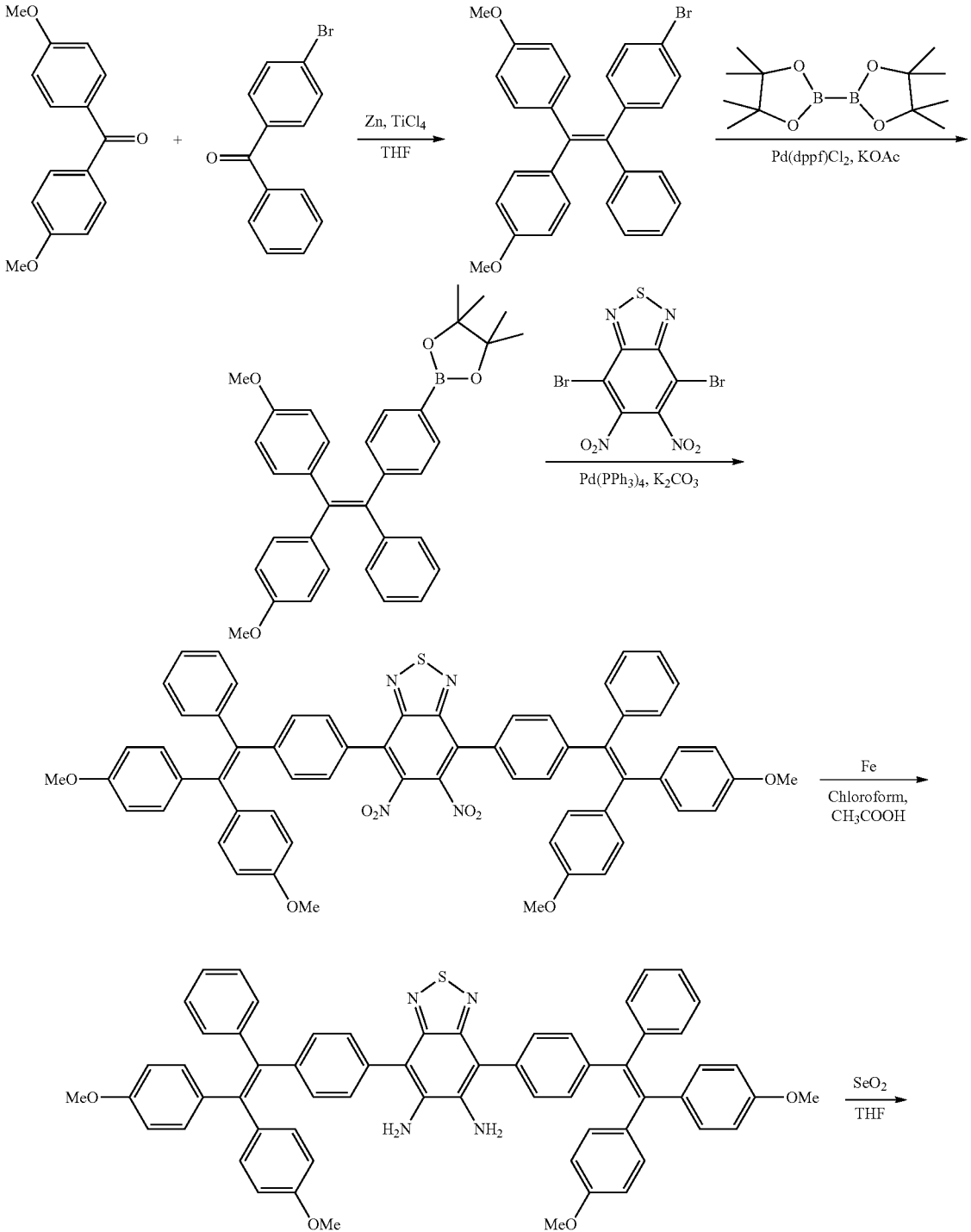

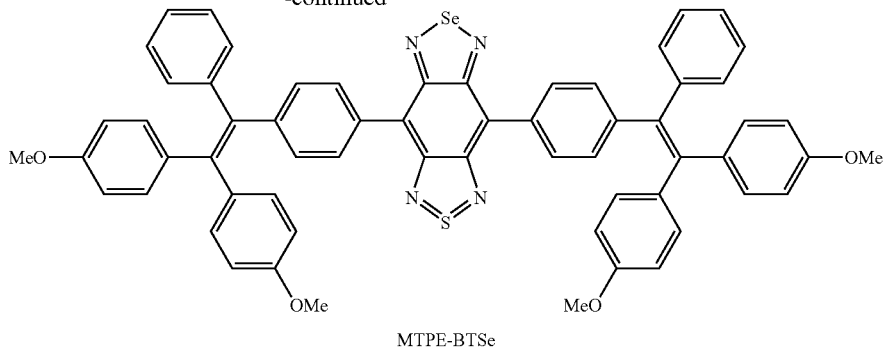

MTPE-BTSe 4,4'-dimethoxybenzophenone (20 mmol, 4.84 g), 4-bromobenzophenone (24 mmol, 6.26 g) and zinc dust (80 mmol, 5.2 g) were added to a 500 mL round-bottom flask. Then the flask was evacuated under vacuum and flushed with dry nitrogen three times. After addition of 250 mL of anhydrous THF, the mixture was cooled to −10° C., and TiCl$_4$ (7.7 mL, 70 mmol) was added dropwise and stirred for 30 minutes. The mixture was heated to reflux and stirred for 12 hours. After cooling to room temperature, the reaction was quenched by 1 M HCl solution, and the mixture was extracted with dichloromethane three times. The organic phase was combined, dried with MgSO$_4$, and the solvent was evaporated under reduced pressure. The crude product was purified on silica gel column chromatography using dichloromethane/hexane (v/v 1:5) as the eluent to give 4,4'-(2-(4-bromophenyl)-2-phenylethene-1,1-diyl)bis(methoxybenzene) as a white solid (46% yield).

4,4'-(2-(4-Bromophenyl)-2-phenylethene-1,1-diyl)bis(methoxybenzene) (3.77 g, 8 mmol), [1,1'-bis(diphenylphosphino)ferrocene]dichloropalladium (II) (Pd(dppf)Cl$_2$) (0.22 g, 0.3 mmol), KOAc (3.0 g, 30 mmol), and bis(pinacolato)diboron (3.05 g, 12 mmol) were added into a 100 mL two-necked round-bottom flask, and the flask was evacuated under vacuum and flushed with dry nitrogen three times. Anhydrous 1,4-dioxane (40 mL) was added, and the mixture was heated to reflux and stirred under nitrogen atmosphere for 24 hours. Afterwards, water was added, and the mixture was washed with dichloromethane three times. The organic phase was combined, dried with MgSO$_4$, and the solvent was evaporated under reduced pressure. The crude product was purified by silica gel column chromatography using dichloromethane/hexane (v/v 1:2) as the eluent to afford 2-(4-(2,2-bis(4-methoxyphenyl)-1-phenylvinyl)phenyl)-4,4,5,5-tetramethyl-1,3,2-dioxaborolane as a white solid (85% yield).

2-(4-(2,2-Bis(4-methoxyphenyl)-1-phenylvinyl)phenyl)-4,4,5,5-tetramethyl-1,3,2-dioxaborolane (2.59 g, 5 mmol), 4,7-dibromo-5,6-dinitrobenzo[c][1,2,5]thiadiazole (0.77 g, 2 mmol), tetrakis(triphenylphosphine)palladium (0) (Pd(PPh$_3$)$_4$) (60 mg, 0.05 mmol), and K$_2$CO$_3$ (2.07 g, 15 mmol) were added into a 100 mL two-necked round-bottom flask. The flask was vacuumed and purged with dry nitrogen three times. Then anhydrous tetrahydrofuran (40 mL) and water (10 mL) were added and the mixture was heated to reflux and stirred under nitrogen atmosphere for 24 hours in the absence of light. Afterwards, water was added, and the mixture was extracted with dichloromethane. The organic phase was combined and dried with MgSO$_4$. After removal of the solvent under reduced pressure, the residue was purified by silica gel column chromatography using dichloromethane/hexane (v/v 1:2) as the eluent to result in 4,7-bis(4-(2,2-bis(4-methoxyphenyl)-1-phenylvinyl)phenyl)-5,6-dinitrobenzo[c][1,2,5]thiadiazole as an orange solid (79% yield).

In a 250 mL two-necked round-bottom flask, 4,7-Bis(4-(2,2-bis(4-methoxyphenyl)-1-phenylvinyl)phenyl)-5,6-dinitrobenzo[c][1,2,5]thiadiazole (1.5 g, 1.5 mmol) was suspended in a solution of 80 mL of acetic acid under vigorous stirring, and iron power (2.24 g, 40 mmol) was added to the mixture. The mixture was heated to 80° C. and stirred for 24 hours. After cooling to room temperature, 150 mL of water was added, and the mixture was extracted with dichloromethane three times. The organic phase was combined, washed with aqueous NaHCO$_3$, and dried with MgSO$_4$. After removal of the solvent under reduced pressure, a dark orange solid (4,7-bis(4-(2,2-bis(4-methoxyphenyl)-1-phenylvinyl)phenyl)benzo[c][1,2,5]thiadiazole-5,6-diamine) was obtained, and it was used without further purification.

In a 100 mL two-necked round-bottom flask under nitrogen. 4,7-Bis(4-(2,2-bis(4-methoxyphenyl)-1-phenylvinyl)phenyl)benzo[c][1,2,5]thiadiazole-5,6-diamine (0.95 g, 1 mmol) was dissolved in anhydrous tetrahydrofuran (40 mL). Selenium dioxide (56 mg, 2.5 mmol) was added into this solution, and the mixture was stirred at room temperature for 18 hours. Most of the tetrahydrofuran was evaporated in vacuum and the residue was purified by neutral aluminum oxide column chromatography using dichloromethane/hexane (v/v 1:2) as the eluent to give 4,7-bis(4-(2,2-bis(4-methoxyphenyl)-1-phenylvinyl)phenyl)[1,2,5]selenadiazolo[3,4-f]benzo[c][1,2,5]-thiadiazole (MTPE-BTSe) as a green-yellow solid (2.19 g, 62% yield).

$^1$H NMR (400 MHz, CDCl$_3$, δ, ppm): 7.97 (d, 2H), 7.33-7.22 (m, 4H), 7.21-7.07 (m, 14H), 7.02-6.92 (m, 6H), 6.73-6.62 (m, 8H), 3.75 (t, 12H). HRMS (MALDI) m/z calcd for C$_{62}$H$_{46}$O$_4$N$_4$SSe 1022.2405, found 1022.2460.

Synthesis of DCDPP-2TPA
The synthesis of DCDPP-2TPA is shown below in Scheme 8.
Scheme 8: Synthetic route to DCDPP-2TPA
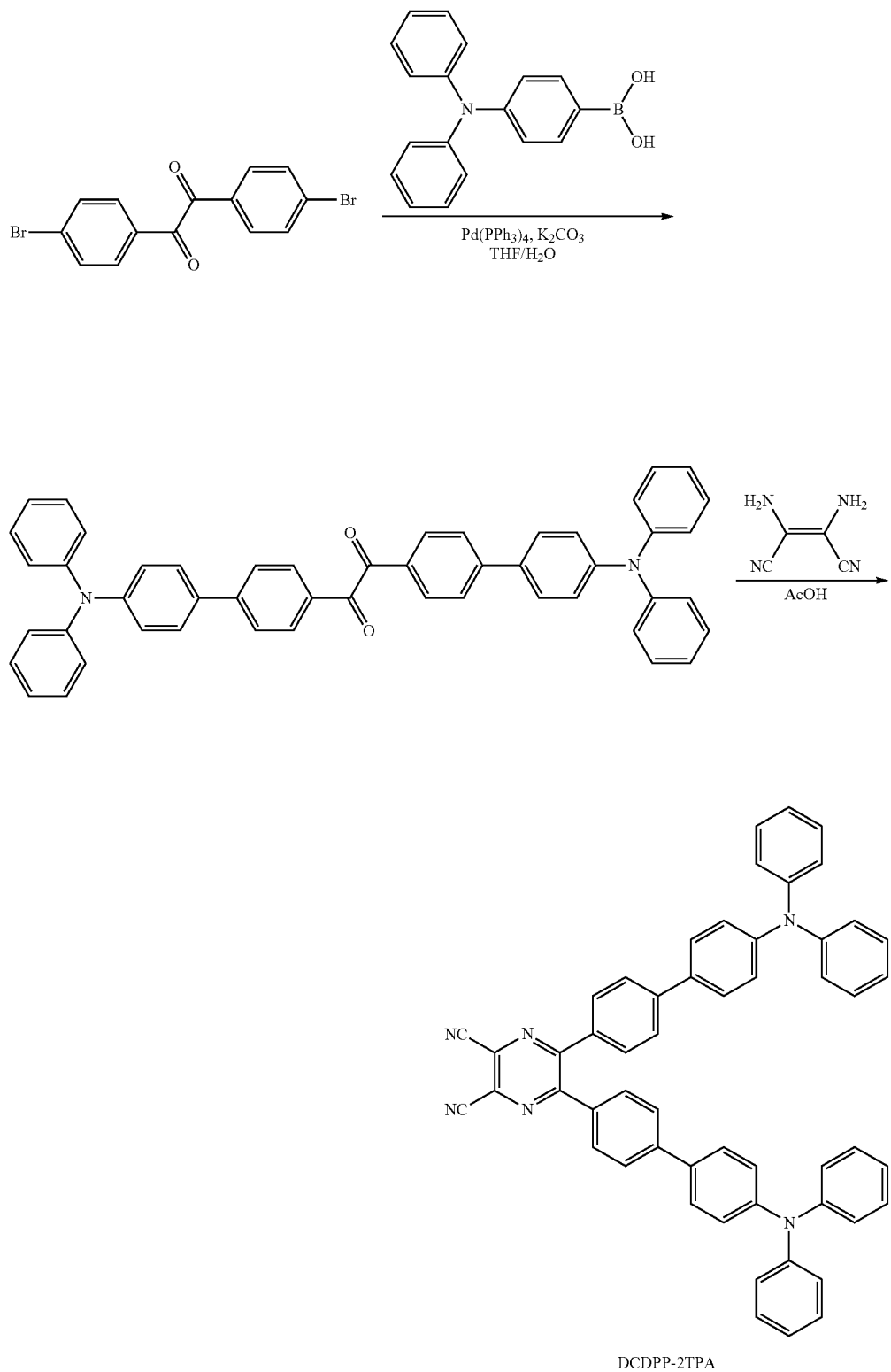
DCDPP-2TPA 1,2-bis(4'-(diphenylamino)-[1,1'-biphenyl]-4-yl) ethane-1,2-dione (600 mg, 0.86 mmol), 2,3-diaminomaleonitrile (112 mg, 1.03 mmol), and 40 mL of acetic acid were added into a 100 mL round bottom flask. The reaction was allowed to stir and reflux at 130° C. for 8 hours. After that, the mixture was cooled to room temperature and poured into ice water, followed by extraction with dichloromethane. The collected organic phase was washed with water several times and then dried over anhydrous $Na_2SO_4$. After filtration and vacuum distillation, the crude product was purified by a silica gel column with dichloromethane/hexane (1:2 by volume) as eluent. A red powder of 5,6-bis(4'-(diphenylamino)-[1,1'-biphenyl]-4-yl)pyrazine-2,3-dicarbonitrile was obtained in yield of 75.5%.

$^1$H NMR (400 MHz, $CD_2Cl_2$), δ (ppm): 7.68 (d, 4H), 7.61 (d, 4H), 7.52 (d, 4H), 7.30 (t, 8H), 7.12 (16H). $^{13}$C NMR (100 MHz, $CD_2Cl_2$), δ (ppm): 154.9, 147.4, 143.2, 133.6, 132.6, 130.4, 129.4, 127.7, 126.6, 124.8, 123.4, 123.1, 113.5. HRMS (MALDI-TOF): m/z 768.2999 [M$^+$, calcd for 768.3001].

Synthesis of DCDPP-2TPA4M

The synthesis of DCDPP-2TPA4M is shown below in Scheme 9.

Scheme 9: Synthetic route to DCDPP-2TPA4M

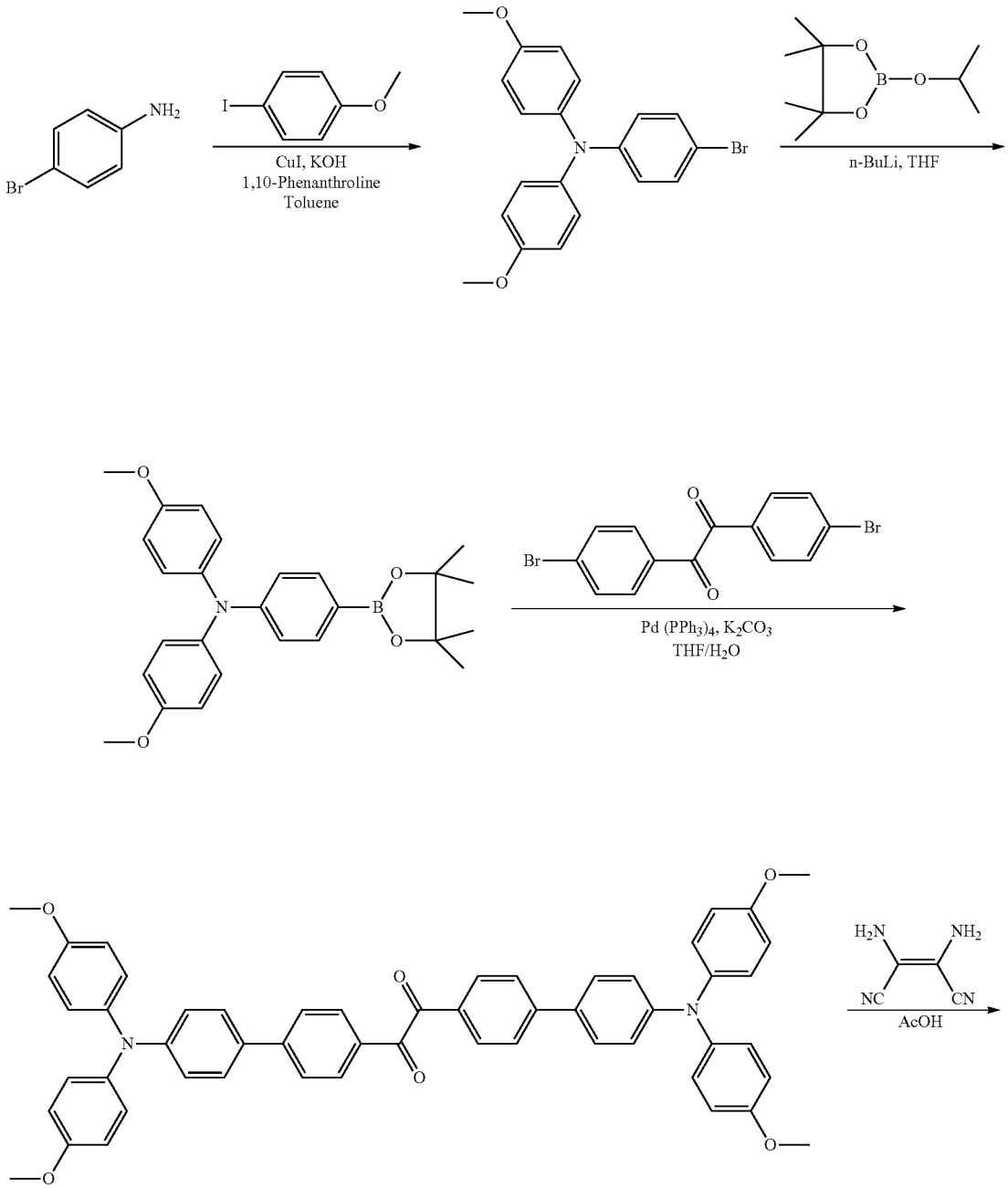

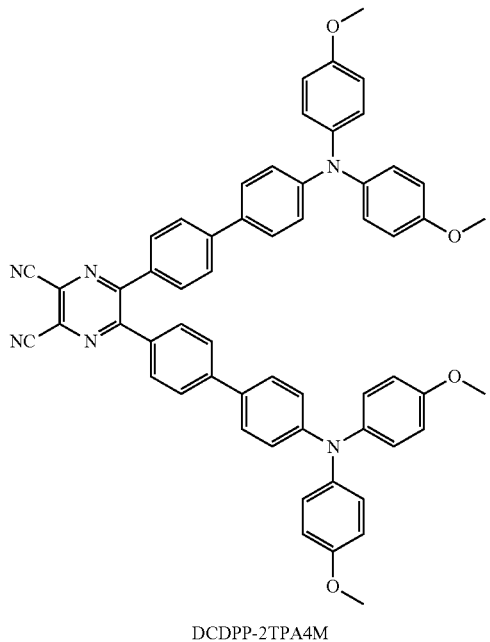

DCDPP-2TPA4M

The synthetic method is similar to that of DCDPP-2TPA. 1,2-bis(4'-(bis(4-methoxyphenyl)amino)-[1,1'-biphenyl]-4-yl)ethane-1,2-dione (500 mg, 0.61 mmol), 2,3-diaminomaleonitrile (80 mg, 0.73 mmol), and 30 mL of acetic acid were added into a 50 mL round bottom flask. The reaction was allowed to stir and reflux at 130° C. for 8 hours. After that, the mixture was cooled to room temperature and poured into ice water, followed by extraction with dichloromethane. The collected organic phase was washed with water several times and then dried over anhydrous $Na_2SO_4$. After filtration and vacuum distillation, the crude product was purified by a silica gel column with dichloromethane/hexane (1:1 by volume) as eluent, followed by recrystallizing from dichloromethane/acetonitrile. A orange-red powder of 5,6-bis(4'-(bis (4-methoxyphenyl)amino)-[1,1'-biphenyl]-4-yl)pyrazine-2,3-dicarbonitrile was obtained in yield of 70%.

$^1$H NMR (400 MHz, $CDCl_3$), δ (ppm): 7.64 (d, 4H), 7.57 (d, 4H), 7.42 (d, 4H), 7.10 (d, 8H), 6.99 (d, 4H), 6.87 (d, 8H), 3.82 (s, 12H). $^{13}$C NMR (100 MHz, $CDCl_3$), δ (ppm): 156.2, 154.8, 149.2, 143.5, 140.4, 133.1, 130.5, 130.3, 129.2, 127.5, 126.9, 126.5, 120.1, 114.8, 113.4, 55.5. HRMS (MALDI-TOF): m/z 888.3456 [M$^+$, calcd for 888.3424].

Synthesis of DCDP-2TPA

The synthesis of DCDP-2TPA is shown below in Scheme 10.

Scheme 10: Synthetic route to DCDP-2TPA

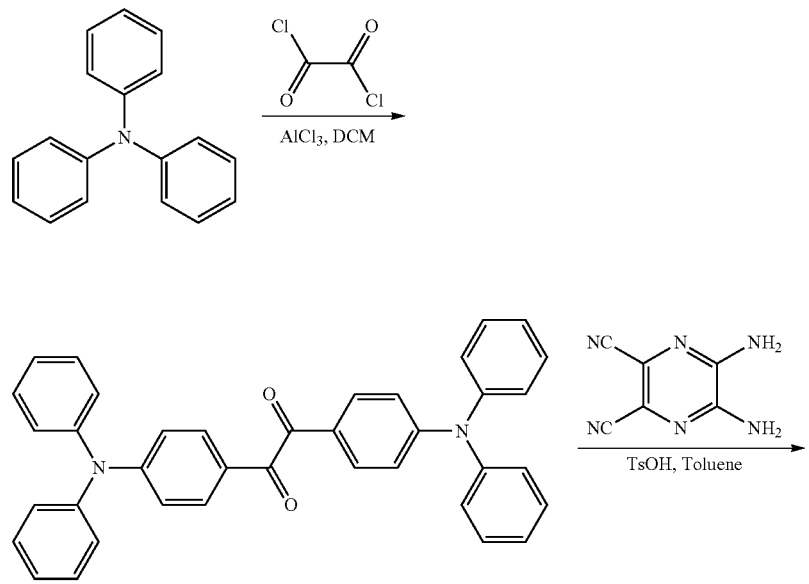

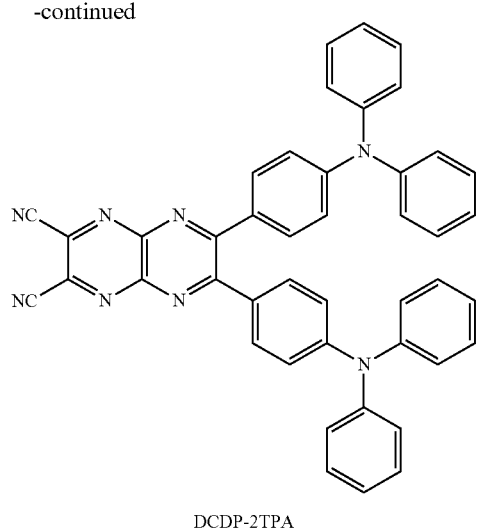

DCDP-2TPA 1,2-bis(4-(diphenylamino)phenyl) ethane-1,2-dione (245 mg, 0.45 mmol), 5,6-diaminopyrazine-2,3-dicarbonitrile (100 mg, 0.63 mol), trace amount of p-toluenesulfonic acid, and 30 mL of toluene were added into a 50 mL round bottom flask. The reaction was allowed to stir and reflux at 120° C. for 4 days. After reaction, the toluene was removed by vacuum distillation, and the crude product was extracted by dichloromethane and washed with water three times. The collected organic was then dried over anhydrous $Na_2SO_4$. After filtration and vacuum distillation, the crude product was purified by a silica gel column with dichloromethane/hexane (1:1 by volume) as eluent. A dark powder of 6,7-bis(4-(diphenylamino)phenyl)pyrazino[2,3-b] pyrazine-2,3-dicarbonitrile was obtained in yield of 59.7%.

$^1$H NMR (400 MHz, $CD_2Cl_2$), δ (ppm): 7.73 (d, 4H), 7.37 (t, 8H), 7.20 (m, 12H), 6.95 (d, 4H). $^{13}$C NMR (100 MHz, $CD_2Cl_2$), δ (ppm): 161.1, 151.7, 146.1, 144.1, 131.8, 129.7, 128.3, 126.3, 125.1, 119.2, 113.4. HRMS (MALDI-TOF): m/z 668.2467 [M$^+$, calcd for 668.2437].

Synthesis of DCDP-2TPA4M

The synthesis of DCDP-2TPA4M is shown below in Scheme 11.

Scheme 11: Synthetic route to DCDP-2TPA4M

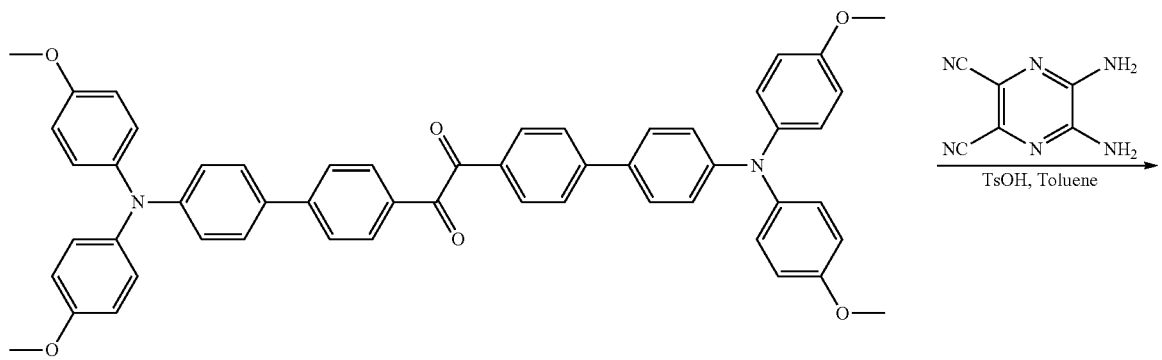

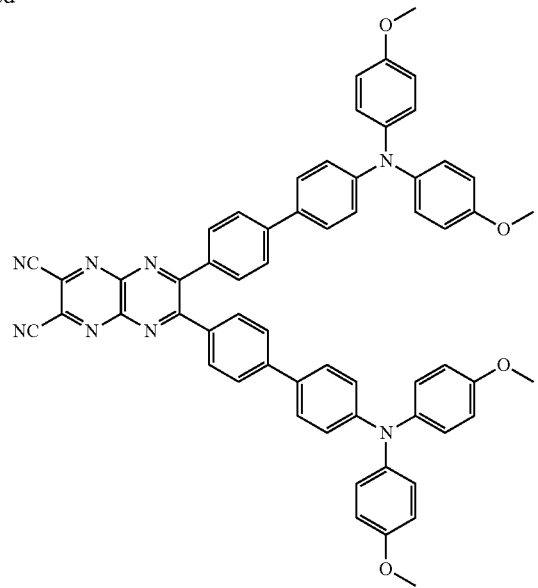

DCDP-2TPA4M

The synthetic method is similar to that of DCDP-2TPA. 1,2-bis(4'-(bis(4-methoxyphenyl)amino)-[1,1'-biphenyl]-4-yl)ethane-1,2-dione (500 mg, 0.61 mmol), 5,6-diaminopyrazine-2,3-dicarbonitrile (108 mg, 0.675 mmol), trace amount of p-toluenesulfonic acid, and 30 mL of toluene were added into a 50 mL round bottom flask. The reaction was allowed to stir and reflux at 120° C. for 4 days. After reaction, the toluene was removed by vacuum distillation, and the crude product was extracted by dichloromethane and washed with water three times. The collected organic was then dried over anhydrous $Na_2SO_4$. After filtration and vacuum distillation, the crude product was purified by a silica gel column with dichloromethane/hexane (1:1 by volume) as eluent. A dark green powder of 6,7-bis(4'-(bis (4-methoxyphenyl) amino)-[1,1'-biphenyl]-4-yl)pyrazino[2,3-b]pyrazine-2,3-dicarbonitrile was obtained in yield of 46.9%.

$^1$H NMR (400 MHz, $CDCl_3$), δ (ppm): 7.89 (d, 4H), 7.63 (d, 4H), 7.49 (d, 4H), 7.13 (d, 8H), 7.00 (d, 4H), 6.89 (d, 8H), 3.83 (s, 12H). $^{13}$C NMR (100 MHz, $CDCl_3$), δ (ppm): 161.8, 156.3, 149.4, 143.7, 144.4, 140.3, 134.0, 132.8, 131.2, 130.1, 127.6, 127.0, 126.3, 120.0, 114.8, 112.8, 55.5. HRMS (MALDI-TOF): m/z 940.3503 [M$^+$, calcd for 940.3486].

Synthesis and Characterization of DTE-TPECM

The synthesis of DTE-TPECM is shown below in Scheme 12.

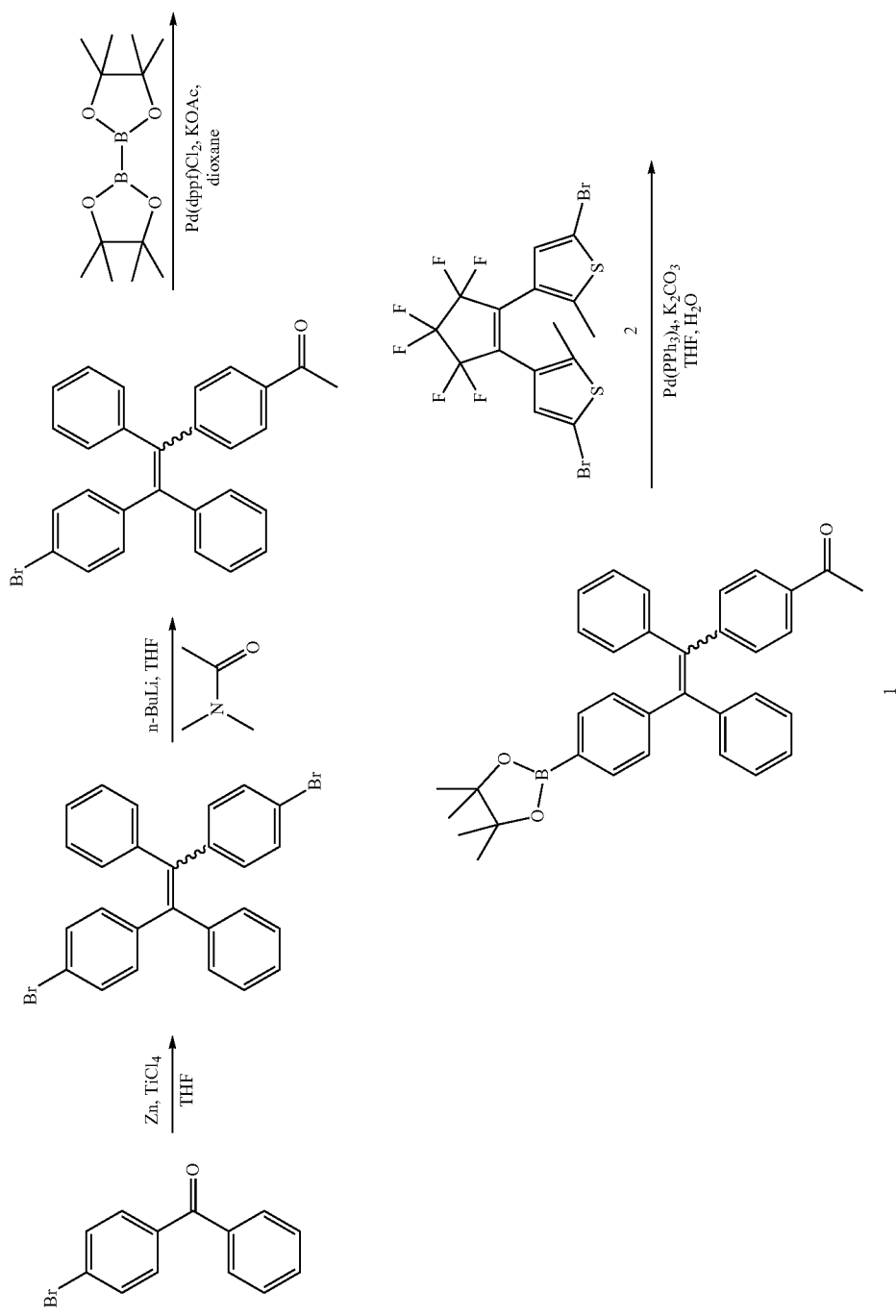
Scheme 12: Synthetic route to compound DTE-TPECM

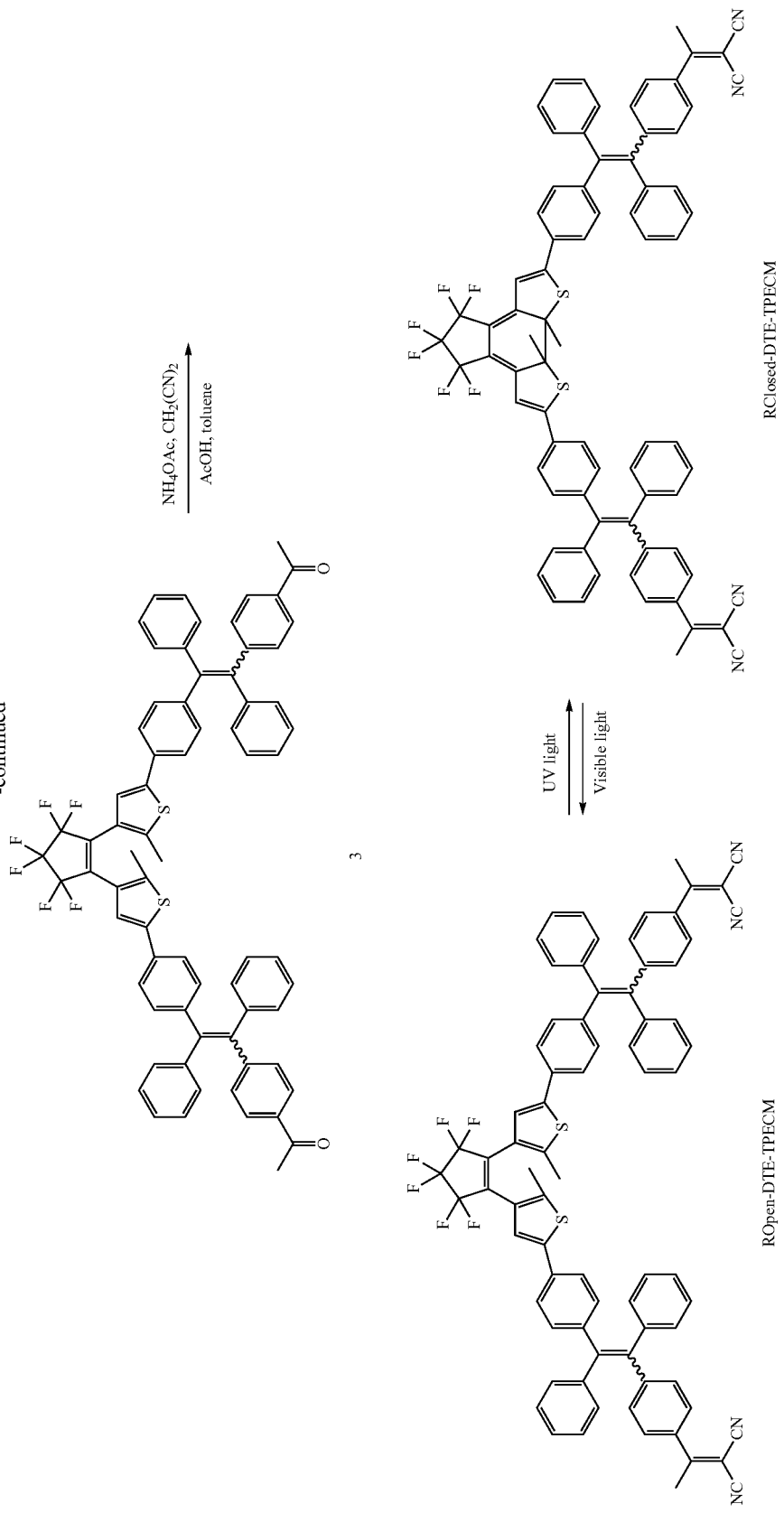

1-(4-(1,2-Diphenyl-2-(4-(4,4,5,5-tetramethyl-1,3,2-dioxaborolan-2-yl)phenyl)vinyl)phenyl)ethan-1-one (1.0 g, 2 mmol), 3,3'-(perfluorocyclopent-1-ene-1,2-diyl)bis(5-bromo-2-methylthiophene) (0.47 g, 0.9 mmol), and Pd(PPh$_3$)$_4$ (0.12 g, 0.1 mmol) were added into a 100 mL two-necked round-bottom flask. The flask was vacuumed and purged with dry nitrogen three times. Then THF (30 mL) and aqueous K$_2$CO$_3$ solution (2 M, 10 mL) were added, and the mixture was heated to reflux and stirred overnight. Water was added and the mixture was extracted with dichloromethane three times. The organic phase was combined and dried with MgSO$_4$. After the removal of the solvent under reduced pressure, the crude product was purified by column chromatography on silica gel using dichloromethane/hexane (v/v 1:1) as the eluent to afford 1,1'-(((((perfluorocyclopent-1-ene-1,2-diyl)bis(5-methylthiophene-4,2-diyl))bis(4,1-phenylene))bis(1,2-diphenylethene-2,1-diyl))bis(4,1-phenylene))bis(ethan-1-one) as a yellow solid (76% yield).

1,1'-(((((Perfluorocyclopent-1-ene-1,2-diyl)bis(5-methylthiophene-4,2-diyl))bis(4,1-phenylene))bis(1,2-diphenylethene-2,1-diyl))bis(4,1-phenylene))bis(ethan-1-one) (0.56 g, 0.5 mmol), malononitrile (0.1 g, 1.5 mmol), and ammonium acetate (0.12 g, 1.5 mmol) were added into a 100 mL two-necked round-bottom flask. The flask was vacuumed and purged with dry nitrogen three times. Then anhydrous toluene (40 mL) and acetic acid (1 mL) were added, and the mixture was heated to reflux and stirred for 4 hours. After cooling down to room temperature, water was added, and the mixture was extracted with dichloromethane. The organic phase was combined and dried with MgSO$_4$. After the removal of the solvent under reduced pressure, the crude product was purified by column chromatography on silica gel using dichloromethane/hexane (v/v 2:1) as the eluent to afford 2,2'-((((((perfluorocyclopent-1-ene-1,2-diyl)bis(5-methylthiophene-4,2-diyl))bis(4,1-phenylene)) bis(1,2-diphenylethene-2,1-diyl))bis(4,1-phenylene))bis(ethan-1-yl-1-ylidene))dimalononitrile (ROpen-DTE-TPECM) as a yellow solid (78% yield).

$^1$H NMR (400 MHz, CDCl$_3$, 25° C.) δ (ppm): 7.32-7.20 (m, 8H), 7.18-7.14 (m, 2H), 7.18-6.92 (m, 28H), 2.48 (d, 6H), 1.85 (d, 6H). HRMS (MALDI-TOF, m/z): [M]$^+$ calcd for C$_{77}$H$_{50}$N$_4$S$_2$F$_6$, 1208.3381; found, 1208.3357.

ROpen-DTE-TPECM (open-form compound) exhibits AIE characteristics. RClosed-DTE-TPECM (closed-form compound) does not show any luminescence in soluble state or in aggregate state.

The open-form compound exhibits AIE characteristics and can be used for in vivo fluorescence imaging. There is no fluorescence for the closed-form compound, but it shows strong absorption in the NIR region. As such, the closed-form compound may be used as a photoacoustic agent. Thus, the present subject matter is a light-driven transformable agent for in vivo fluorescence and a photoacoustic agent, as well as photosensitizer for photodynamic therapy.

Figure 79:
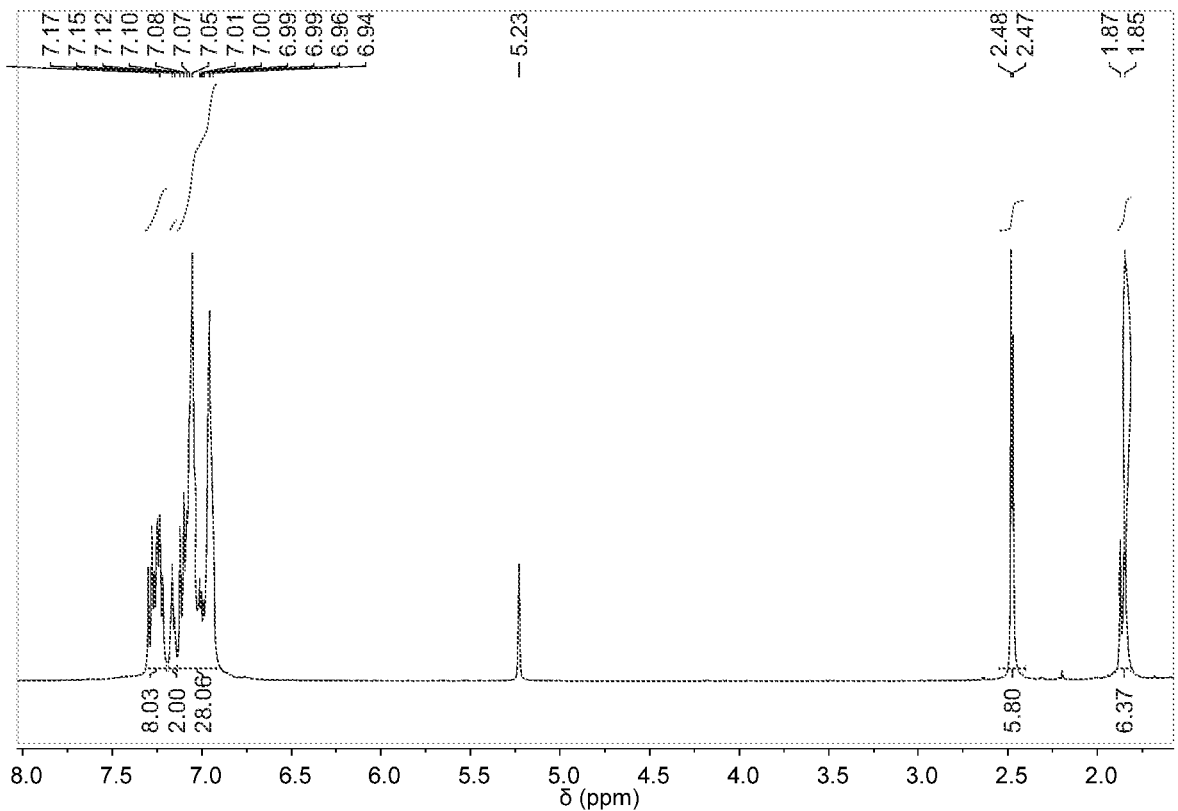
FIG. 79 shows $^1$H NMR spectrum of ROpen-DTE-TPECM in CDCl$_3$ at 298 K.
Figure 80:
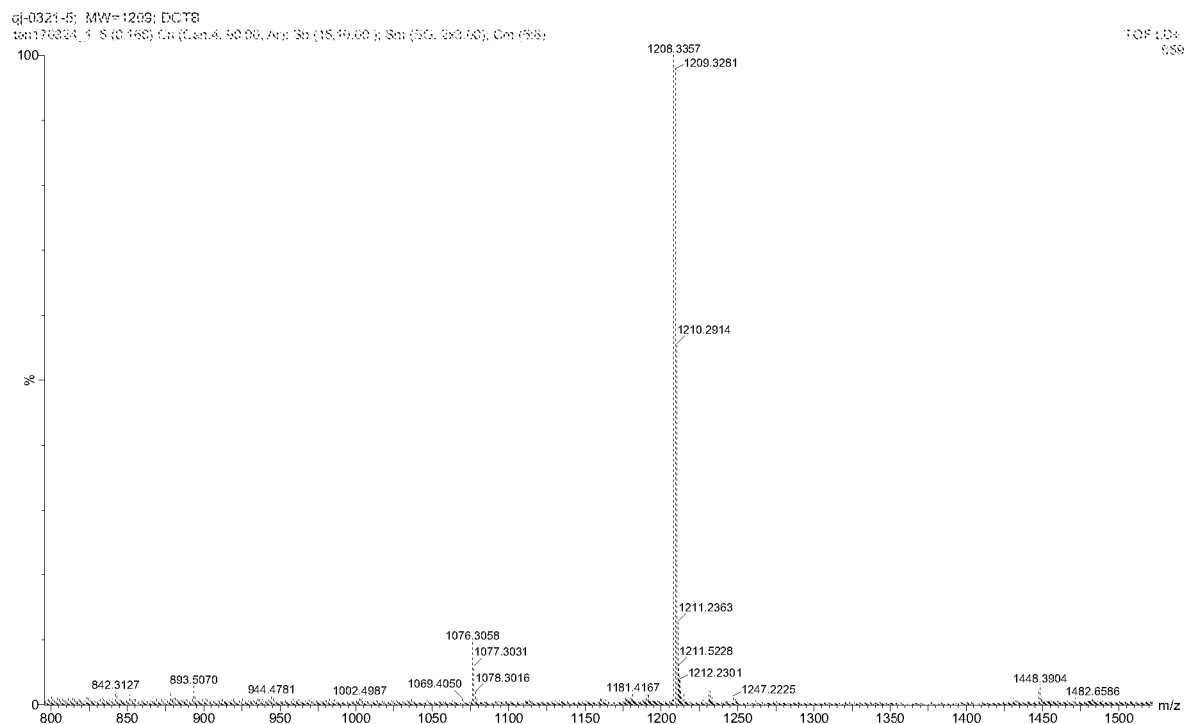
FIG. 80 shows HRMS of ROpen-DTE-TPECM.
Figure 81:
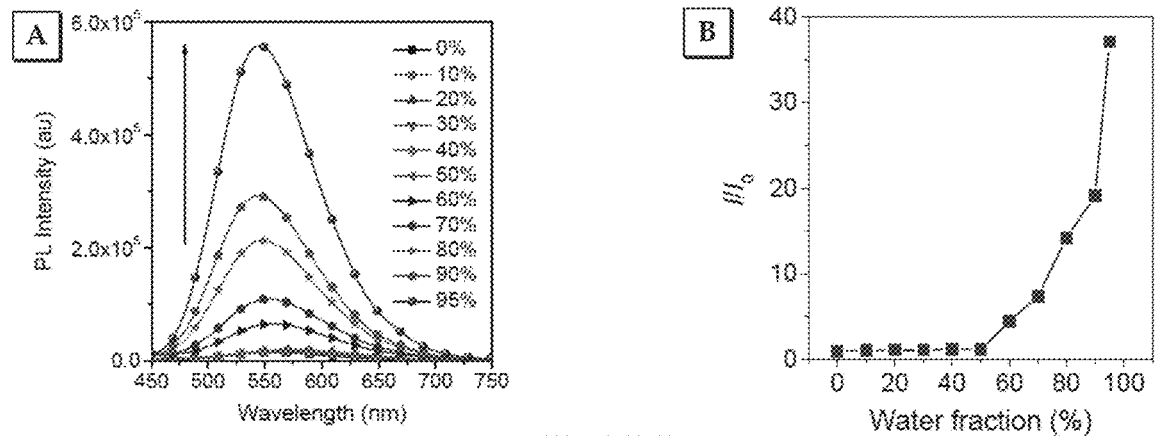
FIG. 81 shows (a) PL spectra of ROpen-DTE-TPECM in THF/water mixture with various water fractions. (b) Plot of I/I$_0$ versus water fraction. I$_0$ and I are the peak PL intensities of ROpen-DTE-TPECM (10 µM) in pure THF and THF/water mixtures, respectively. Inset shows the photographs of ROpen-DTE-TPECM in THF/water mixtures with different water fractions taken under UV illumination.
Figure 82:
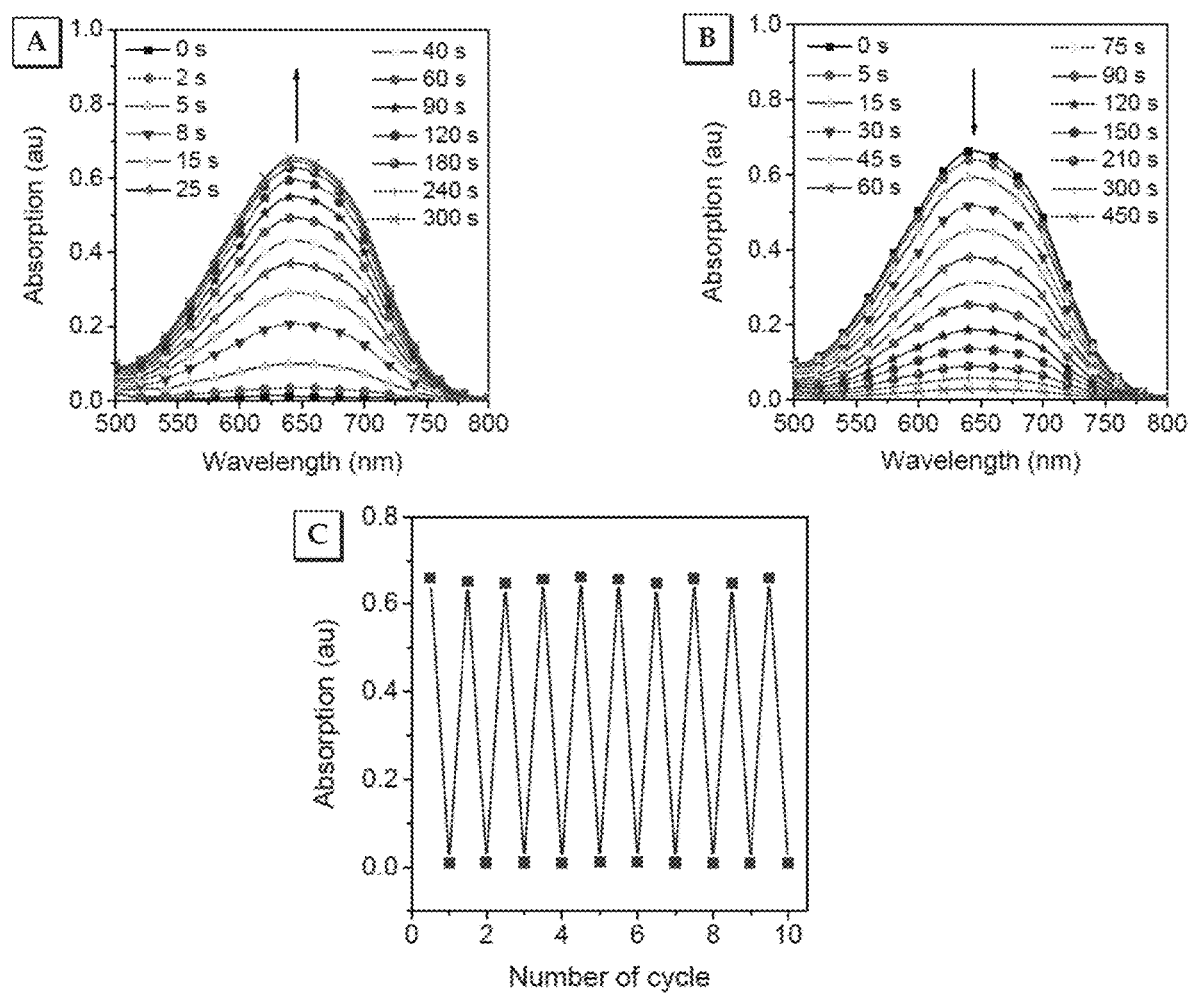
FIG. 82 shows absorption PL spectra of (a) ROpen-DTE-TPECM (THF solution) under UV light (365 nm) irradiation and (b) RClosed-DTE-TPECM (THF solution) under red light (610 nm) irradiation for different time. (c) The absorption intensity at 650 nm of DTE-TPECM in THF during ten circles of red (610 nm)-UV (365 nm) light irradiation processes, indicating good photo-reversible ring opening and closing property of the molecule.
Figure 83:
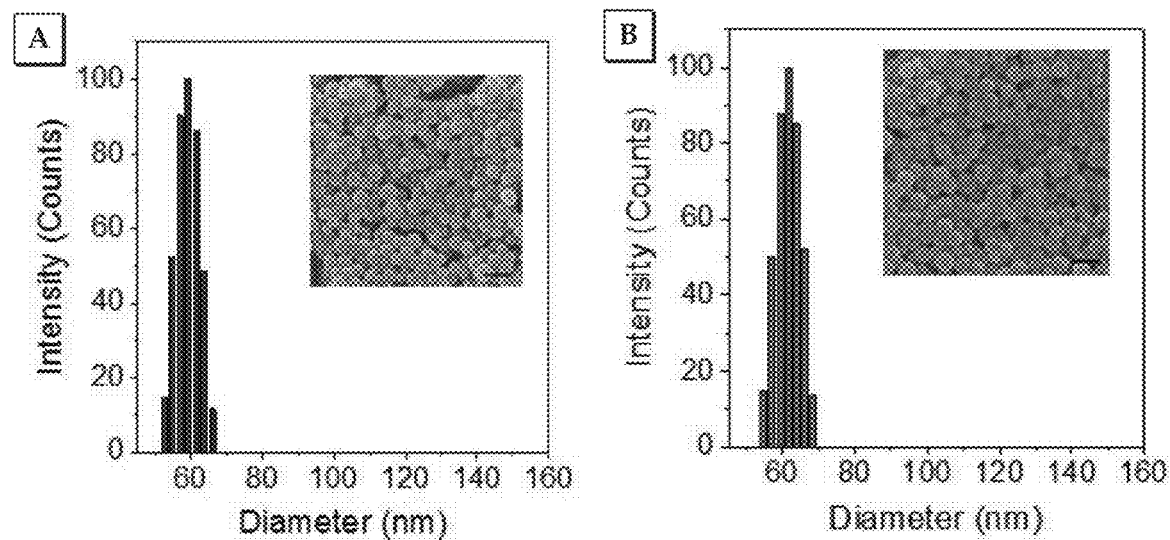
FIG. 83 shows DLS profiles and SEM images of (a) RClosed NPs and (b) ROpen NPs.
Figure 84:
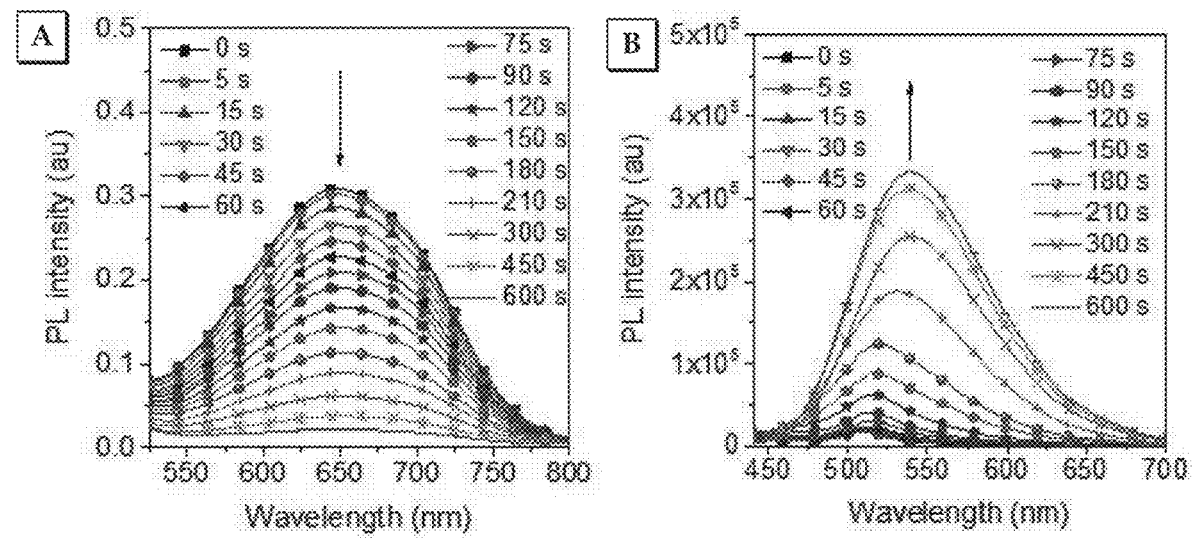
FIG. 84 shows (a) absorption and (b) PL spectra of RClosed NPs under visible light (610 nm) irradiation for different times as indicated. (c) The absorption intensity at 650 nm of the NPs during ten circles of visible (610 nm)/UV light (365 nm) irradiation processes.
Figure 84:
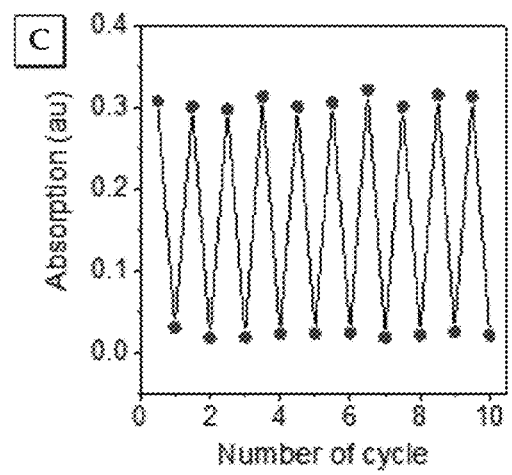
Figure 85:
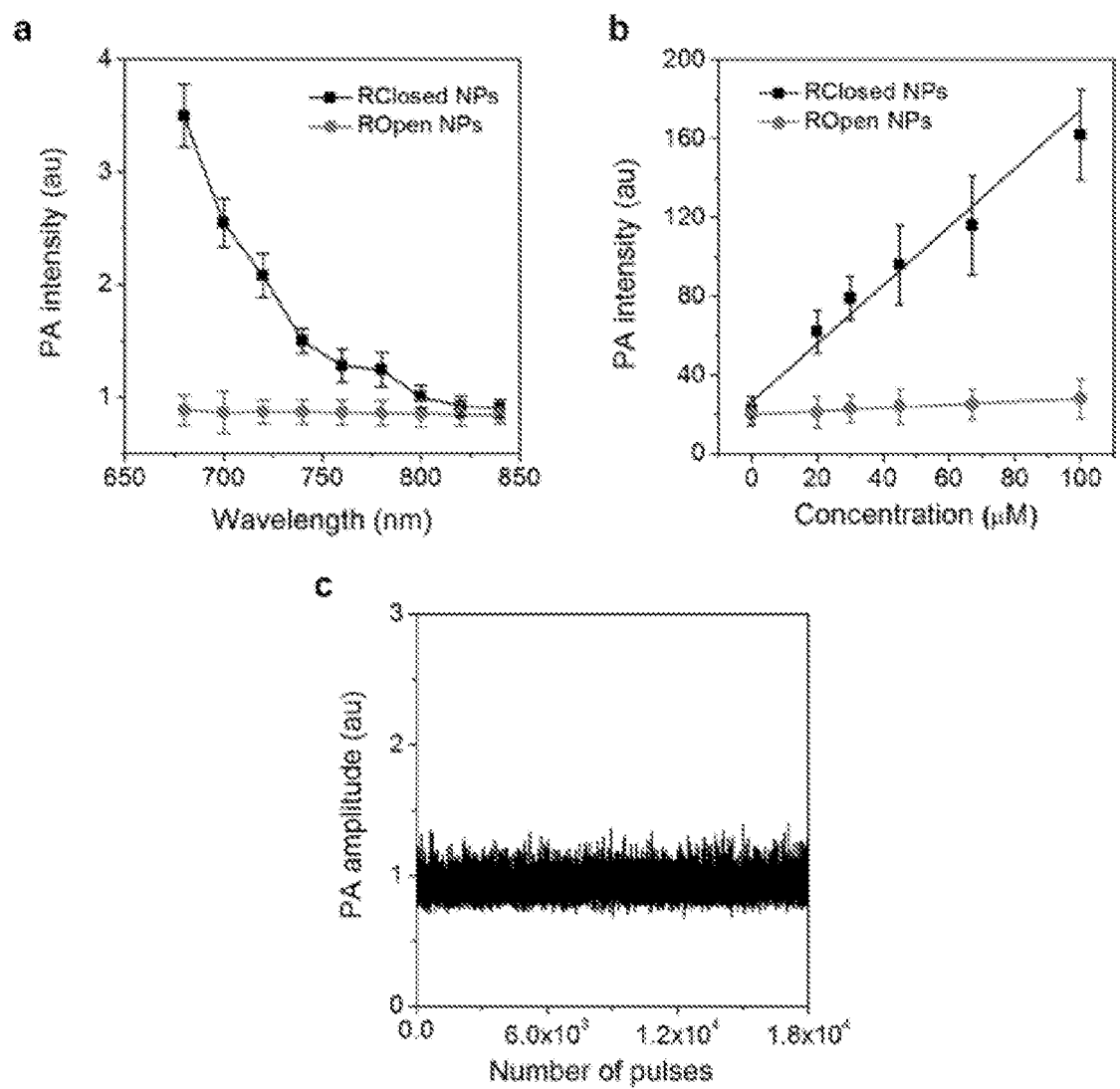
FIG. 85 shows (a) photoacoustic (PA) spectra of RClosed and ROpen NPs. (b) PA intensities of RClosed and ROpen NPs at 700 nm as a function of molar concentration based on DTE-TPECM molecules. (c) PA amplitudes of RClosed NPs as a function of number of laser pulses (1.8×10$^4$ pulses; 1.5 W cm$^{-2}$ laser and 20 Hz pulse repetition rate).
Figure 86:
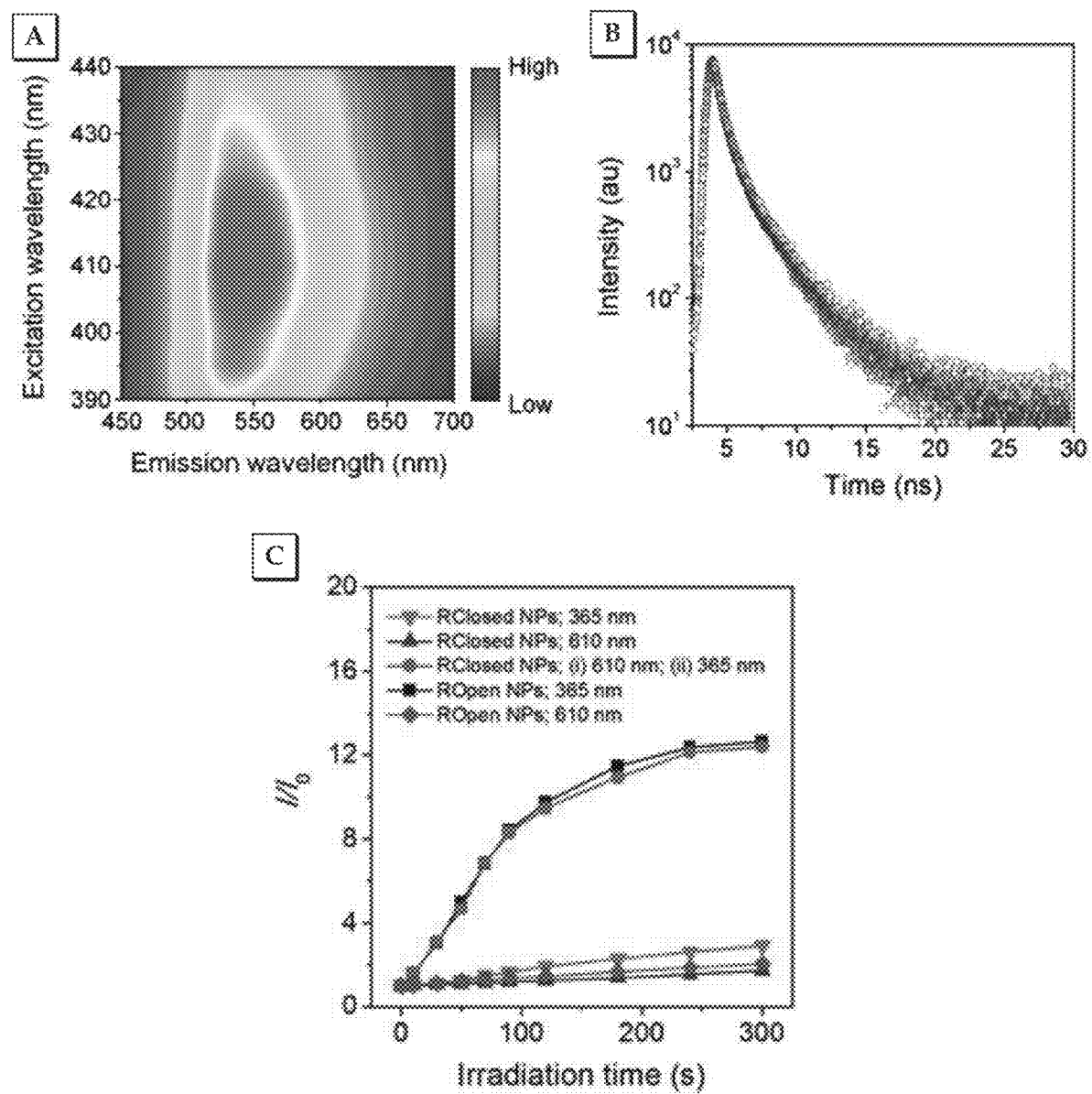
FIG. 86 shows (a) PL excitation mapping and g, fluorescence decay curve of ROpen NPs. (b) Normalized PA intensities and relative fluorescence quantum yields based on the same molar extinction coefficients at 680 nm of various agents. (c) Plot of I/I$_0$ versus light irradiation time. The aqueous solution of RClosed NPs or ROpen NPs (10 µM based on DTE-TPECM) was exposed to 610 nm red light and/or 365 nm UV light. I$_0$ and I are the PL intensity of DCF at 525 nm before and after light irradiation at designated time intervals.

The $^1$H NMR spectrum of ROpen-DTE-TPECM is shown in FIG. 79, and the HRMS of ROpen-DTE-TPECM is shown in FIG. 80. The PL spectra are shown in FIGS. 81, 82, and 84. DLS profiles and SEM images are shown in FIG. 83. PA spectra and amplitudes are shown in FIG. 85. The PL excitation mapping and fluorescence decay are shown in FIG. 86.

Figure 87:
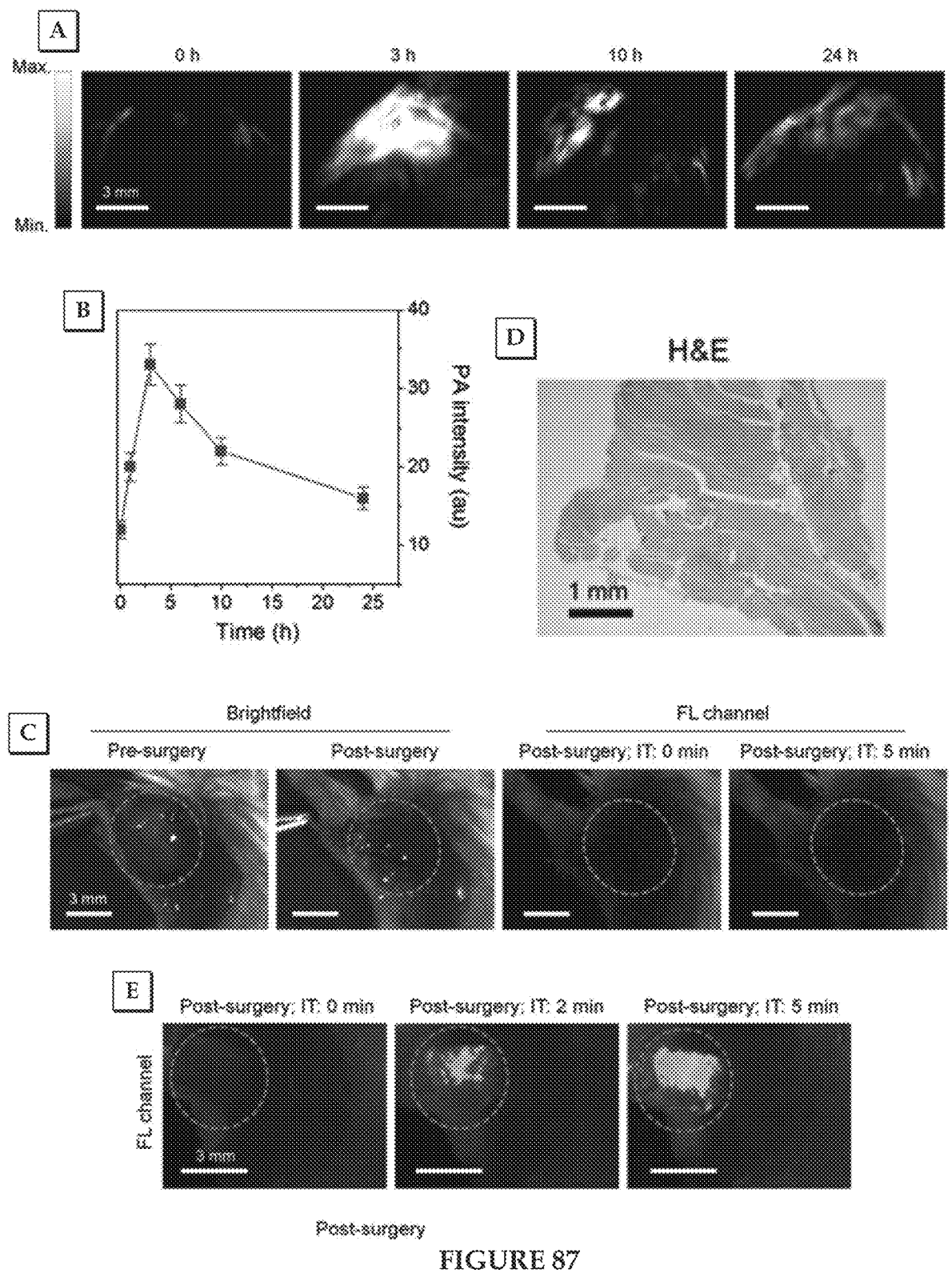
FIG. 87 shows (a) representative PA images of subcutaneous tumor from a living mouse after intravenous administration of RClosed NPs (800 µM based on RClosed-DTE-TPECM, 100 µL) at designated time intervals. (b) Plot of PA intensity at 700 nm in tumor versus time post-injection of RClosed NPs. Data are presented as mean±standard deviation (SD) (n=3 mice). (c) Representative brightfield images of RClosed NPs-treated tumor-bearing mice before and after surgery as well as representative fluorescence images of mice with complete surgical resection of tumors, followed by 610 nm red light irradiation at the operative incision site for 5 min. FL: fluorescence; IT: irradiation time. (d) H&E stained tissues at the operative incision site in (c) indicate no residual tumors left behind. (e) Representative fluorescence images of RClosed NPs-treated mice with residual tumors post-surgery. The operative incision site was irradiated by 610 nm red light for different time points. The red dashed circles in (c) and (e) indicate the tumor/operative incision site. The red arrow shows the residual tumors with a diameter below 1 mm. (f) H&E stained tissues at the operative incision site in (e) confirm the existence of residual tumors. (g) Average fluorescence intensity of residual tumors and surrounding normal tissues in (e) (n=5 mice).  represents P<0.01, in comparison between residual tumor and normal tissue. (h) Time-dependent bioluminescence imaging of residual tumors from mice in different groups. The tumors were debulked on day 0. The 4T1 cancer cells express luciferase, permitting bioluminescence imaging. The black arrows indicate the residual tumor. DS: debulking surgery. (i) Quantitative analysis of bioluminescence intensities of residual tumors from mice with various treatments as indicated.  in (i) represent P<0.01, in comparison between "DS+NPs+Light" cohort and other groups.
Figure 87:
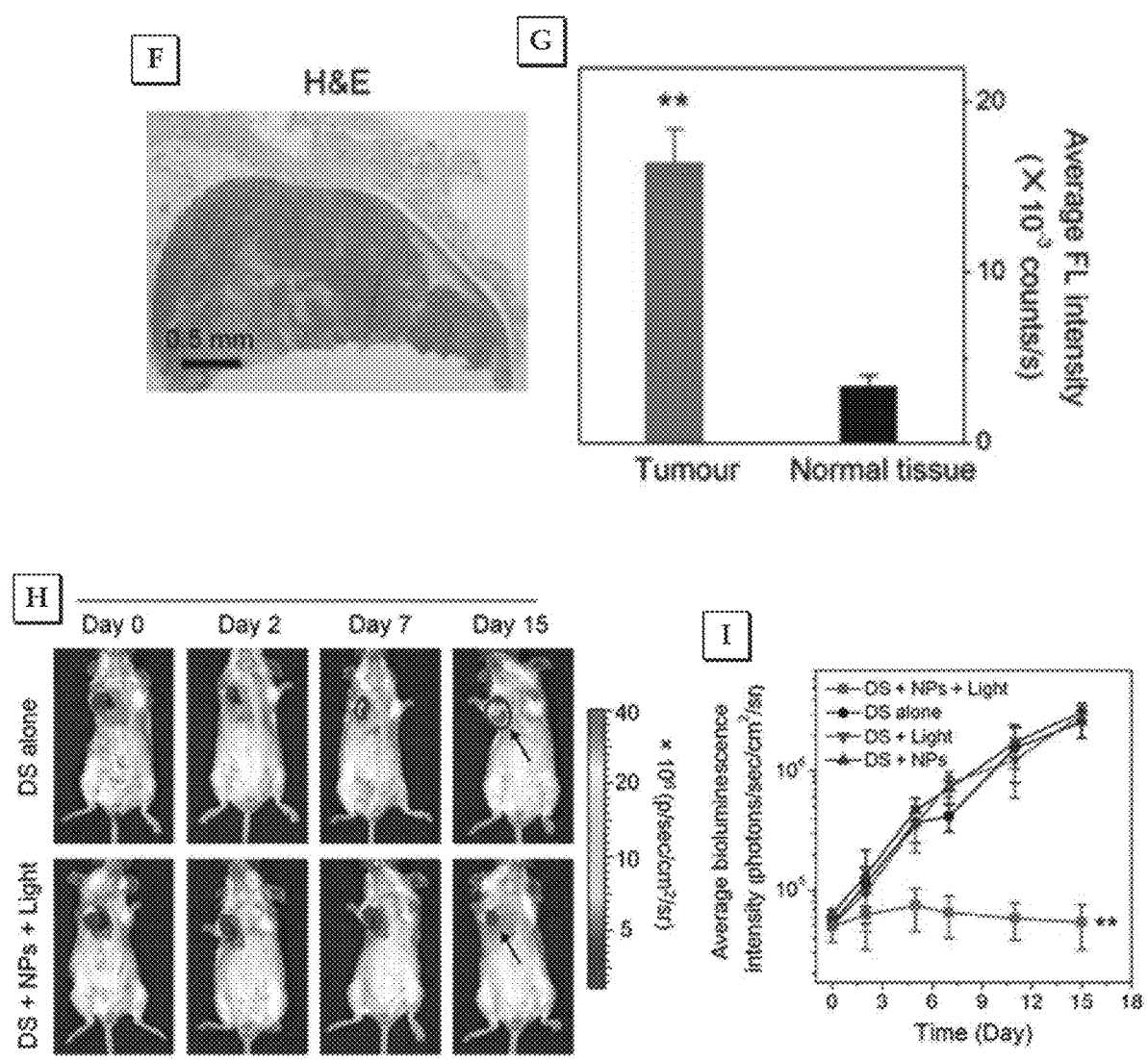

Representative PA images of subcutaneous tumor from a living mouse after intravenous administration of RClosed NPs (800 μM based on RClosed-DTE-TPECM, 100 μL) at designated time intervals are shown in FIG. 87*a*. A plot of PA intensity at 700 nm in tumor versus time post-injection of RClosed NPs are shown in FIG. 87*b*, wherein data are presented as mean±standard deviation (SD) (n=3 mice). Representative brightfield images of RClosed NPs-treated tumor-bearing mice before and after surgery as well as representative fluorescence images of mice with complete surgical resection of tumors, followed by 610 nm red light irradiation at the operative incision site for 5 min are shown in FIG. 87*c*. FL: fluorescence; IT: irradiation time. In FIG. 87*d*, H&E stained tissues at the operative incision site in (c) indicate no residual tumors left behind. In FIG. 87*e*, representative fluorescence images of RClosed NPs-treated mice with residual tumors post-surgery are shown. The operative incision site was irradiated by 610 nm red light for different time points. The red dashed circles in (c) and (e) indicate the tumor/operative incision site. The red arrow shows the residual tumors with a diameter below 1 mm. In FIG. 87*f*, H&E stained tissues at the operative incision site in (e) confirm the existence of residual tumors. In FIG. 87*g*, average fluorescence intensity of residual tumors and surrounding normal tissues in (e) (n=5 mice).  represents P<0.01, in comparison between residual tumor and normal tissue. Time-dependent bioluminescence imaging of residual tumors from mice in different groups are shown in FIG. 87***h*. The tumors were debulked on day 0. The 4T1 cancer cells express luciferase, permitting bioluminescence imaging. The black arrows indicate the residual tumor. DS: debulking surgery. In FIG. 87*i*, quantitative analysis of bioluminescence intensities of residual tumors from mice with various treatments as indicated. ** in (i) represent P<0.01, in comparison between "DS+NPs+Light" cohort and other groups.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

We claim:

1. A compound comprising a donor and an acceptor, wherein the compound is DTE-TPECM and has a structure selected from the group consisting of:

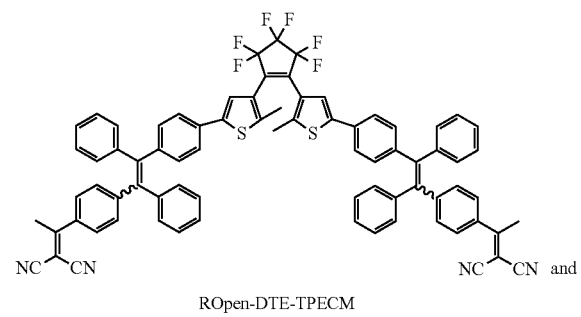

ROpen-DTE-TPECM

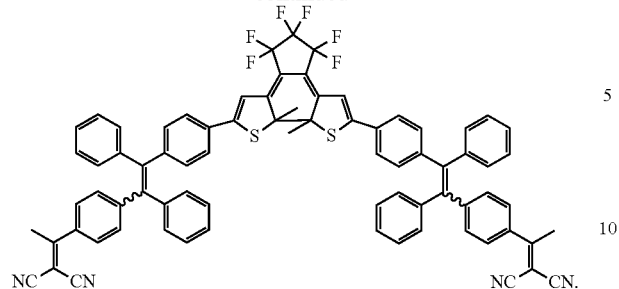

RClosed-DTE-TPECM

2. The compound of claim 1, wherein the structure is ROpen-DTE-TPECM and the compound exhibits AIE characteristics useful for in vivo fluorescence imaging.

3. The compound of claim 1, wherein the structure is RClosed-DTE-TPECM and the compound is useful as a photoacoustic agent.

4. A probe comprising the compound of claim 1, wherein the compound is in a PEG matrix in a form of nanoparticles.

* * * * *